(12) United States Patent
Ryan

(10) Patent No.: US 7,985,571 B1
(45) Date of Patent: Jul. 26, 2011

(54) ISOLATED GENOMIC POLYNUCLEOTIDE FRAGMENTS FROM CHROMOSOME 17 THAT ENCODE HUMAN CARBOXYPEPTIDASE D

(75) Inventor: James W Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 541 days.

(21) Appl. No.: 11/876,673

(22) Filed: Oct. 22, 2007

Related U.S. Application Data

(63) Continuation of application No. 10/457,716, filed on Jun. 9, 2003, now abandoned.

(60) Provisional application No. 60/386,927, filed on Jun. 7, 2002.

(51) Int. Cl.
- *C12N 9/64* (2006.01)
- *C12N 15/70* (2006.01)
- *C12N 1/20* (2006.01)
- *C12Q 1/68* (2006.01)
- *C12P 21/06* (2006.01)
- *C07H 21/04* (2006.01)

(52) U.S. Cl. ........ 435/226; 435/6; 435/69.1; 435/320.1; 435/252.3; 536/23.2

(58) Field of Classification Search .......... None
See application file for complete search history.

(56) References Cited

U.S. PATENT DOCUMENTS
5,998,373 A * 12/1999 Hillman et al. ............ 514/12

OTHER PUBLICATIONS
Zhao et al. Apr. 23, 2005 GenBank accession AQ478151.
Breiner et al. 2001 J. Vriol. 75:143-150.
Varlamov et al. 1999, J. Biol. Chem. 274:14759-14767.
Dong et al. 1999 Neuroscience 89:1301-1317.
Ishikawa et al. 1998 Gene 215:361-370.
Birren et al. Nov. 24, 1998 GenBank accession AC006050.
Song et al. 1995 J. Biol. Chem. 270:25007-25013.
Watson et al 1992 "Recombinant DNA" 2nd edtition, pp. 137-140.

* cited by examiner

*Primary Examiner* — Anand Desai
*Assistant Examiner* — Iqbal H Chowdhury
(74) *Attorney, Agent, or Firm* — Cheryl H. Agris

(57) ABSTRACT

The invention is directed to isolated genomic polynucleotide fragments that encode human carboxypeptidase D, vectors and hosts containing the fragment and fragments hybridizing to noncoding regions as well as antisense oligonucleotides to these fragments. The invention is further directed to methods of using these fragments to obtain human Carboxypeptidase D and to diagnose, treat, prevent and/or ameliorate a pathological disorder.

7 Claims, No Drawings

SEQUENCE LISTING

```
<160> NUMBER OF SEQ ID NOS: 3

<210> SEQ ID NO 1
<211> LENGTH: 1380
<212> TYPE: PRT
<213> ORGANISM: Homo sapiens

<400> SEQUENCE: 1
```

Met Ala Ser Gly Arg Asp Glu Arg Pro Pro Trp Arg Leu Gly Arg Leu
1               5                   10                  15

Leu Leu Leu Met Cys Leu Leu Leu Leu Gly Ser Ser Ala Arg Ala Ala
            20                  25                  30

His Ile Lys Lys Ala Glu Ala Thr Thr Thr Thr Ser Ala Gly Ala
        35                  40                  45

Glu Ala Ala Glu Gly Gln Phe Asp Arg Tyr Tyr His Glu Glu Glu Leu
    50                  55                  60

Glu Ser Ala Leu Arg Glu Ala Ala Ala Gly Leu Pro Gly Leu Ala
65                  70                  75                  80

Arg Leu Phe Ser Ile Gly Arg Ser Val Glu Gly Arg Pro Leu Trp Val
                85                  90                  95

Leu Arg Leu Thr Ala Gly Leu Gly Ser Leu Ile Pro Glu Gly Asp Ala
            100                 105                 110

Gly Pro Asp Ala Ala Gly Pro Asp Ala Ala Gly Pro Leu Leu Pro Gly
        115                 120                 125

Arg Pro Gln Val Lys Leu Val Gly Asn Met His Gly Asp Glu Thr Val
    130                 135                 140

Ser Arg Gln Val Leu Ile Tyr Leu Ala Arg Glu Leu Ala Ala Gly Tyr

-continued

```
                145                 150                 155                 160
Arg Arg Gly Asp Pro Arg Leu Val Arg Leu Leu Asn Thr Thr Asp Val
                165                 170                 175
Tyr Leu Leu Pro Ser Leu Asn Pro Asp Gly Phe Glu Arg Ala Arg Glu
                180                 185                 190
Gly Asp Cys Gly Phe Gly Asp Gly Pro Ser Gly Ala Ser Gly Arg
            195                 200                 205
Asp Asn Ser Arg Gly Arg Asp Leu Asn Arg Ser Phe Pro Asp Gln Phe
210                 215                 220
Ser Thr Gly Glu Pro Pro Ala Leu Asp Glu Val Pro Glu Val Arg Ala
225                 230                 235                 240
Leu Ile Glu Trp Ile Arg Arg Asn Lys Phe Val Leu Ser Gly Asn Leu
                245                 250                 255
His Gly Gly Ser Val Val Ala Ser Tyr Pro Phe Asp Asp Ser Pro Glu
            260                 265                 270
His Lys Ala Thr Gly Ile Tyr Ser Lys Thr Ser Asp Asp Glu Val Phe
        275                 280                 285
Lys Tyr Leu Ala Lys Ala Tyr Ala Ser Asn His Pro Ile Met Lys Thr
290                 295                 300
Gly Glu Pro His Cys Pro Gly Asp Glu Asp Glu Thr Phe Lys Asp Gly
305                 310                 315                 320
Ile Thr Asn Gly Ala His Trp Tyr Asp Val Glu Gly Gly Met Gln Asp
                325                 330                 335
Tyr Asn Tyr Val Trp Ala Asn Cys Phe Glu Ile Thr Leu Glu Leu Ser
            340                 345                 350
Cys Cys Lys Tyr Pro Pro Ala Ser Gln Leu Arg Gln Glu Trp Glu Asn
        355                 360                 365
Asn Arg Glu Ser Leu Ile Thr Leu Ile Glu Lys Val His Ile Gly Val
        370                 375                 380
Lys Gly Phe Val Lys Asp Ser Ile Thr Gly Ser Gly Leu Glu Asn Ala
385                 390                 395                 400
Thr Ile Ser Val Ala Gly Ile Asn His Asn Ile Thr Thr Gly Arg Phe
                405                 410                 415
Gly Asp Phe Tyr Arg Leu Leu Val Pro Gly Thr Tyr Asn Leu Thr Val
            420                 425                 430
Val Leu Thr Gly Tyr Met Pro Leu Thr Val Thr Asn Val Val Val Lys
        435                 440                 445
Glu Gly Pro Ala Thr Glu Val Asp Phe Ser Leu Arg Pro Thr Val Thr
        450                 455                 460
Ser Val Ile Pro Asp Thr Thr Glu Ala Val Ser Thr Ala Ser Thr Val
465                 470                 475                 480
Ala Ile Pro Asn Ile Leu Ser Gly Thr Ser Ser Ser Tyr Gln Pro Ile
                485                 490                 495
Gln Pro Lys Asp Phe His His His Phe Pro Asp Met Glu Ile Phe
            500                 505                 510
Leu Arg Arg Phe Ala Asn Glu Tyr Pro Asn Ile Thr Arg Leu Tyr Ser
        515                 520                 525
Leu Gly Lys Ser Val Glu Ser Arg Glu Leu Tyr Val Met Glu Ile Ser
        530                 535                 540
Asp Asn Pro Gly Val His Glu Pro Gly Glu Pro Glu Phe Lys Tyr Ile
545                 550                 555                 560
Gly Asn Met His Gly Asn Glu Val Val Gly Arg Glu Leu Leu Leu Asn
                565                 570                 575
```

```
                                    -continued

Leu Ile Glu Tyr Leu Cys Lys Asn Phe Gly Thr Asp Pro Glu Val Thr
            580                 585                 590

Asp Leu Val His Asn Thr Arg Ile His Leu Met Pro Ser Met Asn Pro
        595                 600                 605

Asp Gly Tyr Glu Lys Ser Gln Glu Gly Asp Ser Ile Ser Val Ile Gly
    610                 615                 620

Arg Asn Asn Ser Asn Asn Phe Asp Leu Asn Arg Asn Phe Pro Asp Gln
625                 630                 635                 640

Phe Val Gln Ile Thr Asp Pro Thr Gln Pro Glu Thr Ile Ala Val Met
                645                 650                 655

Ser Trp Met Lys Ser Tyr Pro Phe Val Leu Ser Ala Asn Leu His Gly
            660                 665                 670

Gly Ser Leu Val Val Asn Tyr Pro Phe Asp Asp Asp Glu Gln Gly Leu
        675                 680                 685

Ala Thr Tyr Ser Lys Ser Pro Asp Asp Ala Val Phe Gln Gln Ile Ala
    690                 695                 700

Leu Ser Tyr Ser Lys Glu Asn Ser Gln Met Phe Gln Gly Arg Pro Cys
705                 710                 715                 720

Lys Asn Met Tyr Pro Asn Glu Tyr Phe Pro His Gly Ile Thr Asn Gly
                725                 730                 735

Ala Ser Trp Tyr Asn Val Pro Gly Gly Met Gln Asp Trp Asn Tyr Leu
            740                 745                 750

Gln Thr Asn Cys Phe Glu Val Thr Ile Glu Leu Gly Cys Val Lys Tyr
        755                 760                 765

Pro Leu Glu Lys Glu Leu Pro Asn Phe Trp Gln Asn Arg Arg Ser
    770                 775                 780

Leu Ile Gln Phe Met Lys Gln Val His Gln Gly Val Arg Gly Phe Val
785                 790                 795                 800

Leu Asp Ala Thr Asp Gly Arg Gly Ile Leu Asn Ala Thr Ile Ser Val
                805                 810                 815

Ala Glu Ile Asn His Pro Val Thr Thr Tyr Lys Thr Gly Asp Tyr Trp
            820                 825                 830

Arg Leu Leu Val Pro Gly Thr Tyr Lys Ile Thr Ala Ser Ala Arg Gly
        835                 840                 845

Tyr Asn Pro Val Thr Lys Asn Val Thr Val Lys Ser Glu Gly Ala Ile
    850                 855                 860

Gln Val Asn Phe Thr Leu Val Arg Ser Ser Thr Asp Ser Asn Asn Glu
865                 870                 875                 880

Ser Lys Lys Gly Lys Gly Ala Ser Ser Thr Asn Asp Ala Ser Val
                885                 890                 895

Pro Thr Thr Lys Glu Phe Glu Thr Leu Ile Lys Asp Leu Ser Ala Glu
            900                 905                 910

Asn Gly Leu Glu Ser Leu Met Leu Arg Ser Ser Asn Leu Ala Leu
        915                 920                 925

Ala Leu Tyr Arg Tyr His Ser Tyr Lys Asp Leu Ser Glu Phe Leu Arg
    930                 935                 940

Gly Leu Val Met Asn Tyr Pro His Ile Thr Asn Leu Thr Asn Leu Gly
945                 950                 955                 960

Gln Ser Thr Glu Tyr Arg His Ile Trp Ser Leu Glu Ile Ser Asn Lys
                965                 970                 975

Pro Asn Val Ser Glu Pro Glu Pro Lys Ile Arg Phe Val Ala Gly
            980                 985                 990

Ile His Gly Asn Ala Pro Val Gly  Thr Glu Leu Leu Leu  Ala Leu Ala
        995                 1000                1005
```

| | | | | | | | | | | |
|---|---|---|---|---|---|---|---|---|---|---|
| Glu | Phe | Leu | Cys | Leu | Asn | Tyr | Lys | Lys | Asn | Pro | Ala | Val | Thr | Gln |
| | 1010 | | | | 1015 | | | | 1020 | |

Leu Val Asp Arg Thr Arg Ile Val Ile Val Pro Ser Leu Asn Pro
    1025                1030                1035

Asp Gly Arg Glu Arg Ala Gln Glu Lys Asp Cys Thr Ser Lys Ile
    1040                1045                1050

Gly Gln Thr Asn Ala Arg Gly Lys Asp Leu Asp Thr Asp Phe Thr
    1055                1060                1065

Asn Asn Ala Ser Gln Pro Glu Thr Lys Ala Ile Ile Glu Asn Leu
    1070                1075                1080

Ile Gln Lys Gln Asp Phe Ser Leu Ser Val Ala Leu Asp Gly Gly
    1085                1090                1095

Ser Met Leu Val Thr Tyr Pro Tyr Asp Lys Pro Val Gln Thr Val
    1100                1105                1110

Glu Asn Lys Glu Thr Leu Lys His Leu Ala Ser Leu Tyr Ala Asn
    1115                1120                1125

Asn His Pro Ser Met His Met Gly Gln Pro Ser Cys Pro Asn Lys
    1130                1135                1140

Ser Asp Glu Asn Ile Pro Gly Gly Val Met Arg Gly Ala Glu Trp
    1145                1150                1155

His Ser His Leu Gly Ser Met Lys Asp Tyr Ser Val Thr Tyr Gly
    1160                1165                1170

His Cys Pro Glu Ile Thr Val Tyr Thr Ser Cys Cys Tyr Phe Pro
    1175                1180                1185

Ser Ala Ala Arg Leu Pro Ser Leu Trp Ala Asp Asn Lys Arg Ser
    1190                1195                1200

Leu Leu Ser Met Leu Val Glu Val His Lys Gly Val His Gly Phe
    1205                1210                1215

Val Lys Asp Lys Thr Gly Lys Pro Ile Ser Lys Ala Val Ile Val
    1220                1225                1230

Leu Asn Glu Gly Ile Lys Val Gln Thr Lys Glu Gly Gly Tyr Phe
    1235                1240                1245

His Val Leu Leu Ala Pro Gly Val His Asn Ile Ile Ala Ile Ala
    1250                1255                1260

Asp Gly Tyr Gln Gln Gln His Ser Gln Val Phe Val His His Asp
    1265                1270                1275

Ala Ala Ser Ser Val Val Ile Val Phe Asp Thr Asp Asn Arg Ile
    1280                1285                1290

Phe Gly Leu Pro Arg Glu Leu Val Val Thr Val Ser Gly Ala Thr
    1295                1300                1305

Met Ser Ala Leu Ile Leu Thr Ala Cys Ile Ile Trp Cys Ile Cys
    1310                1315                1320

Ser Ile Lys Ser Asn Arg His Lys Asp Gly Phe His Arg Leu Arg
    1325                1330                1335

Gln His His Asp Glu Tyr Glu Asp Glu Ile Arg Met Met Ser Thr
    1340                1345                1350

Gly Ser Lys Lys Ser Leu Leu Ser His Glu Phe Gln Asp Glu Thr
    1355                1360                1365

Asp Thr Glu Glu Glu Thr Leu Tyr Ser Ser Lys His
    1370                1375                1380

<210> SEQ ID NO 2
<211> LENGTH: 114102
<212> TYPE: DNA

<213> ORGANISM: Homo sapiens

<400> SEQUENCE: 2

```
gaattcatta ggagctggct gccctgagcc gcagaaaaaa tattagtatt tatatttatt        60
tttctttaaa agaattaaac tttactgatg ccctatatat caactgatgc tggaagccac       120
atttgtctga acatgagtca agtgtcataa atcataagag agatctccca agaggaattt       180
gtgtgctgta gggtgtcatt aggctatttt tataaataaa ataaacaaaa aacacaagac       240
ctttaaactt tagatagtag aatcttgggt ggcaggttat ctcacttggt tagagcccag       300
tgttaataaa tcacagagtc cttataatac tgtaaagtga gttgaagagt gaccatcaaa       360
atcaattgta tcaaatagga ttatgggcca ttgaggggta aaggacttaa aagaattgtc       420
aatttaaaaa gatgaactgt gaactgcaca attttttctct tacaaaagag ctagtgttca       480
aaaatttctg accttttctg tgatgacaaa tgaatttaaa aactgggcta ccaggagaaa       540
ttacaataat caatcaacta attaataata aaacaattac aataataagc acatttaatt       600
aatatcttta agaaaaaaaa tggtgtttaa cagtgaatga aaagtcactg ttttgggggg       660
ccaaggcagg aggatcgttt gagtccagga gtttcagacc agccccggca acatagtaag       720
acctcatctc tacaaaaaaa ttaaagatta gctgggcctg gtggtatgtg cctgtagtcc       780
cagctactta ggaagctgag gcaggaggat cacttgagcc caggagtttg aggttacagt       840
ttgagtgcag cagccgagct atgatcacac acagctccag gtatgattgg gctactgcac       900
tccagcctgg gtgacagaga gagtttgtct caaaaagcaa agaaaagaa tagaaaagta       960
actgctcttg caaagaaact cttttttttaa ttaagaaagc attttgaaaa tggatgtctg      1020
gaagtcaaat tgtctgtgtt tgcagacgac atgattgtat atttagaaaa ccctgttgtc      1080
tcagctcaaa atctccttaa gctgataagc aacttcagca aaaatcacaa gcattcctat      1140
acaccaataa gagacaaaca gagagctaaa tcatgagtga gctcccattc acaattgcga      1200
cattgttttt ttattcctga aaatgatata actttatcat tacctatgaa acatttatac      1260
ctgcatgctt tacaaaaaac ttggaaagag tcttttaatc tattaatatt ccagacatag      1320
atttacaata cttttcaata gcttgcaaaa ataactcttg gacatcagta gatttattgg      1380
ctgaatttca attaaacttt gtatagctgc tggatagaaa tgaatattag gatttagcaa      1440
tgtgtttgtg gtgcatttgg cattgtgtaa atttgagact atatttctca gctatgatgg      1500
caattaaaac acgttttcaa aataaagtta gaaacacact tgtgaatcat ttcatcacaa      1560
attgttaagc caatttttt taaaacagtg gaatttactc aattatagtg agaacaaaaa      1620
tgttttttgta cctcaaatat ataatataaa aatttaaatt aaaaatattc atttcttctt      1680
tatctccttt taatttctat acttgtgtac atttataata tatatatgtt ataggtggac      1740
atcatttaga aataatatat aatatacatt tatattaata tatacaatat attaatatgt      1800
aatacacatg tatatatgta atatatataata cacatgtata tgtgtaatat ataatacaca      1860
tgtatataat acacatgtat atgtgtaata tatacatagt cataggtgga catcgtttag      1920
aaataaataa attgggctgg gcgcggtggc tcatgcctgt gatcccagca ctttgggagg      1980
ccaaggtagg cagatcgctt gtgcctaaga gtttgagacc agcctgggaa acatgtcgag      2040
accccatctc taaaaaaaat acaaaaatta gctgagtgtg gtggcacatg cctgtagtct      2100
cagctacata ggaggctaag gccggaggat aacctgagca tggggaggtc aaggcttcag      2160
tgagccatga tcgtggtact acactccagc ctgggtgaca gagtaagact cgatctcaaa      2220
aatacaatac aatacaatac aataaattaa aatgaatata ctagagattc atgctcaagc      2280
```

```
atttgtattg atacggagtg tttcaaaag ggttggaac cactgctgta ggaagacagg    2340
tctgagccta tgtatgagat aaagaacag aaacgacaaa aagatgagag acagaaggc    2400 tagtcagtta cttctgcaat acgatattcc aggccggtgt taataagagg ctgaattaag   2460
gtggtgacat tttcaatgga aaggaacaga cttaatggaa tgagataatg agaagacgga   2520
agtaataaat gttgacaacc aatgacacat agaaagcagg ggagaaggaa gtgtcagtaa   2580
ctgaattgag agaaagacaa agttattgag gaataaaaca atgaattttg ttttaaatat   2640
gttgaacttt agtgccttgg gaacattaag tgaaaggacc tatggaccag ttgaaaaaaa   2700
gaaactggtg ctggcttcag cagcacatac actaaaattg gaatgatgca gaaattatca   2760
tggcccctgt acaaggatga catgcaaatt cgtgaaggct tctgtgtttc tttttttttt   2820
taaagaaaaa actggatgac aacggctaac aattacttt tagagaagtt catgtgtttt     2880
gcaatctaac gtacattact gtaaagataa catgacttcg tggaaaccaa cagccttgac   2940
ttcttaaaat atgaacacct tttggaggca tccacaactt gttttccccc ccaggacttc   3000
ccactgtagc agaagacaaa aagagagag aatacagtgg attaatatgt ggccattgct    3060
ttgggaaact caggttccga acccactcta ccattttgta gtaatgaaac tctggagatt   3120
tatttaacac ttctaaggtt tagtcccctt attgttaaat aatggcataa taatacttat   3180
tttatatact tattgtgaga attaaatgag caaatatatg caaagtgctt atgtccttgc   3240
cttgtatagt taagcattaa ataaaaaata gttctaatta ttatctattc actatagctc   3300
ttggaaaata aattgactac tatattgtct ctgatcttag cctactatat catattctac   3360
atattcacat gtgtgtgctc atacatacac caaaaaataa agatcattcg caaagttttt   3420
agtatttgaa acctagactg agaaagaatg ttaaaattct catatttgga tcaaacctat   3480
aataatatga tccttacatc tacatagaat ttttcagtca cagaaattat atacattcat   3540
aaagcacaac agaaatccac catatctata cttggtgtcc tttaggcaga gagcagagca   3600
aagtggagaa taaaaatatt caagaaaaa aggtatactt tcctgaaatg aagaacagaa    3660
gctacaaatt taaagatac aggccgggtg tggtggctca cacctgtaat cccagcactt     3720 tgagggccg aggcgggcgg atcacgaggt cagagatcg agaccatcct ggttaacaca      3780
gtgaaaccct gtctctacta aatatacaaa aaaaattagc caggcatggt ggtgggcacc   3840
tgtagtccca gctactaggg aggctgaggc aggagaatgg catgaaccca ggaggtggag   3900
cttgcggtga gccgagatcg caccactgca ctccagcctg ggcaacagag cgagactctg   3960
tctcaaaaaa aaaaaaaaa aagatacact gtgtagtaga aaaaattagc atagcggaat    4020
agaactgtga cacagctaca tgaagtgact aaacttcatg aactaagtgc ataatcttat   4080
tggtatctag gtagaaaaca caagccactt gtaataggaa gatgtaaagc tgagctcaaa   4140
ctcattcaca ataatcatcc atgccaaaag attatagaac aatgtttaca gagttctaag   4200
gagaaaccag tgtgacccaa gaattttata cccagctaaa tttccacttg tgtataaggc   4260
catcaaaaac tagtctcaaa tgacaaaggc ttacttcagg taaaacacat ataaacactg   4320
gttgaaaaag ctacctgatg ataaagtcta gccaattaag acatttctag gcttggcaca   4380
gtggctcgag cctgtaatcc tagcactttg ggaggccgag ctgggcagat cacctgaggc   4440
caggagttcg tgaccagcct ggccaacata ggtgaaaccc tgtctctatt aaaatacaaa   4500
aattagctgg gtgcagtggc atgtgcctgt aatcccaact acttgggagg ttgaggcagg   4560
agaattgctt gagcccagga ggtggaggtt gcagtgagcc aagatcgcac cactgcactc   4620
cagcctgggc aacagagcaa gactctgtct caaaaaaaaa aaagaaaaa aaaaagact    4680
```

```
tttccgaatg aaaaactaga aaatgggaac tatttaataa ggctaatcat gaagtctgaa    4740
tctatataaa tctagaaata aggtaaaaca actatagata ttacaaaata ggacctacat    4800
atgtgaataa ggaagcagag ctgccgagcg aagaggtgga catctgggtg gtggtgtgac    4860
ccagtacagg gtgtcagagc ctaagagggc atcatccact cagggtgca gcccagcata    4920
gggtgccaga atctaagcag ggtacctatg ttggagggct gcttgagtgc aaggagtgcc    4980
tgcatagggt gagacaggtg tccatgtagg gtagtagtgg tggctcagtg cagagtgtca    5040
gagtctgagc caaatgagga aggtatccat gcatgagggc gacctgttga tgctatcaga    5100
gctcaagcaa gataagaagg gcatccacat gggagcatag gctggcgcag agtaaaacct    5160
tgagcagcac atagagggac taccgatgca gggtaaaaag gttttcgta cttatttgcc    5220
atttttttct gaaagtatgt gattttctt aaaaagtgcc ctaacataga tttccccgat    5280
attacagata attacctgtg gggaaatgac atagaaaata tatttaaagt attatttgat    5340
gtatatgtat acagatacta ggagtatcac attaatcaca tgacactgat tcctttcaac    5400
tatcttgctt ttctaataca taaataattt tgcatgtgtc attaagaaac tttctcatgc    5460
tgatttatta aagcatttta atgctactta agaatatga agtgtggccg ggcgtggtgg    5520
ttcacgcctg taatcccagc actttggcag gccaaggcag gtggatcaca aggtcaagag    5580
atcaagtcca tcctgaccaa catggtgaaa ccccgtctat gctaaaaata caaaaattag    5640
ctgggcgtgg tggtgcatgc ctgtagccca gctacttggg aggctgaggc aggagaatca    5700
cttgaacccg ggaggttgag gttgcagtga gctgagatcg tgccactgca ctccagcctg    5760
gagacagagc gagactccat ctaaaaaaaa aaaagaata tgaaagtgtg atgctgagtg    5820
cggtggttca cacctgtaat cccagcactt tgagaggtga aggtaagagg atcacttgag    5880
ccaaggagtt tgaggctgca gtgagctata atcacagcac tacactccag cctggatgac    5940
agagcaatac cttgtctctt tctcttaatt tagaaaaaaa aaaaaaaaa ggaagtgggc    6000
agactgcaag taaaccctga gaactcctag atcacctcag tttgcagcac ccattcacct    6060
ctttcctcac cactgcctaa gaaggcacat gaagcttagt cactgtgcag actctcaaaa    6120
ctttctggaa cttcatgcaa aggttaagcc ttggaaccaa ctctgaattt ccttgtggtt    6180
tcaaacttgt cacattttct tctcaccttg tcaccaccca cacagactca gcctcctgga    6240
tgcatcacgc ttgggttgct tcacttcctg gctcctggta agccacaatt gcaagagcta    6300
ttgctggtaa aactggtgac ccattacagg cacacaaata gaacatagg tgcaggggag    6360
ccacaagtgc actatctgaa tgtgtcaggg tgagaacatt atgtttcctc agctctcact    6420
catcctctgg tggagaggac tctttggtct tcagtcttcc aataactgtc tatagaatat    6480
ttttgcatgc tattcatcta tacctgaatg caagcatgct ttcagtacag aagaaatgtc    6540
ataggtca gaataatgtt tcaatgggct cagggttttt gtccccggtt gtcctatcaa    6600
cccattttgt actatctact ggtagtggtt ccaaattctg atctccgaac tggtgatgat    6660
atggaaataa ttttttcatt attattaatc tgtcatgaaa tttttagaaat aagaataatg    6720
tgggagaaca ggtctaaatt tcattggta aaaaaggaac tcttttttct ttttttttga    6780
gacagggtct cactctgttg cccagactgg agtgcagtga cacaatcatg gctcactgca    6840
gcctcaactt cctgggctca ggtgatcctc ccactccagt ctctcaggtg ctaggactg    6900
taggcatggg ccaccatgcc tggctaattt tattttattt tattttattt tattttattt    6960
agtattttt tgtagagatg gtgttttgcc atgttcccca ggctggtctc aagttcctgg    7020
gctcaagcaa tctgcccact tcccttggcc ttgcaaagtg tttctttcc ttttttttt    7080
```

```
tttttttttt tttttgagat ggagtcttgc actgttgccc aggctggagt gcagtggcgt     7140
gatctcagct cactgcaacc tccacctccc gggttcaagc gattctccta tctcagcctc     7200
ccaagtagct gagattacag gtgcctgcca ccacacccag ctaattttt  gtattttag      7260
tagagacggg gtttcactat gttggtcagg ctggtcttga actcctgacc ttgtgattcg     7320
cccacctcag cctcccaaag tgctgggata caggtgtga  gccactgtgc ccgtcccaag     7380
aactcttctt tatcctgaga ctatgtcctt gtattttag  tttcaaatat agctctcctt    7440
tcggggccag gtgtagtggc tcacgcctgt aatcctgtaa tcacgcctct aatcctagca     7500
ctttaggagg ccgaggcagg cggataactt ttgtccacca atctcagcct cccaaagtgc     7560
taggattaca ggcgtgaacc accgcgcctg actattcttc acatcttgaa gcacagctac     7620
cacagctgac ataatagtcc aacaattttg tcagcaaata ggccaatcct ttttcaagaa     7680
tatcaattcc tcccctttt  gccacccaac agccttccat tcattaacaa ccacactggc    7740
taccagaaat tgggaaagag aagagcagcc acagtagcca gaaagttaag aattgtcctc     7800
tcctgagtcc tcacctcttc aaaggcagag gaatgtttat agctgggtca tccctgaagg     7860
cactagcaaa gcaggaatac caggatgaga gtgacagtga gagaaacact catctttaat     7920
taacgaaatc tgaattttgt aatccccaaa tctagaaaga agctatttta atgttagcat     7980
acatgtaagg tttatgtcct cttgaaaaat caaatttaat tttgagtttt cttttgggac     8040
aaggagaccc tcatcttttt agtgcttaag gtctctaagg ctctctctct ctctctctct     8100
cccttttct ttttttaatt gagacacagt cttggtctgt cacccaggct ggagtgcact      8160
ggcatgatct cagttcactg caacctctgc ctcccgggct caagtgattg tcctgcctca     8220
gccacctgag tagctgggac tacaggcgtg tgtcaccatg cccggctaat ttttgtattt     8280
ttagtagaga cagggtttct cctgttggcc aggttggtct cgaactcctg gcctcaagtt     8340
acctgcccgc ctcagcctcc caaagtgctg ggattacagg tgtgagccac cgcactcagc     8400
aaggctcttc tttatctggc cttaattgtg ttttcttcac ttctgcatgc ctgcagcctt     8460
gtactggcat aaagaccatg cttaatcaag gtctgttgaa ttaaccaata aatgaacaaa     8520
agaccttgga gagtagaatc aagtgctggg aaagggacaa agatagggaa tggggagcag     8580
ggtggcattg gaaagcacca taaaagaact tgcctggaac atctgcttca gatttgctgt     8640
aatttctacc agttttgtct tatctttggt tacactagtt caccctcttt tgtgtggctt     8700
cattgttctt tcctttactt gagtgtttcc cttgagctag taatttttc  ttatgaaggt    8760
cttttgcaga cctactctcc tcttctatgt ccctcccact taggatttcc cagggagctt     8820
tggttcgtat gtgggcttgc agtatttggg tagctgcttt ctccagcact ataatttccc     8880
ttgtaccatt tttttcaccc gggcctataa cagagagatg gctgcagact gttcccatga     8940
atagcatcaa tctcttcacc ttctggagct tcagcttgta ctcttaagat ggaatccagc     9000
tggctgggta taaatgtgct ttgtttgtgc caattcagtc tcggcaagtg ttttcatcaa     9060
aattagaggc tgaaattgct ggctgccagg gcattcctgg taactgaaca ttttctggt     9120
tgaagatggg agtcatgccc taggcccttt atgcaagagt gcaccatccc aatttcttgc     9180
tgtttttact ggaggatgtc ttcagatctg gcacaccata ctacatctga gcaagacagt     9240
atttggtccc attcaatttt gttgctagaa tctagggcca gcctttgtct aacctgtaaa     9300
ataggtataa ggtagaaccc tggtgaaact aagctatatt gccctgtctc agcccagatt     9360
cacatccaaa agaaatcaaa gaccaactcc tataaaagcc ttgaaaagta agtatgtaa      9420
atcttcacca ttcattattc acctgaagtg atcttgaggg catctaggag aaagttgctg     9480
```

```
agctcattat agagtacacc gtcactctac taaagtcgca cacttctcaa gagctgcttc    9540
cacccctcata taagctcatt attaccctct tccctctcag gggatgccaa tattttttt    9600
atttgaggca aaattcacat aacataaaat taatcatttt aaagtgcaca attggctggg    9660
catggtggct tatgcctata atccccgcac tttggggaggc tgaggtgggc cgatgtcttg   9720
agcctaggag tttgagacca gccacgggca acatggcgaa acccatctc cacaaaaaat    9780
acaaaaatta gccaggcata tggtgtgtgc ctgtagtccc agctacttgg gaggctgagg   9840
tgggaggatt tcttgagccg ggaggtcaa ggatgcagtg gcatttagta tattcacaag   9900
gttgtacaac tattggttct atctagttcc ctaatattgt cattacccaa aaggaaaccc   9960
tgtacccatt aagcagccat tcccccattc cccctgcac cagtatattt tgttttttta  10020
atatattttt aaaaaaacaa caaaacagag acagggtctc agtatgttgc ccaggctggt  10080
cttgaactcc tgagctcaaa aaatcctttc acctcagcct tccaaggtgc tgggattaca  10140
ggcgtgagtc acctctcctg gccctcttcc agtaatttta aaggtcccct aggctattca  10200
aaagggtagc cagggccagg cacgatggct catgcctgta atcacagtac tttgggaggc  10260
caagacgggc agatccctg aggtcaggag ttcgagacca gcctgatcaa catggtgaaa  10320
caccatttct actaaaaata caaaaattag ctgggggtgt actcctgtaa tcccagctac  10380
tcaggaggct gaggcaggag aatcacttga acctgggagg tggaggttgc agtgagccaa  10440
gatcatgcca ctgcactcca gcctgcacga tggagcgaga cttcatctca aaacaaaaaa  10500
caaaacaaga aaaacaaaag ggcagccagg gctgagaacc gttagcgtca tgcgatctca  10560
tttcccctat gctctcccta cttagaatgc cactgtttat ccaggtggcc aagcagctaa  10620
atcaaagatt ctcttttagaa atgtgggggc aagttctgtt tttttgcccc agtcacacag  10680
gtaccattgg ctttggcaac ccaactcctc ctctttcagt attttctcc atcatctgca  10740
cttcattctc actggccttt gctctccaag aagcctgtta acaaatcct ctctaaggta  10800
agaattccca ctgtttctcc ccattcctta agggtcagct gatctcaaga ttccttgatg  10860
tttgccttt aattgacgga aaagcctttc agactcagag aacccctctc taatggtgca  10920
ttttaggcac taaacagatg gggagaggaa ggaaatgttt taggaatgaa ggaaactttt  10980
ccagttactc ttcacctaag aatgacacat atactgaaca aaggatgggg tttgcagttg  11040
gaagatagcg tggtcttggg caccagtaac ctaatgtctc agagcctgta tccttacctg  11100
taaaattatg ataatattga cccggaagag ttatatttcc ataagttgca gccataggta  11160
ctgagtctgt tgaaaatga atttaataaa aggatattgg ttggttcaca gaattgctag  11220
gtgagttggc aaaatcaggg gttataaaca gaaaggaaga atgccgcaaa gcaagcagca  11280
gaacttagga gaccgctcta ctgtcaccaa gtaccagctg ctgcagctca tcctgccagc  11340
accactggcg ctgggggctg ggtgttctgt ttgctctgtt gccccagaag ctatacattg  11400
ctgccatttc ccccaccaca gctagaaaga attatccaca gcctctgctt ctttgtttca  11460
ctagctccca attcaaagtc tgtcacaggt ttgtttgctt ggttaaagct agactatgtg  11520
tctcatgtcc tgtgagaaca agcacctggc attttcagcc tgcagagtgg gagaaggccc  11580
tgccttccac cacgactcct aaggtgggga gggttcgccg gatgaaggga gggagttcag  11640
acaccgggca tccaaaaata aagacaaagg ttccttttcc aattgtgggg gttagtgaga  11700
caaagtgtat gaaaagcata aacgctgaag tgccatgttg gtattgctta gcaacacttt  11760
gttcacactg tcacgtattg cactgcattt cctttttttc cctccctctct tcttctttct  11820
gtctcatacg cagttatgtg ccctccagcc caggacaggg cacgctcata aatgccgaat  11880
```

```
gaatacaata ttctgctgcc tttgcttgtt tgatgaagca ggttggtgtt tattggtttg    11940
tccccgttgc caaaggccct gattttcatt tggggatcca tgtagttcat gggaatcaga    12000
ttccattccc agcaccagca atagggttta tatactaaac taagtcgatc agcatattcc    12060
atatccctgg ccatagcaat tggttcagga gcaggcaggt gacctaagga gttccaatct    12120
gagttacgct tggcaatttt gcaaggacaa gaacatcctc tgttttcttg ctgaactatg    12180
aatgagaatg catgtagcat tgggagtttc tggcagccct cttggaatca ccaggggagt    12240
cagacttaga atgaagtgaa cattgtagaa ggcagggcca caggacaaaa agaaaccagg    12300
tgttttgtgc ccatttagcc aaaatggaca caggaaaaag ctatgcccaa atccagactt    12360
ctcctttgga cttctcagtt atatgagcca ataaattcca tttattattt aagctagaat    12420
gagtcaggtt ttctgattca tacaactgaa agtatctgat acctgctttg ctccttccct    12480
gcctcatgat aatagaatta ctgtttattc agtgctggct aatagagagt cttttggaaa    12540
tacagatcaa aattactatc atgttctcac aattgggaaa cagcataatc tatgccctag    12600
aaacagaact aactaaaatt taaaatagaa tagccctacc taacctcagc caaattttaa    12660
aagaaatttc agtaaacatc ttttattatt ctttggccta gaaagatgaa acatcaagg    12720 aagtaagaga aaactctctt aaacaaacaa aattaaacaa aacaagaaca ctacaccagg    12780
ccaagcacag tggctcatgc ctgtaatccc agcacttagg gaggtagaga caggaggact    12840
gtgtgagccc aggagtttga aacagttgg ggcaacaaag tgagacccag tctccacaaa    12900
aaattaaaaa aattagccag gcatggtggt gcacgcctgt ggtcccagct acaagggagg    12960
cgaggcagga ggattgcttg agctcaggag gttgaagtta cagtgagtcg tgttcatgcc    13020
actgcactcc agcctggctg ataagagtga actttgtct gattgtctga ttaaaaaaaa    13080
aaagtccacc ccctacccta aataacacct ccccacacct aaacacctaa accaaaacaa    13140
acaacaaaac ataatgcaaa gaaagcaaaa tgtattctat ctaacctata gggggaagta    13200
ctatggagtg atatcctacc tggctgtcct aaggcaggtt cctaaaagca tagcctgaga    13260
cagggatgct tacgtaagtg atttattgaa gagtgccctt gggagaaacc tgaaagggat    13320
taagggaagc agatcagaag aagatgctga gcaagaacga aaaaagaac tcttacctca    13380 gcctgattct gcagaaagct ctgcctggag cataaattgc tccaaagttt gtctcatcca    13440
gaggcaaggg ggcctgtata ccagtaggat gaccctggaa gaggtggggt ggaggcagtg    13500
tgtgtaattt cttaggcatt tctgggcaaa gtagctcctg tcagccaagg taaatcttcc    13560
cacaaagatg cagatgtaag taagcatcag ctaggagatg ggtgcacgag cctggtagag    13620
agaatccggg cagacaacca acagcacttg taagaactga tatggccaaa ggttctcttg    13680
aaaattccct caatttgccc attttgagac tttatttaaa aaaatttca gaaaatcatt    13740 cattattatt attattattt tgctgcttgt aacacattag caaatttatg aaaattctaa    13800
ttgcatgcca tttcatgttt ccatcatcct tgtcttctag ggacagcttc ttgtcagtgc    13860
ctctaattct cctttaagtt tatgtgtctc tggctgggtg gtggctcaca cctgtaatcc    13920
cagcactttg ggaggccaaa gcaggcgatc actcaaggcc aggagctcga gaccagcctg    13980
gccaacatgg cgaaaccatg tctgtaccag aaaaatacaa aaagtagcca gatgtggtgg    14040
cgtgtgccta taaccccagc tacttgtgag gctgaggtgg gaaaattgct tgaacccagg    14100
aggtggaggt tgcagtaagc caagactgcg ccactgcact ccagcctggg tgacacagca    14160
aaactccatc tcggaaaaaa caaaacaac aacaaaaaaa aaaacagtta atatgtctct    14220
atggccctca gttaattctt caatttcttc ctccgcaggt actaaccaca ttactgttca    14280
```

```
cctgcatatt gcattttatt tttgttaatg gtcagtaaac ctttaaagtt acttacacat   14340
cctttctgca gttttaaacc aacatgtaca tctggttttg gctttgtttt tttgttttg    14400 tttttgagac agagttttgc tcgtcaccca ggttggagtg caacggtgcg atctcagctc   14460
actgcaacct ctgcctcttg ggttcaagcg attctcctgc ctcagcctcc cgagtaactg   14520
ggattacaag ccccagccaa catgcccgac taatttttt gtatttttag tagagacggg    14580
gtttcatcat gttggccagg ctggtcttga cacctgacc tcacgtgatc cacctgcctt    14640
ggcctcacaa aatgctggca ttacaggcat gagccactgt gccaggccct acatctgttt   14700
taagtttagt tgttactttc attctctcac tttttctcac tgttagttag atgtgcgcac   14760
aatgtacata taccctagag tgagttaagt gcactgaacc ccagcatgtg atggcaggaa   14820
ctctggacag gttttgcaca cagcttaagt tcccagctgt tccatgtcct gctatttgac   14880
ttgcttgagc tggtggagct taaaacaaga atctttctag gctgtcctga tactcttcag   14940
agttgtgagc attgtgtgag ataacatacc ggaaggcaca cagaaatata aggtgatagt   15000
attatgcaca ctgtgattga tatgatattt atatttcaaa ttccaaattt gctttcagtt   15060
ggttgccttt tgggttctga gatgacttca tctcttacca atgttcctg ggctataagt    15120 tgctaggatt tgactttctc ttgcagaggt gacacacagc gagtagtcac ttgtcaaggt   15180
gagtcaacac tagggggaac caggcattga gcaaattgaa gtggaggttt tcagtgatgc   15240
catctctctt cttccttctc tatgttcatc ttctcaggag cctccatgc cctcagggtg     15300 gccgctggat tttcagagcc caattcactg ggctgtaact acattttcca tgaactcaga   15360
cagacagcct catcaacaaa taatgaact aaacaaagcc aaaaaccttc tgttctatgt     15420
cccattagct ttcaggtcta gatgacatgt tagaaaactg ctgggctcta ttaagtgtca   15480
atggctggaa actgttctta ccctccattt ctctctccca ctctttgaga tgattatttc   15540
acaccttcct ctcttttctc aaacctccaa cacctactcc aacatcctta cactcagcta   15600
gtggccttgc tttccatttc attaagaaaa taaaagcaat cagcagagaa ccttctccca   15660
atacctcacc tacccactta attgtaccta tgcccatata ttctgccttc ccatttgtga   15720
ctactgaagt gtctgtattt cgacctaaga cccatccctc cactggtata ttagatacac   15780
tatcccttcc caactactca tactcaaagc catggctcca gcaattctcc cttctctcta   15840
atgggtcatc acatttttccc tctttactag atcattccta tcagtataca aacaacctat   15900
aatttctccc atgtttaaaa aacaaagacc tggagcggtg gcttgcacct gtattcccag   15960
cactttggga ggctgaagca ggcagattgc ttgatcccag gagtttgaga ccagcctggg   16020
caacacagca aaaccctgtt gtcagatcct ggggtctggg tccagcctat gcggaatcca   16080
agggcagtgg gtggatgggc agaaagaaca cttgggggc tgtaggcagg tgaaagatga    16140
ttttattcag cagcacctct catcaacagc tttctcatac tgtccacctt tatctcggct   16200
gtctgctctg gctctgcggc tcctgccacc ctcacaatgc agttgcatgg ctggctctcc   16260
cttgccttca gggtcagcag cttaacttct tctctctctg ggctccggcg cgagccatgc   16320
tgtggctccc atctgtctgt ctgcaggatg gacagctctg gttctctctc tctttctctg   16380 ggaccagtg tgcccaccat gttaagccat gttgagccga gccgagcccc aagagccatg    16440
tctgtcatgc acagtgtcaa cagggcagtt atatcttta cagacaacag tggctcaggg     16500
ccatgtatga acttacacaa acaggttaca tagcaagtgg aggggtgccc ttgcgagcca   16560
aactctccaa gtcatgcagg cctggatatc cgccttggcc tattccttga ccaaagcaca   16620
tccatgtacc ttacacctgt ctctacaaaa aatacaaaaa ttagccaggt gtggtagcat   16680
```

```
gtccctgtag tcccaactac ttgggaggct gaggcaagag gatcgcttga gcctgagagg   16740
tcgaggctgc agtgagctgt gattgtgcca ctgcactcca gcctgggcaa cagagtgaga   16800
cctcgtctta aacaccaaca aacacgacaa caacaaaact gttcccatta tctagacata   16860
cctgccgctg gatttcatac aggcatctca aacctaaaag ttcccaaaat caacacctaa   16920
tctcttttcc cacacactcc aagcccctcc atttagcatc ttttctcctg ccttctttgt   16980
cttggataat ggcaaagcca cctacctggt caccctcact agctcatgaa gtcatctttt   17040
acttcttctt ccctttacc cataaagttg ctaaatcttg tcaatccaac aacctaaaca   17100
tctctaattt atcttctttt tatcctcact gaacttgcca gaattagctc ttgcctggat   17160
agcagctatc ccttagcctt gcccaaatgg ttcctggaat tttcttgcta aaacacaggt   17220
gcgatccaca ccattcctcc tcacaaacag ctctgtaagt tttccatttg ctttggaata   17280
aagcaaaacc ccattagtgt ggtattcaaa gccttcatct acttctagtc tttgcaggca   17340
tggcttctgc tgctcttcct aacacatctt gtattccagc caccagtcac gaaatccctc   17400
tctgtgcatc tatccttgct ggtctctctg cctggagtgc tcttttctcc attttacca   17460 tttgagaatt tctattatta aaacaatag aaataacggt gatttctgaa cgcttgttat   17520
atgccaagta ttatattaaa tgttatgtat gtattatttc ttttaatttt cagagaaatg   17580
aagtaacttg ccctggttac aatggctgaa aagggactga tccaggattt gaacttggtt   17640
ctgctgttga agagcatgat caagcagtat tggtgacgtt ttctctgact cttcattatt   17700 tttatttta atttctttta ttatttatt ttgtattttt agtagagacg gggtttcacc   17760
atgttgaccg ggctggtctt gaactcctga cctcaggtga cctgcccgcc tcggcctccc   17820
aaagtgctgg gattacaggc ttgagccacc gagggaggtg actcttcatt ataatggctt   17880
ttgtgtgttc caaaaacagg ttttttgtttt ttgttttttt aagcttacta tatagaaaca   17940
gttttattac agaatttaag cacacagact ctgaagtcac actccccagg tttgagtctt   18000
ggatctgtgg cttgccagct gtgtgacctc atgtctcctc tctttatctt tgaaatggga   18060
atgataatag caccagcctc ataggactgt tgtgaagatg aaatgagtca accaatgtaa   18120
agggttttgc acagtgcctg ttatgtaact cttgtccagc agacacatcc agtcctgtgt   18180
tgtgtctatg ttctgtgtcc cttcctagat tctgtcctct gggaggggag agatcccctt   18240
cattcatttt ccaatcctcc tgtacctggc acaacagacc tttcgccaga ttgggtgctc   18300
cacaaacatt tgtcaaattg aatttgtaaa tctgcaggtg tttgtgctgg acaatgagac   18360
acttacaagt tcccggtcta tgctatgctt taattaccta cgaatcttgt gaagaaaatg   18420
gttcttgaat caggctggtc atctaaaagc ttttgccctg ttttaaaaa atccacgtca   18480 attctttgtc atttcttggt gctagaaaca tttcaaatct ctttgagcta aatgaggtga   18540
tggctatcca gaatgtcctg gtttgatcat aatatattgt atgcatgtat caaaatatca   18600
aatgtatccc ataaatatgt acaattatca tgtatcaaat acaaaaatta aaaaaaaaa   18660 tccaagtcat tgccactctg cttctgtgaa caggaagcct ttttaccttc aagcctttcc   18720
caagtccctt ccatttgtaa ggccacacct tttccttggg gaagaggaa agaaacacct   18780 gtcataaggt tcaagacttc tcagacacaa ttggaggtat tcagctgtag gtaaacacaa   18840
acctgtaggt aaacacaaaa gtgactgagg tccagagctt tgggtttcac ttataaccat   18900
aagcaactgt gtacctgcta aggaagaagg ctgcagacct gaaagaggcc cacggaaggc   18960
ctggggattt ctgagaggac accggctcaa gttacattcc catattattt caccaccctc   19020
atgcttgttt atttacattt ccaggctgcc tctctaggcg aggctgcagg agtgaagggg   19080
```

```
ctggaagagg tttcaaagga gagtgaacgt ggtagaaaag gaaatatttg attagaagtt      19140
aacatgtcct ctggggcttc tttgacttgg attactgtaa aagtgcatgg tgtaatagtt      19200
gagcactccc gggaggtggt gggcggtctc tctgtacaga gttgtggctt tgtttctgat      19260
gagttgcagc tgctgtgcat aatgtagact agatcaaatg gggcatggag aagagccatt      19320
cacaggaccg gagtgacggt gctcgctctg atggcagaat actaaattaa tcatcttcac      19380
ctaaacctgt gctttctcct ggcctgtacc tcagtgaata cctgcaagtt gcttaggctg      19440
taacttgaag tcagcctaca atcctctttg tctccagatc ctgtccactt ccttttccga      19500
aggtctttca gatccatttc cttctttcca cctccactgg cactgccctc attcagagtc      19560
tcatcatgtc ttcctggatt gcagcttcct tccaggtctc tcagcctcaa gtcttaggcc      19620
tcccattcaa ttttccgtgt tactgtcaga ggaattttttc taaactagct taaaacccgt      19680
ctgtggttct ccatggcctt ccagatcaaa tgtgctccct gaagactggc ctgtgagccc      19740
cttcacacca gtaatcctga ccctgcatgc aattcccaga acacaaggca tttgttctca      19800
aatcctgcgg cttttctttgc ttgcttctcc tcctgcctgg gatccttccc atcctccatg      19860
gtttctctcc tccttttcctc ctcctcaagt tcagatattt ccctcacctg taccccctct      19920
gttgtagcat ttatcacaaa ctacactgaa tctcttgact gggcagaaga atgaattgtt      19980
tcccagcatc tagcttttgac ataaaagttg ctcaataaat acttgacgaa tgaatgaact      20040
ctattaaagt agggttcagt catagttcag ggaaggggcc ctgaaatagc tggctctgaa      20100
agaaggtaat gccggttatt gcgattatgt tgttagatgg gtagaatttc gcattcgatt      20160
aagggatagt tttgggtttc ttcaagctaa agaaactaaa gcctataaaa ggtgatttaa      20220
aagacctctt ctctagactt gatgaaacgc tgtaattgcc atctttggct gacactgagg      20280
agttcaggaa tgccaagcaa gtgtttccag aaatgtcaaa cctgctgttt taaaatatgt      20340
cattccaggg cacagttaaa tatacaactt gctccgatga ggtgggagaa gtgggccggt      20400
gagctgtgaa atgaaatctg cctaatgagg gtcgaggcca gcacacacag ggacctattt      20460
gcagtaaaac aacgtggggt gacgcctaag aaatagacaa cattaacaca aagggagcct      20520
actacgtagc acatttccgc taggcataaa agagacacct ttccagaaag caactctaaa      20580
aatgaatgca ccgcctagtg aggtgcgagc cttcctcccc acgaggcgtc ccgtgcaacc      20640
gcacgcggac agcggggctc cagcggaggc ggggtggatg cggagacaag gcgcctagga      20700
gactgggcta aggctttgag tgtccgaacg aagattcttt cgaacctatt gattttttct      20760
agtcttatga ttcttttcgaa cctttttgatt cttttccattc tcggttctaa gcattaaagc      20820
gcagctgaga aaggcagcaa caaagatggg aagagaacta gcaggagttc tcagagaaaa      20880
atgggtgata atttaggga gaagccataa agaagagact aagcgagaag cggagcacac      20940
gcagaagacg aaacaaggag gaggagaaga gaagaagaac cttggcgaag aagagagtg       21000 accaaactcg tcccggacgg gagaagggca ggcccgccca gagggaatcg gctgctttaa      21060
gggaagcccc gccccctggt ggtgacgctc caccaggccc gtccgcgatt ggctgcggcc      21120
agagggcgga atgggttgc taggcgagga ggggatccgg cggcccccg ccgcccggag        21180 cgctgagccg cggggagcgga gccggggtta gcggcgctgc tggaagatgg cgagcggccg     21240
ggacgagcgg ccgccttggc ggctagggcg gctcctgttg ctcatgtgcc tgctgctgct      21300
ggggagctcg gcccgggcgg ctcacatcaa gaaggcggag gcgactacca caactacgag      21360
cgcgggcgcc gaggcggccg agggccagtt cgaccgctac taccacgaag aggagttgga      21420
gtcggcgctg agggaggcgg cggccgcggg cctccccggc ctggcccgcc tctttagcat      21480
```

```
cggccgctcg gtggaaggcc ggccgctgtg ggtgcttcgc ctcaccgccg gcctggggtc    21540
gctaatccct gagggcgacg cggggcctga cgctgccggg cccgacgctg cggggccgct    21600
gctgcccggc cggccccagg tgaagctggt gggcaacatg catggcgacg agaccgtgtc    21660
gcgccaggtg ttgatctact tggcccgcga gctggcggcc ggctaccgcc gcggggaccc    21720
gcgcctggtc cgcctgctca acaccaccga cgtgtacctg ctgcccagcc tcaaccccga    21780
tggcttcgag cgtgcccgcg agggcgactg tggcttcggc gacggcggcc cgtccggggc    21840
cagcggccgc gacaatagtc gcggccgcga cctcaaccga agctttcccg accagtttag    21900
caccggcgaa ccccccgccc tggacgaggt gcccgaggtg cgcgccctca tcgagtggat    21960
ccgcaggaac aagtgagtgt tgcctgcccc ctccccgtcc gtgtgagcct caagggccg    22020 aggctggttc cggcacccag taggcgctca gacaatgctg gcataagggg tggcggtggt    22080
gaaggtgaag ggagacaccc tgtaacgggg acagggccca ggccgcgtag cctcccgtcc    22140
tgctaatcat caaagaattg cctcctagag gctgtcattt gttcaaggga tggctggagg    22200
ggacactcct ttctgacatt tctggtccct attcttacag gggcatagaa tatgagcgag    22260
aagagatctt aaggataacc taggtcagct cacacatttt atagataagc tgtcaatgtt    22320
gttatcttat atcaaaagtg cctaatgtta taggcgctgt gctaatttt tctgtgactg    22380 cagtatctca ctttattttg gccacaacct gatgtcatag acaccatcag ttttgcatac    22440
ggggaaattg agggtcagat tggttaactg atttacatag gagtgtggct gggacttaga    22500
attaggcaat ctgattcccg atagtcctct tagccacgga gggacactgg agcccaaaaa    22560
tggcagatga tattcccagg atcttcccct tgcctatttg acagaagctg attttctcc    22620 aatttttacc tctgactcag cttaagaaga tatggactta gctggagaac ttgcacagat    22680
ctgtgagccg cttcatttta gactctgaag ggtttgtgat gtcatttgtg caccttatta    22740
gcctgggcag aatggctaat ggtcacactt ctaatacaca ctttaagtgt tattaagcat    22800
tgcatgaggt ttaaaaaatt acaaagtaga agaaggagga cctcaagaaa ttagtataaa    22860
acaagagaat gttataaata tttatgaggt atgttggtgt acccagttaa actttacagg    22920
aattgttccc actggcaaga tgtgtgtggg ctgcaataac acggaccatc tctgtggaag    22980
aggtagagct tgagctatct ccagagatgg gcaggatttt cagcaaaaag gagaggaata    23040
aaataagagg gaactcactc cagatggcat agtgtctgaa gtgagcaggc atctcttccc    23100 ctttttctagc atcagctttt ccccattttt gtatcttcat aaggcttttg aagcaataac    23160
tgatcattcc atctggatta aaagaagatt tctgagggac tgctaagata aagaagtttc    23220
cctgcgggac ttggaatcat ttcttctaca agatttcagt catatataga agatctagaa    23280
aattcttgag tgttaggaca gttcctgagt cttttcgtct tctatctttt actttactcc    23340
tcttgataag ctctcttgta gatatataat ttcacataga ctttctggga ggatttttt    23400 ttcttttaaa tacgatcgtg tcatcacctc tgaacatctg cgtaagaaat atgactttga    23460
catacactta ttgacagagc tgtgatggcc agggcttttt ggagatgata caacaaatgc    23520
accgtttgca ttgcttaaat gtttaaaatg ctctgtcctt gcacctttaa aatgctgtga    23580
tccttgcagg gatgtaaatt ctgtgcctgg attttctttt tcagtattag ttgtgctgtg    23640
accaaatatg aaaataagct ttttcttggt gcaagtcgcc ttgaggctat acagagtcat    23700
tttggtctgt ggctgtggac taccctaatc atatctgttc ttcaaatatg taactctcat    23760
taatcaaaag ggaaagtagg tgatcatata tggtaaagag tacatccatc ctaactcagt    23820
cttcaagaat tcactcaaaa tgcgtactct gtgctattaa ccaataacaa aggacactga    23880
```

```
tatgtgaata aaattaaaaa cacaagcaca cacacaattt gatattgatg cctaaatata    23940
gtgtcaactt tatggatggg atattttaa atactcaaac attagtctgt atgggaaaac    24000
taccttttc agtgtatttt gtgaggtaaa ccatttgagt aatttcttga tatcctattc    24060
acccagctat attcgaatta gattttgtt gttatttcga atatgtaaaa ttttaaggct    24120
taatttcctc cagcttggga aaatgaagtt tattttcttt gtttcacttt atacttcatc    24180
caatggatgt tgagacaaat acttaagaaa atatataaaa aaattaactt tatcattcaa    24240
atgaagattt tatagttgac tcctattttt ttatagttga ccgctatgct tctttaagtg    24300
aatatacctg cttaaatttt cataggtaat tagcatataa atgatatttg aatgtgtttg    24360
tgaaaagcat tattacagtg ttgagagtgg gtgcagatga ttttttggg ggcttatgta    24420
tacatatcta tgattgtctg aatctttgaa atttagtttg tcagatatca agttatctta    24480
atttttttca agttatctac agggttacct ggatagcgta atagagttaa tttagagatt    24540
aactgtttaa tatttataaa ctcatttgta atatctctaa tatatttacc agctacttta    24600
aatcttatgc aaggaatgat atgtgatact gaagtcaagt atgagaaaca tttcagagaa    24660
ttgatttgaa tggaaaccat aaagtacctg tcaaataaga ttggagttga tttgcaaagt    24720
tgatttgaca aaaactcaaa gcataatctt acagccattg tagtcacttt ctcttgaaat    24780
cttcattgta agaatgacac tggtactttc aaaactgtgt aattacagta aggaaaatcg    24840
aagtgaattt tattactcaa gtagattgca aatatttcat tgttcaaaag tatttgatta    24900
ggccattttg acaatatttc tgagaagtgt tggaagaaat gttgaacaaa atgagaaaca    24960
gcatttgta gagaatcttg gattttaaag ttttacttaa catgtgtaat taaagtagca    25020
tgctttactt atttagaata tttaattatc cattttattt tactagaata tgaatgccca    25080
gagggtattt gtttgtttgt ttcgctcaca gatgtatcta tccctggaat gtcctttggg    25140
atgtatctgt ccctgaaacg tcatttggca aatagttgac actcaagaaa tgtttgttgc    25200
cgaatggatt acctgacctg ccccagcctt cttataactt tcccagagtc agtggggaa    25260
aaatacttaa aaattgtttt agaattacaa accagagagt aaattgttaa taccttagct    25320
atagggaga ggtggttaga gtggagttag aaagttagaa tatttactta gttttgtttt    25380
ctgtatcatt ctattaccca aggactggca gtggaagtgg ggagtagaat gatagtttgt    25440
aaggcagtgt ttccttaaac aggatgctag atacctccaa agaaatgaac atttgttgag    25500
cagggctat aaagtagtct ttatgccaga ttatgtttca tgtgtgttat cttaattttc    25560
atgacaactc tgggaaatgg gtagcattaa tccccatttt acaatgaaa ggaaaactga    25620
ggttcagcga atttaaaggc agtaacttct cctgattatg ttatattact ggtgagcaac    25680
agatctggga gacggaatgt tcttacccaa atttgtctcc aaagcctgtg ccattgccac    25740
tacaccaaat ggcattcttc tctggtgtct ggaagggtgc taattataat tatattagtt    25800
tttagctagt ttcttttcat ggtctatgct agtgtttaat cagtgtcctt attggcaaag    25860
atctgtcttc tgatgaacag attttgtgtt acaagtaatt ttcattgttt gatcttctct    25920
gggataatac tactcatcat gcttaaaata gtctttcaaa ttagacatga taggtttact    25980
tttttttcaa gcatatagaa aaatcttata tatcaacccc ctttagaatt tctgtaggtc    26040
agttaatttc aacaacagaa aggcagaagc aagaaaatcc tatttagaat ggaaaaagaa    26100
aagtatttaa tctctactga tagtaatggt ttaagctgtt atataaggga aagatgctta    26160
aataggactt tagcattttt tttgcccttta ggttttagct tttaccataa aaggaattct    26220
tcagtatttc tatatagata agtttgacca aattgtaaat tggttcactt aaaagtagaa    26280
```

```
gcattaaaaa aaatgtttct tttacaggag cagccttgcc tccatgtcaa tttatttttt    26340
taatggccca atcagaaaca ttgggccttg aaagagctgc ttctacagtg atgtattgga    26400
ggactagtct ttgacatggt gtattgtttt tctctgtaag cagctcactg aatcaggttg    26460
ttttctttgt ttgttttttt cctgaatctt ctcaactatg gcttctctct tgaaaatgtg    26520
aatttagtat attgtgaaac tggagtgaaa cacaaaatat ccttttaaaa attagacttc    26580
ctatcttaaa aattctcttt ggacggtaaa tgtaaaaagc ataaaagtta ttaacctaac    26640
atatatgcaa tgaatattta tatataccag ccatattttc tgtggaattt acgtattatg    26700
aaatacaagt cgtagactga actatatgaa attgtcattt ttttaggtca aaaaaatggg    26760
tgagggccag gcatagtggc tcatgcctct aatcccagca ttttgggagg cctggcaaca    26820
tggcgagacc ccatcactac caaaaagaaa agggtgaata ttggcaagct caaagctcat    26880
atagttcaac ctaatacatg aatttagaat tccctaaata agacatttcc tgaaatatta    26940
atttatactg tgttatccag ctattttttc aatgaaggaa aactctttaa agttagttta    27000
ggttaacctg aattgttaaa ggtgtttgaa atcttaaatt gataatactt tctttccatt    27060 ttctttttt gttgttgtta gtctccttat aacagataac agctgataga gttgttttct    27120
aggtctccaa gagagatatt ggagtttatt tctaaaagat tttgtggaat tttttttaatg    27180 catggtgttt tgtgtccttt tttagtgata cgtgatttgg ttgtattttc aaaggtttgt    27240
gctttctgga aatctgcatg gtggctcagt ggtagcaagc tatccttttg atgattctcc    27300
agaacataag gccactggaa tctatagcaa aacctcagat gatgaagtat ttaaatactt    27360
ggcaaaagct tatgcttcaa accaccccat aatgaaaact ggtgagcctc attgtccagg    27420
agatgaagac gagactttca aagatggaat cacaaacggc gcacattggt atgatgtgga    27480
aggtatgcaa agcattgagt ttgctacatt ttccccttg ttcgttgaat tttgttatgt    27540
gtattctgag caaaaaagaa gaaactctgt agaaatctaa cttaaaaga tatttatttt    27600 tattttgaaa atttcaaatc tacagcaaaa ttgaaggact acatgaagac ctatctgtcc    27660
ttcatttaaa ttcaccactg ttatcttatc ccagatggct tgcctctccc tctctcttt    27720 tcactctcta catgcacgtg tatgtgcatg cacacacaca cacacacaca cacacaat    27780 cacacaattt ttttgccaaa ccatccaaaa gtaggttgca gatttcacaa cactttacct    27840
ataagttcct cagcatgtat ttcccaagta cagggacatt ttcctgttta actatatact    27900
attaccataa ctgagaaatc aatgataatt taatattatc ataccacatg ccatccgtaa    27960
ctcagatttc ccccattatg tccaaagtag ccttggtagc cccttttttat ccagatctag    28020 tatccaatca aagttcaagc attgcagttg gctcttgtaa agagaccgtg ctaatagtcc    28080
tatgaaaaaa ttccataatc tagattgtca ctttcttcat ggtaagatta ggtcaggttt    28140
cccagcaaga ctattatata gatcatgttg cgcattatat caggagaccc ataacgtcaa    28200
gctgcaagtg gccaagttgg acagcttggt taacatgatg accaccagca accaggtctc    28260
tccatttaaa tttaaaatgt atatatttt taagagatag ggtctcactc tgttacccag    28320
gctgcagtgc aatagtacaa tcatagctca ctgtaatcac aagctcctgg gcgcaagcaa    28380
tactcctgcc tcaatctcct gagtagctgg aactatagat gtgtgccacc atgctagcta    28440 attttttaaat ttttttgtaga gatggggtat cgctgtgttg ccgaggctga tctcaaactc    28500
ctgacctcaa gggatcctct tacctcaaac tcccaaagtg ctgggattat agatgtgagc    28560
cacttcaccc agcccagatc tctccatttt acataaaggc acattttcct tttgtatttt    28620
aatctgtgag gtgatcatgg aatgctgttt tttttatttt tattgtggta aaacatacat    28680
```

```
atatatatac ataacatgaa atttgacagt ttaactgttt aaacattttt aagtgtagag    28740
ctcagtggta ctaattttca caatgttgtg caaccatcac cactatttct aaaacttgtt    28800
catcatccca aacagaaact cggtaggcat taaataataa ttcccacttc catctctatc    28860
ccttacccc  agccattggt aacctctaat ctactttcta tctctgtgaa tttgcccatt    28920
ttagatattt tatataactg gagttataca atattcttcc ttttgcatca ggcttatttt    28980
tcttaacata atattcttaa gggtgatcca ttttgttgca ggtatcagaa ctttattcat    29040
ttttatagct gaataatatt ccttgaatgt atatgttagt aatacatttt gtttatccat    29100
ctattgatga gcactgggtt gtttccacct tggctactag gaataatgcg taatgaacgt    29160
tggcgttcag gtatctgtat gagtccttat tttcaattcg tctggatata tacccaggag    29220
tagaattgct gggtcaaatg gtaattctat gtttagcttt gacagactat tttccacagt    29280
agatatacca tttacattcc caccagcaat atataagaat tccaatttct tatgaaatgt    29340
tatttttaa  agaattgttt gttgttgttg ttgttgtttt cagatggaat ttcactcttg    29400
ttgcccaggc tggagtatag tggcatgatc ttggctcact gtaacctccg cctcctggct    29460
tcaagtgatt ctccagcctc agcctcccaa gtagctggga ttacaggtgc ctgccaccag    29520
gcccagctaa tttttttgtat ttttagtaga gatagggttc catcatgttg gccaggctgg    29580
tctcgaactc ctgacctcga gtgatctacc tgtctcagcc tcccaaagtg ctggaattat    29640
gtatgagcca ccgtgcctgg caagaattgt taatacaagc ttgaactgtt tacctttct    29700
ctttaaatgc tatgaaaaca gctattactc ttttttaaact ttaggtatgc tttgaataat    29760
aacgttttg  tttttatgca cagatgtaga tgtagaggga acttagaagg aataagtcaa    29820
ccaatggaaa tgtcatcagt gtaaattttt tcttttctag gagtctgccc atgatgaaat    29880
gccttaggtc ttccttacct ttttattggc agtcacatta taaagtgtct tatgacatgt    29940
ctcttaatgt atatttaaac ctttgaatta ctcttttact ttttatatca agccatatgt    30000
acccaaaatg ggtcataagt ttgagaattt aatactttcg ttactggatc tttggggtat    30060
tgcttttctg gttggaaacc tctgtgcctg gtggtgcctt tgcccaagtt cttgtcctgc    30120
atccaggaag aatgaggtat gcagacaagt ggagggtgag caagacaaag aggagcttta    30180
ttgagctcag aggagaccgg cagtgggcat ctcctctctg taggcaggtc acccagtcaa    30240
gtgttcagcc ctcagcacaa aggaaccctg gagtgggtgg cccctctcta caggcaggtc    30300
atcctgatga gtgttcagct tcagcttca  gcagagagga gctaccctct ggttgtccca    30360
tcatctctcc atcctctgcc ttgctctgac tgagcccagg gctttatgg  acctcagagg    30420
ggaggaagtg tatgccgatt ggttcatggg cgccacgggc agcctggaaa aggcacaagt    30480
ccccactcca gtctatggga ctggcagcct ggccccagc  cttcaggacc tccctggcct    30540
gaaggtgggg cctcaccagg gaccccctcc cttatatccca ggagctagtc tgcctcttgc    30600
tgctttccat ggcaccccgg ctgctcgtgc taagggcac  ctgcaagcca gtgctgagtc    30660
gccctcagtc cccaaccttg gttccctctt ccatgcttgt cagtgcccag tccggtgggg    30720
gcccaggcaa cagggcccaa gcatgtgcgt acccctccgg gcagtgacag tgcgccgcct    30780
cagctccaac cccaatcccg gataggagca gacgcaagaa tggggagagg ccaggcagca    30840
ggagcaggca tctccaagcc tgcaagggta agggggggcct aggaggtcgg gggacgcagc    30900
tgctgccagc tcccagctcc cgccgactca gtggagcatg cagccccagc cgtgccccct    30960
gggagcctgt ggcgggtggc tcctaatcct cgctgggcct gggccagtgt ctgggccagg    31020
ggcgacattg ccacaagctt ccctgttgcc ctggggctaa ggagtggccc ggagctgatt    31080
```

```
gcgggcctgg ggccaggctg tcaggagtgt caggctggga ggtcacccca cgtgtggcgg   31140
acactgggga cttggcccca agtggcccgc gcagagcctc ctcccgagcc caggaacccg   31200
ggacccttag tggggtgggc gcagtggctg cacttctggc cagatcccca aagctggagc   31260
agctcctgct ttccgccccg cccccgaagc acagccccag ctccgcatag gggttcctct   31320
ctgcctgact acattactcc cccgctgtgc tgctctgggc ctgaccccat tacggcagcc   31380
cccagggcag cgggctctgg ggggtggcag cgggctgtgg ggggtggctg cagaaggggg   31440
ggctgtccgc ctccttcccg caccttccgg cctgctgctg ctatcacttt ctagaatttt   31500
ctgatcctcc tatagtttct accagtgttt cttgtatatc agaagcattc aaaaagaggt   31560
ttgacatact atttagaagt gaaaccttct ccccataaca attagaggtg atttgaaaat   31620
cattaaaaat tttttgtag ataatggact tactttaatg tgtaatttt acatttcagt   31680 ccttgggaaa tatatttaat aaaacctaac tttgaactgg tggttttgta atctagtcaa   31740
gttgcttcat taatttgaga tgatgttact taaaataatg gggtaaatac ttaactttgc   31800 cttttttggaa aaagttgtaa aaggttagaa agtaatttct aactgacaat taattgagga   31860
aggtaaatgt atctcatact acttaaaaaa taaatatccg gcctctacaa aacgtaggtg   31920
tactttggta ttaaggccag agattatttg gtgaagctag ttatcatcag atttttctga   31980
ttattcagac atctgaagaa gctacattat gctgctgtca tttttatttt catgagcatc   32040 aactttctc ttgtttcagc tgaatgtcgg atatgtccta tgttatttct acaataactg   32100
gcttatttct cttcgtacct cagcaaatat tgagcagttt ccccttgaag aggaggctgt   32160
gatggtttta gtttcaacag ggtgaattca ttgtgtttag tgagtaagat gttgtgaaac   32220
cttgtgacta ggcatatatt caaaaaaccc ggatgtcctg gagtaattt tttttttttt   32280 ttgagacaga gtcttgctgt gttgcccagg ctggagtgca ggcgtgatct cagctcactg   32340
caacctctgc ctcctgggtt cagatgattc ccgtgcctca gcctcttgag cagctgggat   32400
tgcaggtgtg tgccaccatg ctggctaatt ttttgtattt taagtagaga cagggtttta   32460
ccatgttgac caggctggtc ttgaattcct ggcctcaagt gatctgccca ccttggcctc   32520
ccaaagtgct gggattataa acgggagcca catgctcagc cgagtaattt tactgatgtt   32580
ctatgtgata tatttaggaa ttctagctta aagaagtata gacctttaga gctgaaagtg   32640
aatatattga tttagtccaa ccctttttgtt ttagagaaaa tcaaggcctg agagaggaac   32700
taacttgtgc aatataatgt attaatatag caaatatta ctgagttcct gccgtgccac   32760
atatactgta ttaggtgatg taccggtata cagtgagagc aaaacagaaa caactcctgc   32820
tctgaggaat cagatagtat attagtagtg tggaatctgg ggtgatttgg gccctagtgc   32880
ctttgccttc attgccaggg ctggcccagc atatctagct gcctatgtgg gtgagccttg   32940
cttcattcaa catgtctcac aaacctcagg atccatttag gaaatggcta tcctaataag   33000
gctgatgaat agccacatcc ccttccaaag cctcgttatt gtgagaccta ctctggactt   33060
gttcatggag taagatgcct ttttttttt ttgagatgga gtttcgctct tgttgcccag   33120
ggtggagtgc aatggcacaa tctcagctca ctgcaacctc tgcctcttgg gttcaagcga   33180
ttctagtgcc tcagtctcct gagtagctga ggttacgggc atgtaccacc atgcccggct   33240 aattttttgta ttttttagtag aaacagggtt ttaccatgtt ggtcaagctg tcttgaatt   33300 ccagacctca agtgatccac ctgcctcgcc ctcccaaagt gctgggatta caggcctgag   33360
ctaccgtgcc tggccgcctt tttttttttt tttttttta atcacagtgc gctgatttgt   33420
atgccatttg cctaccgttc tttcttcaca gttttgaaga cattgtaaaa atcatatgat   33480
```

```
gttttggtat gtttattcca aagcagattt aataaaaact gaactgtagt tttaggtcaa   33540
cttttaagcc atggcgtgtg cttgtagtcg cagatacttg ggaggccaag gcgggaggat   33600
cttgagttca agcccagcct gggcaaaata atgagaccct gtctccaaga aaacaaacag   33660
acaaaaaaga attgccttct ttcaaattat acaatttaag gaagggcagg caacgtatag   33720
ttgaaattat ttgatcaaag atcatagttt tatgtaactt ttagaagttt tcttgggcag   33780
aacattgtta tattttattt tcttgcagat agaagaacag tagaaggcag tgcaatgtag   33840
tggcaaagag agagctttgg aatcccgttg ccttaggttg gaatcacaac tctgccttga   33900
ctagctgtgt gcgtgtgtgt gtgtggtgtg ggtgagagac aaattaatga atttctctaa   33960
gcctcaattc ccacttatat aaaattaaga taaatactat ctactcacaa gattaggagg   34020
ctcaagtgag aatgtgtgta aagcacttta gcctagcatc tggtgccatg gctacttata   34080
tctactagag tttaaactta ctcttgaaga tagggacttt gtttattcc attttctatt    34140 tctagcacac acaaccatgc ctggtatata taaggtaaaa aatagtcttt ttggaataaa   34200 tgaattttg ccatccgaaa cataaataca tagttatttg atctttggat aatctttttt    34260
tttttttttt ttggagacaa agtctcactc tgtcacccag gccggagtga agtggcgcaa   34320
tctcggctca ctgcagcctc tgcctcccag gttccagcga ttctcctgcc tcagcctccc   34380
agttagctgg tgttacaagc atgcaccact acgcctggct aattttttgta ttttttagtag 34440 agacggggtt tcaccatgtt gaccaggctg ctctctaact cctgacctca ggtgatctgc   34500
tcgcctcggc ctcccaaagt gctaggatta caggcatgag ccactgcgcc cggcctaaaa   34560
tcttagatct ttagttaatc ttataacaat ttataaaaat attcttccta gttttgctcc   34620
tactctgagt aaataagctt gccttactgg tagatcctag atcagtatta tttgaacttt   34680
tttttcttac ttttaaccta taatatgaaa tacctttag ttgtgtatgt acatttcata    34740
tatatgtgtg tacattaaaa aatttcatgg aacaatactt ttactataca ttctggtatt   34800
atttctttta gtttgttcta tatcattctt taaaaaatat gtctgaaccc actaatatat   34860
ctcacaaccc actaatgcat gatgaccttc agtttgaaaa aacactattc ttgatcaccc   34920
tgtggtagaa ttcattttatt ttcaaattct aagtaggaac aaaacacctt acaagttgtg   34980
tgtgataact tattatttgg gttttttcctc ccaacttgtt tatatgtttc agttatttgc   35040
agtgaggact gggccacaga tatttatctc agatgttcta cttttagatt gctttcccta   35100
aaatacgaat gagtgttgag ttaggaaatt ggtcagaaat atagttgtca ggcctatgta   35160
ttgctcatgt gagtctatgg attctattat tagttaggac agctgccata aagctttata   35220
tttgtcttct taagccacta taaacttgag gctgagcctt ttcaaactag taattatgat   35280
tgttttctcc tctggaagaa gaataaactg ttctttggat ttatcaaatt ttcttccctc   35340 tcctttata caatggacag agttatgaaa tgtggccaga aagcatataa tgtaaccaat    35400
tcagtttttt gtgtgaatat caactccttt tatcatgcag acaactattc ttttccccaaa  35460 ctggaggtca gactgagcag tagcagtgtg ctttaaatat tgaagtatgt ttggctggaa   35520
gtagattgtt gatggaaaag gaagagcatg gggaaaataa ttacccaccct gttttcaaca  35580 atgctgttga aagtttagat ttggtccaga aatggaccag aaagcttatt tttgaggagt   35640
attttctgtg tcattaaata ggatatatatg aattaaccca gtaacaccag aaaattgtaa   35700
tctaaaacaa aaaggaataa gatgaacagt atgtaactat aaaaatacaa tatctgatat   35760
taagaaacag acaaatccat aaatatagta ggaagtttaa aataggcctc tttcagaact   35820
agtaggtcat agagatcata actgttagat cacaaaaatg tgagtaagga tacagtggat   35880
```

```
ttgaataaca taaataaacc aatctgacct aatgaacgcg tacagaatac tgtccttata   35940
tctaattttc ctgcagagtc tgtttactaa tttgaggtgt ggatgactaa gaaaccagct   36000
gtcacgctta gggaagatgc atctggttct gttagcgctt gtgttacttt gttttttaaga  36060 ttatatatta aaaactaaac aacaaagata cacaggtaaa ataggccagg agcagtggaa   36120
gcacacttgt aatcccagca ctttgggagg ctgaagtagg aggattgctt gaggccagga   36180
gtttaagacc tgggcaactg gtgagacctc atctcttaaa aaatacaaaa attagtgggg   36240
catggtgatg caccccctgta gtcccagcta cttgggaggc tgaggggctg aggcagcaag   36300
atagtttgag ctcaggaatg tgaggctgca gtgagctatg attgcaccac tgcactccag   36360 ccttttttttt tttttttttt tttttttttt tgacagggga agacccgtgt caaaaaaaaa   36420
agaaaaaaaa aagcttataa tacagggttc ataggatcaa gtctaatact tcttagcatg   36480
ggagcgaaga tcccacagtc tgactcaagc ctataagttt agcctcagct cctacctctc   36540
ctctgccacc ggactacttg tccttcccaa atgtgaacct tcacatgtta ggctatcctc   36600
tgtctgaagt gcttttcacc agtttagctg taacctcttc tgaaacctct cctataataa   36660
ctgtcactat cctaccttcg agagcttttt gtttatacag taccatcagt ataaactta    36720 tccacttatg ttgttaatag ttttttttgtt tcctgttagt gtgtgaattc tttgatgata   36780
aggacagtgt agtgctattc gttttggagt tatctttgtg caaatgtat tggcaggaaa    36840 gagtcctaga ggagggaaaa ctagagaggt gtttacagtc atctgggatg aggtctcttt   36900
ggagataagg gctttaccta gagggcatgt aggggaatga aaaggagta taagatacat    36960 atataagaag ttatgcaaga agaactgcag aattgaccat cgtttaaata gcagaacaga   37020
atgtcaaaga gaggatgtca aagatatgac tttgaggatt ttgagcttgg attagaaaga   37080
atgggagtgg gaaaaactaa ttggatggtg gggattggga gacagcaagc gagtgagcat   37140
gtgtgtatgt gtgtgtgtgt gtgtgtgtgt gttcgttcag gtgaaagagg agtgaaaact   37200
ggaaatatta atagtacttg atgtactagt cacaagtacc caatgggcag ttagggaata   37260
ggttctagag cttgggagag aggtcaagat gagaaagaga tttagaagtt ttgagacatt   37320
tggaaagcat atggcagtgt agatgatttt gaaaattgaa ttaatagtgt tttctggcat   37380
aatttaattg cgtggagcta gaagttcaac cagaacatat atataaatga acagatgggt   37440 gcttttttt  tttttttttt tttacctcta aagtgaatgc atttcgtact gggatgtttt   37500
ccttaaggaa tgccaacaat tcagatatta attctcagcc tgatcatatt ttaaaggtac   37560
agttgataat caaatgtgca ttagtaaagt gcttttggtc ttacctgatc ttgcacatta   37620
aagacctggt tgaggctttt tcttcccttt attttctctt ttaaaatctg agtgctgcct   37680
aatttaaaag gaaagcaaaa aggtaaaaca atactccaaa acagaatatt tgcttggagt   37740
cacgagttgg ctttagtaaa ttgaagcata acctagtata aagactgacc tttaggagca   37800
gtgcagttgt gtactttgta acgtgataat aggcctaaat gaagagaacc taacactcct   37860
ttaggatttg gccccccagtc tttagatcta atgtgtataa attggatgta cttttttctt  37920
ttcctttttt cctgtttaac tcaggtggta gagaatggga gagtacattt aaaaaaaaaa  37980
aaaaggaaaa tacagttcaa agagctatgt gggagacagt gttaaccaag ttagacaaaa  38040
atgaaaacag atgtaggact gtgtaattta gtttaactct gtagaatcat atcattagca  38100
aatatatatt cagtgggagt ggtgaaggaa atagattttc acaagatagg ttgctcagaa  38160
tacaaagacc aggttcagtt agttaagatt tgatcaatgt gaacttgaat ttaaaaatta  38220
ggaatttggg gaattttttt aagagcaacc tctgattttt ccattgattt ggcccagatt  38280
```

```
ttccacctaa aatttttta caaacgttat gctcattagc ttttaaaaat atctcagaaa    38340
gtacaaaatt atcacttaat aactcactta ttgcctataa aaaattgttc aggaaattca    38400
aagtcgtgag agaatttctc actatccttc aaagtagttt taataaagta atatcattaa    38460
gctccaagtt gaaatatagg gtagaaattg tctgtctata ttcctagact ttaaaatgct    38520
tttcctattt aaaaaaacac attgtagttt ccttgtaaaa gattaatagg gttcttgtgt    38580
aatgcagttt gacactttat agttggcctg cagaggcaag taaaaaaaaa aacaaaaaaa    38640
acttgctatg tttcttaaca ctgaagcatt ggctgtattt tttcttttgg ctttctgttt    38700
gagacagaag agtgaatctt tagtatcttt gaatgaagga ttgaatttat taatctcccc    38760
tccccttaaa agctagatct ttctgtggtg aaaagagtga taagagactt gtttcctaat    38820
caagacggat tgagtatctt aaaacacatg aagattagtt gtgctacaaa tcgattgaaa    38880
gagtttaatg ggtacgagta gatcacttga tcagaagatt tagctatccg taacaattag    38940
cattggtatt gatcacaatt tgcagtatta ctagacagat tcctaatggt tacactttga    39000
gtcttgttct ttgatactgg taaatgaatg gtaggtttct ttctttcctt tcctttcctt    39060
tcatttcctc ttccttttctt tccttctttc cttcctctct ctctctctct cttaattttt    39120
agatctcagt tttcatacgt attctttcct aaaattaatc tgcctgagaa agatacttgc    39180
tgtggaggtt ctatctcata ttctcttctc ccaattgact gaagacaggc atacttttct    39240
acccacctga atcacattat ggtgtattgc cttggagttt tacaaacttc cagggcacta    39300
aaacaaaagg aacaatttgg tgattacttt aatggttaaa cagtaccata agagcatcac    39360
ccccaatttt tctttgaaag atgtatttc agtaattatt tcttatattt actattttat    39420
tatttaccaa aatttgtaaa aaaaactatg ccttttttgat aaattgtgtg ctagtgacta    39480
ttgtaataat tcaatttaga ggacacagaa ttaatactta gagcattaca gtcattggaa    39540
attaagaaaa atttaaatac actaacatac tatagattga aaaattatag aatgattggt    39600
gaaagacttt caagcatgca ggtatatcac attcaaatag cattctgtgg aggaagtaga    39660
atggaaaaaa agttcaaaga gaaaagaga agatgtggct gggtatggtg gctcaggcct    39720
atgatcctgg cactttggga ggccgatgca gaaggattag ttgagctgag gacttcaaga    39780
ccagcctgag caacatagtg agatatgtct ctacaaaaag taaaaataaa aaaattagcc    39840
aggcatggtg gtgcacatct gcagtccagt ctactcagga ggctaaggtg ggaggatcac    39900
ttgagcctgg agggcaaggc tgcagtgagc tgtgactacg ccactgcact gcagcttggg    39960
tgacagagca agactcctgt ctcaaaaaaa aaaaaaaaa aaaaaaaga agatatataaaa    40020
ttccttaaag aggcatgttc aggcaacttt taaatagata tttctagaaa tcaaatctct    40080
ggcatttta tttggatata tttaaaataa taatataaaa gttttattta aaaaaaactg    40140
gtcatggtgc agtggttcac acagtgtaat tccagcactt taagaggcca aggtgggagg    40200
attgcttgtg cccaggagtt cgagaccagc ctgggcaaaa tagtgagaca ctgtctctac    40260
aaaaaaaaaa aaagagaaaa atttacatta tgcaggatat tcctttgttt acaactattt    40320
aaacttaaga tgaaacttg tgaataccaa cttaaaaatt tgtgaagcgt cgcatatttt    40380
ttcagttatt ttagtattaa caaacaaatt gaagatcatt ggtttatata acccctgag    40440
agactaaatag tagaatagaa cagaataata gaatagaata gaacagaata gaataataga    40500
atagaataat aatagaataa tagaaactcg cttatttatg attgttaata agtaggataa    40560
attgcagatc atttatacta ttaaagtgct ttattgcttt gaggtgtgcc tgtaactgaa    40620
tgttttactt ccaaaattaa aatttctttt ggctgaataa agatattctg aaacctgaca    40680
```

```
tttctccttt aatctttgtt gagccaaatg acatatcaac ttaaaaagat aagcaaatat   40740
attaactgaa tctggcagta gctgcagctg ttattaatgt caggcctatc tacagatcag   40800
tggctgctcc ctgtttgggt gaactctagc tttgggtaag taggttttgt gttgagaaaa   40860
aaaaaattaa gacaacaaac ctgaaccagc tacttagtta ggattactta ttatacagtc   40920
tttgacattt ggtttcagaa aaataaatgt taagtttaac atagatggca aataatgcct   40980
atctgtgaca tctcacaaaa aattcttgaa ttattcataa cttaatgtcc ccatttggtt   41040
ccatgtttta aaataattaa aaaaataaat ttaaaaataa ttttaaaaat aaaaaaaatt   41100
tttttaaata attaaaaaaa aattcctaaa ccaaaacttg aagttgatga ataaagacgt   41160
tttgatattc taatgctagg atagtttatc ttttttgtctt atgaaataaa aattagtttg   41220
ctactcttca gacatttatg agtttgaaga agataaaggt agacatcaca actcattaat   41280
tgccttctga aaacagttca ttattataga ctcagaggaa acgtgcttta cttttatgag   41340
attgtatcaa gacagagata aatattttat aatatattta tgttattgat ttcaatataa   41400
taacatcgtg gtcagagaac acccttttgta tgtaagtttg acctaggtca aacttaaatc   41460
atacaaagtt tgacctagga tatggtcaga cttggtgcat gttccatttg tacttgaaaa   41520
gcatgtgtat tctgccattg ttgggtgggg tatagtataa atatcattta tagatctagt   41580
tagttgatag tattattaca tttttctcta tcctttgctg attgtctttt ctgctgatta   41640
ctgagagaag aatgttgaaa tgtgcaacca aaattgtgga tttacccatt tttccttta   41700
gttctataaa ttttttgtttt atatatttca aaattctgat tgttgcatgc acatctagaa   41760
ttatgtcgtt ttggtgaatc tacacttttta tcgttatgta atgtccctct ttatctctgg   41820
catttttcct tgctctgaag tctattttac ctgatagtca tatagctact ccatcttttg   41880
atttgtgtgt gtatggtgta ttttttttcct ttcttttaac ttacctatac cattatattt   41940
aaagtgagtt tctgacctgg tgcggtggct catgcctgta atcccagcac ttttggaggc   42000
tgaggcaggt ggatcacttg aggtcaggag ttcgagacca gcctggccaa aatggtgaaa   42060
ccccatctct aataaaaata caaaaattag ctgggcatgg tggcaggcac ctgtaatccc   42120
agctactcga gaggctgagg caagagaatg cttaggaaac cgggaggcag aggttacagt   42180
gagccgagat tgtaccactg cactccaacc tgggtaatac agcgagactc tgtctcaaaa   42240
aataaataaa taaataataa gtaaataaat tgtgtttctt gtagttgcat agagttgggc   42300
cttgtttttt aatgagtttt acaattcctg tctttagtt ggtgtgtttg caccatttac   42360
actgaatata attattgtta tgtttggatt taggtctact ttctcatttt tcagtttgcc   42420
tctctcattt taatcccact gcttcctttt tcctgccttc tattggattg tgttttcaac   42480
gatatctttt agttgctcta gtaaatacaa gttactactt aactttcac agttctacct   42540
aaaattaata ttttacttca agaggaatgt acgaacctac ccaccatacc ctttatcctc   42600
cccttttatg ttgtacttaa cttatatata tatgctgcac tgaaacccct actagacaat   42660
gttataattt ttactttcaa ctgtcataca cagtctaagg gacttaaggg gagaaaaata   42720
gctgattgta tttaccattt ctgttgcttt tcattcattc ctgaagttct aagtttctct   42780
gtggtataac ttctcttctg cctgaagagc cttctttagc atttctttta aagcaagtat   42840
gcttataatg gattatctta gttttccatc tctgagaatg tgtattttgc catcattctt   42900
ttttttttttt tttttttttt ttgagatgga gtcttactct gttgcccagg ctggagtgca   42960
tggcgcgatc tcagctcacc gcaagctttg cctcctgggt tcactccatt ctcctgcctc   43020
agcctcctga gtagctggga ctacaggcgc ctaccaccac gcccggttaa ttttttttt   43080
```

```
tttttttttg tattttgtat ttttagtgga gatggggttt caccatgtta gccaagatag   43140
tcttgatctc ctgacctcgt gatccgcccg tctcggcctc ccagagtgct gggattacag   43200
gcgtgagcca ctgcacccgg ccttgccatc cttcttgaag gacatttta ttggatataa   43260
aactcggggt tgtggattgt agtttgttgt ttttgctgtt tgttttttag agtgctttaa   43320
taattttgtg ccattgcctt ctggcctcca tggcttctgc tgagaaattc agtcatttga   43380
attttttcttc cccttttatac gcacatcatt tttctatggc cactttcaag actatttat   43440
tgctgctgct gctgctgctt ctgcttctgc ttcttctgct tctgctgctg cttcttctcc   43500
ttctccttct cctcctcctt cttccttctc ctcctctttc tcctcttact cctcttcctc   43560
ttcctcctct tcttcctctt cctcttcttc ctcctcttcc tcttcttcct cctcttcctc   43620
ttcttcctcc tcttcctctt cttcctcctc ctcttcttcc tcttcctcct cttcctcttc   43680
ttcttcctca tcttcttctt cttcttcctc ttcttcttct tcttcctctt cctgttatta   43740
ttattgtgag acagagtttg gctgtgtttc ccaggctgga gtgcagtggt gcggtcgtgg   43800
ctcactgcaa cctctgcctc ccaggctcaa gctatttct tgcctcagcc tcctaagcag   43860
ccgggactac aggcacgtgt cacaacacct ggcttatttt tttgtatttt ttgtagagac   43920
aggttttcaa catgttgccc cagctggtct caaactcctg ggctcaaggg atccgcctgc   43980
ctcggtctcc caaaatgttg agattacagg catgagccat tgtgcccagc tgactttttt   44040
tctgtctttg gttttcagca gtttgattat aaaatacca tgcatggatt tttttgcact   44100
tatagtgttt gagatttgct gagcttcttg aaatgtaagt ttttgtcttt tgccaaattt   44160
atggtgtttc tagccattat ttcactttt ttttttttt aaatagcatg cgccatttt   44220
tttttctctc ctgagactcc agtgataaca atagtaggcc ttttgctatt gttcttaaaa   44280
ttttttcttc ttttttttca gatctttttt tcttcttct ctgttattca taaggcaatt   44340
tctacttacc catcttcaag ataactcact ttttcctatc atttccattc ttccattaaa   44400
cccattcagt ttattttt aattagtta ctgtatttt ctgaaattct gaatttcta   44460
cttttttcta ttttgcatgt ttggtatctt tcttttactt taagactgtt taatcttact   44520
tccttggaag gctgggcgtg gtggttcaca cctgtaatct cagcaattcg ggaggccaag   44580
gtgggtggat tacttgaggt ccagagtttg agaccagcct ggccaacatg gtgaaaccct   44640
gtctctacta aaaatacaaa aattagctgg acatggtggc acatgcctgt aatcccagct   44700
actcagaagg ctgagggacg agaattgctt gaacctgaga ggcagaggtt gcagtgaact   44760
gagatcgtgc cactgcactc aagcctgggt gacagagcga gactctgtct caaaaaaacc   44820
aaaccaaaac aaaacgaaaa ccttaattcc ttgtaacatg ttataataa ctgctttaag   44880
gttagtctgg taattccagc atctgtgtca cattggagtt ggtgtctgtt gactttttt   44940
ctttataata tattgagctt ttactggtta tttgaatgtc aaataatttt ggattatatc   45000
ctggacattt tgaatcttat gctatgagat ctgggtcttg tttaaatcct attaaaacat   45060
aatacttgtt ggctgggtgt ggtggctcac acctataatc ccagcacttt gagaggccga   45120
ggcgggcaga tcacctgagg tcaagaattc aagaccagcc taaccaacat ggagaaaccc   45180
tgtctctact aaaaatacaa aattagctgg gcatggtggc acatgcttgt aatcacagct   45240
actcaggagg ctgaggcagg agaatcgctt taacctggga ggtggaggtt gcggtgagca   45300
gagatagtgc cattgcactc cagactgggc aacaagaatg aaactccatc tcaaaaaaat   45360
aaaataaaat aaaaataata atacttgtct gtttgtgcca tcagggaatg acccagttag   45420
gttcagctgc aagttttgac tcgccttatg taagctgtaa ttccaatgtc agttcagttt   45480
```

```
tcaaagcctt tatagtgcta ttcagatctg tactgtatgt gcaccactca ggggccagtc    45540
tgggtgctgg gcagtaacct gttttgtagt tcagttctca gtgcttttgg tgtgctgttt    45600
aaggtcagac ctgtacatgt gcagtttaga gatgatccca ggtggtcaca ggcaatttta    45660
tgagatccct ttctcacatt ccctcatatc tgccatctca ctaaagtctc tgtcttccag    45720
ggtctccagt atagaagata aataaagaca tgaaagatct cctttcatgg gaaagaaagg    45780
atgtgcaata tcatttgtta tcagtgaaat acaaattaaa accacaatta gataccactc    45840
gtcttccact agaatgctta aaatttaaga gactttccag tggcatgagc aacttgttag    45900
gtgatgatgc agaataacta aaacatggat acattgctgg tggtaatatg aatatggtac    45960
aaccacttta gaaaacaatt tcttacaaag ttaaacttac tataagatcc ctccatgcca    46020
cctctagata tttacccaaa agataggaaa acatatgccc acattaagat ctatgcacag    46080
ctttaatcac caaaaaacaa gaaacaactg aaataaccat cacatgatga acagataagc    46140
aaattgaact acttttattc aatagaatac ttagtaatgt aatggaccat ttatatatga    46200
agaatataga tgagtctcaa aagcattatg ctaagtgaaa gaagcctaat acaaaaggct    46260
atatactata tgatttttatt tatatgacat tctagagaag gcagaaatat agggaaagaa    46320
attagattaa tggtaaccca gggtctggga accttctggg atatagaaat gttctgtatt    46380
tttattgtgg tggtagttat gtgactgtat acattgcact gtacatgtaa atgggatgaa    46440
ttttatagca tataagttat tatacctcca taaacttgac ttttaaaaag gctttaaagc    46500
accgtgttaa ctagattgtc aaaattcttt tgaatcattt acttaatact taagtgaaag    46560
gaaattattt aagaacctct gtatgcttca aagaagaata aaattcaaag tatcatgcaa    46620
aaatatttgc cttgtatatg ccgttttata acctttttg atgcatggta aatatcgtga     46680
caataaatat atgcctgcag taatttaaat ggctgcatag tagcccattt tatatcataa    46740
tttactaaac tggtctttca tttttgaaca tttagattgc ttccagtttt atgctctttc    46800
aatttgaata ctatagccct catccttata gctattatct tggaataaat ttctagaaaa    46860
ggaatttctg gttgaggtca tacctatttt aaagatttta tattcatatt actaaatttt    46920
cacccagaaa tgttctataa tcctttgtca tctctttttt ttctttctttt ttaatgaaag    46980 acacttcatc tttcattttc tttaaaattt ctgatggcag ctttttggcc aacagatatt    47040
ttactagctt tttggtagtt gaatctgtta ggtagttaaa tcttttaggt agttaaatct    47100
attcatctat tattcctctc atggttttat actactttgt tgtcatactt agaagggctt    47160
tcctcattct gagagagtaa aaacatttat gttggcttct ggtttcatta atggcttcat    47220
ttttatgtta aattccatat ggattaaaga gtttacttgg tatgatactg taaaccaaaa    47280
agtatctgtc tctaagatgg gtctcaatca atttagaagt ttattttgcc aaggttaagg    47340
acatgcccgg aagacataaa tacagtcaca gaaaccgtct gtggtctttc cctttctcca    47400
aagatgactt tgagggcttt caatatttaa aggggaaaag tgagctggag gggaaagagt    47460
aaaggtcatc cacatagtgc aagagaaaag gagcagttgg gggaatagtc aattatgtat    47520
tcatctcatg ctcagtaaat gggcactttt catgagataa ggtgaacatg aaagagctac    47580
ctgtggagat atttacccct ttatctgtag ctatctgctt aggaacaaaa ggaaaggcag    47640
cttcttgcat gactcagctt tcagcttaat ttttttcttt tggcatagtg aattgagtga    47700
atttggcata cctttcacaa tatgatgtaa aactccacca gtatttttg ccacctagtt     47760 aacctagtca accacttta accatgtaag agttactaat ttttccccc attggtttta      47820 aatacctgga tcatattcca aatgcttttg tttcagttac tgtgatttct atgttgttcc    47880
```

```
gttggtctct ttattttat acctgaagtg aactgcttta gtaagtgtag ttttattata    47940
tgtatttag taatatggca atgcaggtcc cctcttaaac cactcttatt ttttaatttt    48000
ttgggagata ttctcagcca tttctcagaa attctcacaa agttactggt acagtttaac    48060
ttctaaatca ttatgtccag ttgcaacaaa aaaatctatg ttttcataat atttataaat    48120
taatttgggg aaatttgata ttttataag cctcttatct agaggcataa tacactttac    48180
taaaatctcc tacatccctc agtagcattt tataatattg atttatatta tgcatttat    48240
tatacttcat cctatacatt ttgtgatttc gttgctggaa actttttaaa aattatattt    48300
gctgattatt gctgaaatac agtaaaaaat attgatttt atattgtttt taagtagtca    48360
tcttttatt tccagtgtca ttttacatga cttttatttt aacttaaata tggtcttatc    48420
aaagaaaaat ttggggactg tatgtcagga ttcaactaat attttctatt tccattagat    48480
tttacactgt gaagctaata ttaaaatcag tctataagac ctaaaataaa agaggcttgt    48540
ctccatgaat ctgactttta gtaattgttt gtagagatat atattaaaaa gtcaatattt    48600
atattatatg ctctgtcaaa ctaaggatgc taaatgtatt ttcttctctt ggaattaagt    48660
cttattttaa aatgatttct gtccttcctc cctacttgct acctggggga tatatttgta    48720
tgtgtcatta gatggaattc acaagttatg gtccaattaa agttaccttt aaaaacctga    48780
ttaggtaaca ctctaaaatg ttactgtaaa cttgatcttc ttgctgggtc ttagctagta    48840
tttcttaaat tgctgctaaa ataggacaat taagggatag acaaaagaat gctaggactc    48900
aagcctgggg attatagtgt tactctacgt cattgccttc tagcataatg aaagtgtgag    48960
ttggccatgt ttgcaaatta acacagctat taaatttac atatgcaaaa aaacccttag    49020
attagtttac atttatatgg ccctgaaatt gttattatta ttttttcttt tttattatac    49080
tttaagttct agggtacatg tgcataatgt gcaggtttgt tacataggta tacatgtgtc    49140
atgttggttt gctgcaccca tcagcttatc atttacatta ggtatttctc ctaatgctat    49200
ccctccccca gtaccccacc cgcctacagg tcctggtgta tgatgttccc tgccctgtgt    49260
ccatgtgttc tcattgttca attcccacct atgagtgaga acatacggtg tttggttttc    49320
tgtccttgtg atagtttgct gagaatgtgg tagtttccag cttcatctat gtccctgcaa    49380
aggacatgaa ctcattcttt tttatggctg cattgtattc catggtgtat atgtgcacat    49440
tttcttaatc cagtctgtca ttgatggaca cttgggttgg ttccaagtct ttgctattgt    49500
gaatagtgcc gcaataaaca tacatgtgca tgtgtctta tagtagcatg atttataatc    49560
cttgggtat atacccagta ataggatcgc tgggtcaaat gttatttcta gttctagatc    49620
cttgaggaat cgccacactg acttccacaa tggttgaact aatttacact cccaccaaca    49680
gtgtaaaagc tttccagttt ctctacatcg tctccagtat ctattgtttc ctgactttt    49740
aatgatcgcc attctaactg gcatgaaatg gtatctcatt gtggttttga tttgcgtttc    49800
tctgatgacc agtgatgatg agcattttt cctgtgtctg ttggctgcat aaatgtcttc    49860
ttttgagaag tgtctgttcc tttcctttgc ccacttttg atggggttgt tgttttttt    49920
cttgtaaatt tgtttaagtt ctttatagat tctggatatt agccctttgt cagatgggca    49980
gattgcaaaa attttctccc attctgtagg ttgcctgttc actctgatgg tagtttcttt    50040
tgctgtgcag aagctcttta gtttagttag atcccatttg tctatttgg cttttgttgc    50100
cattgctttt ggtgttttag tcatgaagtc tttgtccatg cctatgtcct caatggtatt    50160
gcctagattt tcttcaggg ttttatgct tttaggtcgt acgttaatt ctttaaaaca    50220
tcttgagtta attttgtat gaggtgtaag gaagggatcc agtttcagct tcctacatat    50280
```

```
ggctacccac ttttcccagc accatttatt gaatagggaa tcctttgccc atttcttgtt   50340
tttgtcaggt ttgtcaaata tcagatggtt gtagatgtgt ggtgttattt ctaaggcctc   50400
tgttctgttc tgtatctgtt ttggtaccag tactatgcta ttttggtgac tgtagccttg   50460
tagtatagtt tgaagtcagg tagcatgatg cctccagctt tgttcttttt gcttaggatt   50520
gtcttggcta tgcaggctct tatttggttc catatgaagt ttaaagtagt ttttccaat    50580
tctgtgaaga aagtaattgg tagcttgatg gggatggcat tgaatctata aatgaccttg   50640
ggcagtatgg ccattttcac gatattgatt cttcctatcc atgagcatgg aatgttcttc   50700
catttgtttg tgtcttcttt tatttcattg agcagtggtt gtagttctc cttgaaaagg    50760
tctttcacat cccttgtaag ttgtattcct aggtatttta ttctctttgt agcaattgtg   50820
aatgggagtt cactcatgat ttggctctct gtatgtctgt tattggtgta taggaatgct   50880
tgtgattttt gcacattgat tttgtatcct gagactttgc tgaagttgct tatcagctta   50940
aggagatttg gggctgagac catggagttt tctaaatata cagtcatgcc atctgcaaac   51000
agggacaatt tgagttcctc ttttcctagt tgaataccct ttatttcttt ctcttgcctg   51060
attgccctgg ccagaacttc caacactatg ttgaacagga gtggtgagag agggcatcct   51120
tgtgttgtgc cagttttcaa agggaatgct tgcagtattc aaaaaaactg gcacagtatt   51180
cttgtgccag ttttcaaagg gaatgcttgc ccattcagta tgatactgac tgtgggtttg   51240
ttataaatag ctcttattat tttgagatac attccatcaa tacctagttt attgagagtt   51300
tttagcatga agggctgttg aattttgtct aaggccttt cagtatctat tgagataatc    51360
atgtggtttt tgtcatttgg ttgtgtttat gtgatggatt acatttattg atttgcatat   51420
gttgaaacag ccttgcatcc cagggatgaa gctgacttga tcgtggtgga taagcttttt   51480
gatgtgcttc tggattcggt tttccattat tttattaagg attttcgcat cgacattcat   51540
cagggatatt ggtctaaaat tctctttttt tgttgtgtct ctgccaggct ttggttatca   51600
ggatgatgct ggcctcataa aatgagttag ggaggattcc ctccttttct actgattgga   51660
atagtttcag aaggaatggt accagctcct cttttgtacct ctggtagaat tcagcggtga   51720
atccctctgc tcctggactt tatttggttg gtaggctatt attgcctcaa tttcaaaacc   51780
tgttattggt ctattaagag attcaacttc ctcctggttt agtcttggga gggtgtatgt   51840
gtccggaaat ttatccattt cttctagatt ttctagttta tttgtgtaga gcggtttata   51900
gtattctctg atggtagttt gtatttctgt gggatcggtg gtgatatccc ctttatcatt   51960
ttttattgca tctatttgat tcttctctct tttcttcttt attagtcttg ctagcagtct   52020
atcaattctg ttgatctttt caaaaaacca gctcctggat tcattgattt ttttttgaatg  52080
gttttttatg tctctatctc cttcagttct gctctgattt tagttattc ttgccttctg    52140
ctagcttttg aatgtgtttg ctcttgcttc tctagttctt ttaattgtga tgttagggtg   52200
tcaattttag ctcttttcctg cttttctcttg tgggcattta tgtgctataaa tttccctcta  52260
cacactgctt taaatgtgtc ctagagattc tggtatgttg tgtatttgat ctcattggtt   52320
tcaaagaaca tctttattc tgccttcatt tcgttattta ccagtagtc attcaggagt     52380
aggttgttca gttgccatgt agttgtgtag ttttgagtga gtttcttaat cctgagttct   52440
aatttgattg tactgtggcc cgagagacag tttgttgtga tttctgttct tttatatttg   52500
ttgaggagtg ttttacttcc aattatgagg tcaattttcg cataagtgtg atatgatgct   52560
gagaagaatg tatattctgt tgatttggag tggagagttc tgtagatgtc tattaggtcc   52620
acttggtgca gagctgagtt caattcctgg atatccttgt taaccttctg tctcattgat   52680
```

```
ctgtctaatg ttgatagtgg ggtgttaaag tctcccatta tcattgtgtg ggagcctaag    52740
tctctttgta ggtctctaag gacttgcttt atgaatctgg gtgctcctgt attgcatgca    52800
tatgtattta ggatagttag ctcttcttgt tgaattgatc cctttaccat tatgtaatgg    52860
ccttctttgt ctcttttgat ctttgttggt ttaaagtctg ttttattaga gactaggatt    52920
gcaacccatg catttttttg ctctccattt gcttggtaga tcttcctcca tccctttatt    52980
ttgagcctat gtgtgtctct gcacatgaga tgggtttcct gaatacagca cactgatggg    53040
tcttgactct ttatccagtt tgtcagtctg tgtcttttaa ttggagcatt tagcccattt    53100
acatttaagg ttaatgttgt tatgtgtgaa tttgatcctg tcattatgat gttagctggt    53160
tattttgccc gttaattgat gtagtttctt cacagcatga atggtctttg caatttggca    53220 tgttttgcg gtggctggta ctggttgctc ttttcaatgt ttagtgcttc ctttaggagc    53280
tcttgtaagg caggtctggt ggtgacaaaa tctctcagca tttgcttgtc tgtaaaggat    53340
ttgatttgcc cttcacttac gaagcttagt ttggctggat atgaaattct ggattgaaaa    53400
ttctttcttt taagaatgtt gaatattggc ccccactctc ttctggcttg tagggtttct    53460
gacgagagat ctgctgttag tccgatgggc ttcccttttgt gggtaacctg acctttctct    53520
ctggctgcct ttaacatttt ttccttcatt tcaaccttgg ttaatctgac aattatgtgt    53580 cttgagttg ctcttcttga ggaatatctt tgtggtggtc tccatatttc ctgaatttga    53640
atattggcct gccttgctag gttggagaag ttctcctgga taatatcctg aagagtgttt    53700
tctaacttgg ttccattctc cccgtcactt tcaggtacac caatcaaatg tagatttggt    53760 tttttacat agtcccatat ttcttggagg cttttttcgt ttcttttac tctttttct    53820 ctaatcttgt cttctcgttt tatttcatta atttgatctt caaccacgat agcctttctt    53880
ccacttaatc gaattggcta ttgaagcttg tgcatgcgtc atgaagttct cgtactgtgg    53940
ttttcagctc catcaggtca tttaaggtct tctctacact gtttattcta gttagccatt    54000
cgtctaacct ttttcaagg tttttagctt ccttgcgatg ggttagaaca tgtttcttta    54060
gctcggagaa gtttgttatt accaaccttg ggaagcctac ttctgtcagc ttgtgaaagt    54120
cattctccat ccagttttgt tccgttgctg gcaaggagct gcgatccttt tcaggagaag    54180
aggcgctctg gttttggaa ttttcagctt ttcagccctg gtttctccct atctttgtgg    54240
ttttatctac ctttggtctt tgatgttggt gacctacaga tggggttttg gtgtggatgt    54300
cctttttgct gatgttgatg ctattccttc ctgtttgtta attttccttc taacaggccc    54360
ctcagctgca ggtctgttgg agtttgctgg aggtccactc cggaccctgt ttgcctaggt    54420
ctcaccagtg gaggctgcag aacagcaaat attgcagaac agcaaatatt gctgcctgat    54480
ccttcctctg gaagcatcat cccagagggg cacctgcctg tatgaggtgt ctgtcggccc    54540
ctactgggag gtgtctccca gtcagtctac atgggatcag ggacccactt gaagaggcag    54600
tctgttcatt ctcagagctt gaatgccatg ctggagaac cactgctctc ttcagagctg    54660
tcagtcaggg acgtttaagt ttgcagaagt tgtctgctgc cttttttca gctatgccct    54720 gcccacagag gtggaatcta tagaggcagt aggccttgct gagctacggt gggctctgcc    54780
tagttcgagc ttcccagctg ctttgttaac ctactcaagc ctcagcaatg gcagacgccc    54840
ctcccgccat gaggctgcag cctcgcaggt tgatctcaga ctgctgcagt agcagtgaat    54900
aaggcttcgt gggtgtggga cccaccgagc caggcacagg agggaatctt ctggtctgct    54960
ggttgctaag accatgggaa aagcacagta tttgggcaaa agagtactgt ttttccaggt    55020
acagtctgtc atggcttccc ttggctagga aagggaaatc tccccacccc ttgcacttcc    55080
```

```
cagttgaggt gacgccctgc cctgcttcga cttgccctcc gtgggctgca cccactgtcc   55140
aaccagtccc aatgagatga accaggtatc tcagttggaa atgcagaaat ctaccectct   55200 tctgtgtcaa tcttgtcgat cttgctggga gctgcagacc ggagctgttc ctattcggcc   55260
atcttggaag tgactgaaat tgttattttt atgtgttctc tgttttgctt cctcaccaag   55320
actctaaact ctggatggaa gtatatctgt tgtttataat tcccaatagt cttagtataa   55380
tcccttacac acaacgacca ttgtattgtg accaatgtag tagtaaaaat tggaaaagat   55440
tttcaataaa tattatgaca atgaatgcac gtgtgtttac gtgtatatgt acaagttaaa   55500
gttaccaaag atgattatag gtcagcaatg actaaaggtg actaatatca taatgactaa   55560
atatggcttg gtagggatag gaaaatcagc atcttaccca tttcctgcca gactcaaggt   55620
gaataagaga aagctaaaag attgccttgc cctaggagac aaggttaaga ccgagttact   55680
aggcttatgg tggtcataaa cctgcaaata ttctgagaag tcaaagtctg tttgacatcc   55740
ccatatggat attcaatggg catttcaaac ttaatgcttt aagaacaaac atcttaattt   55800
cccattgctc caacctcctt ttattcattt aacatatatt tattgaaggg ctactatgtg   55860
gcaggtactg ttttagtctt ggaatgtcca tcaatgggca taacaaagat ctctgccctt   55920
gtgttgttta taatctggca gggagaaaca ggcagtagat agtaaacaca gtaggtgaat   55980
tgttaagtgt tgtagaaaaa gcaacaaggt agaaaaaggg taagaggaac tgggagtgct   56040
ggtgggatgg gcttggggat agtgatggag agatgtaagt agcaacttca attggggagg   56100
tcaggatgac ctgactccat tgtcaggttg aaattggagc agagagctgg ggttgaggga   56160
gttagtcaag tagtaaggtt atccggggga agagcattcc agcaaaggga acaagtagag   56220
caaagtcagg aggtacttag agtatcccgt gaacagcaag gaggccatgt gtctgctgca   56280
gagccagtga tggagagagt ataaaaggag gtttaggaag gaaagctggg tgatggggat   56340
caaatcatac agggccttag gccactgaaa agactttggc ttttagtctg agtgaaatac   56400
ggggagtctc tgaactgttt tgaacagaga ataacatct gacttgcatt ttaacagaat    56460
tactctggca tctctgttga gtaaagaata taaaacggca agggcaggaa caggggaacc   56520
tgttaagagc aattgcagag gctgggcgca gtggctcatg cctgtaatcc cagcactttg   56580
ggaggccaag gtgggtggat cacggggtca ggagatcgag accatcctgg ccaacatggt   56640 gaaacccgt ctctactaaa aatacaaaaa tacaaaaaat tagctgggca cggtggcggg    56700
cgcctgtagt cccagctact cgggaagctg aggcaggaga atggcatgaa tccgggaggc   56760
agagcttgca gtgagctgag atcacaccac tgcactccag cctgggtaac agagcgagac   56820
tgtctcggaa aaaaaaaaaa aagagtgatt gcagaaatac atgcagagaa atggcagtgg   56880
cttgtacagg gccacagcaa tggacatgag gatgaacata ttttggattc tgaacatatt   56940
ttgaagttag agtcggcatg gttttctgac actttggata taaaatgtga atccaaggct   57000
ttttgcctga gcaactattt aatagaagaa tgaaagtgcc attaactgca gtgggaagaa   57060
ctgtgggtgg agcaggtttg gagaagataa gtagttcagt tttggatatg ttaagtttgt   57120
gatatccaag taaagatttt gaataggcag ttggatgtac aagtctggag tctgggaaga   57180
aatctaggct ggggacagaa atttgagggt tgtcaccctg tagatcatgt ttaaaaccac   57240
gggactgtat gagtttcatt ataccaagga aataagtagt aagagaagag gaccaaaggc   57300
agaaccttag ggatgccacc tctgttgcct tgttctctt tcatctttc agtaaatggc     57360 actactatct ccctgatttc tcaagcctaa aatctagaag tcgtccttga tttcttcctt   57420
ctacatccag acccgtcctc tttgtctcca ctaccaccaa cctagtccaa gtcaccatta   57480
```

```
tcttctaata catctccatg cttccccatt tgtcccccta cagtcatttt ccatccagca   57540
gtcagaatga tcttgacaga atgaaggtaa ttctaattgt atcacacctc tgtgcaaagc   57600
ctgccagtgt tctgcacagc aaacattgtg aatgaatgtt ctgactcaca aatcactgtg   57660
aaatattgtc caacgtgaaa cagagtgaaa aggcagccta cagaaaggaa aaaaatattt   57720
ttttcttaga ataaaatatt ctaataaaat attaaccccc taaaaagggg ttaatatcca   57780
gaatatacaa agaactccta caacataaca ataaaaaaca aataatctaa tttaaaaatg   57840
ggcaaaggac ttaaatggac atttctctaa agaagatata cacatggcca acaaacattg   57900
aaaagatgct ctacatcatg aatcatcaca tacccatgtt cattgcagca ttattcacaa   57960
ttaccaagag gtggaagcaa ttaaatgtca attgacagat gagtggataa agaaaagttt   58020
gtatatacaa aaaatggaat cttattcagc cttaaaaaag aagggaatcc tatcatatgc   58080
tataacatgg ctgaacctta gggatattat gctaagtgaa ataagccaaa aagacaaaat   58140
actgcatgat ttcacttata tgaagtatct gaagtagtca aactcttaga aacagaaagt   58200
agaaaggtgg ttgccaagag ccggggagag tggcaaaagg ggagttgttt ataatggata   58260
tggagcttca ttttttgcga gatgaaaatg ttctagggct gggtgcggtg ggtcacgcct   58320
gtaatcccag cactttggga ggccaaggcg ggcggatcac ctgaggtcag gagttcgaga   58380
ccagcctcaa catggggaaa ccctgtctct actaaaaaaa atacaaaatt agccgggcgt   58440
agtgctgcat gcctgtaatc tcagctactc aggaggctga ggcaggagaa ttgcttgaac   58500
ctgggaggcg gaggttgcgg tgagccgaga ttgagccatt gcactccagc ctgggcaaca   58560
agagcgaaag tccgtctcaa aaaaaagaaa atgttctaga gctctattgc acagcaatgt   58620
ggatatagtt aacactattg tactgtacat gtaaaaatgg ttaatatggt gaaatttgta   58680
ttatgtgttc tttagcacaa taaaacaaaa accaaatccc tcctgtggtt cctactgcac   58740
ttagaataaa atccccaact tcttgcccta gctgccaaag ctgtttatga tgttgttttg   58800
ccagaatccc tcgacctcaa cttgtgccat tcttcctttg tctgttattg tccagccaca   58860
gtagcttttct ttctattcct tacacttacc aaactttttcc ccctgccttt gaaatgttct   58920
tcccgctgac ttttaccagg ctagctgcat cttgttttttc agatcttgac ttaatgttac   58980
ctcctcatga aggcttttta taactaccta gtctctagtt gccaccaatc actagctgta   59040
tcacatcact ctacttaaat tttctaggcc gggcgcggtg gctcacgcct gtaatcccag   59100
cactttggga ggctgaggcg ggtggatcac gaggtcaaga gatggagacc agcctggcca   59160
acatggtgaa accccgtctc tactaaaaat acagaaaatt agctgggtgt ggtggcatga   59220
gcctgtagtc ctaggtactc gggaggttga ggcaggagaa ttgcttgaac ctgggaggtg   59280
gaggttgcag tgagccgaga tcgcgccact gcactccagc ctggtgacag agtgagactc   59340
agtctccaaa aaaaaaaaaa aattctgcat agcacttctc actatctgat attttttctta   59400
tttatatttg tttactgtct gcttccccta tgtaagaatt ctataagttt tttatatttt   59460
agaatttaaa gttttttaaat tttaaaagaa tgttacgaga aagcagggac cttgtctgtt   59520
ttgttcatca ccatatcccc aagcacctag aatagtgcct ggcatatact aggtgctcaa   59580
taaatatttg ccgaaagaaa actgaacttc ctagtcttaa atgatcattt cttgaaaagg   59640
actactcttc tccccaagct ccagacctgt cttttttgaat tccttcttgg gtatttctgt   59700
ctaaatattc tacaaatacc tcaaattcaa catgccccctt tctgctcaat tactcttaca   59760
gaccttatttt tttctgttaa tggcatcatc attagcccaa ttgatcaggc cagaggtcct   59820
ctttgattcc tttctttctc tcaactccca ctatctatca gatcctgtca gtatcttgtc   59880
```

```
tcacatctttt cccttctctt ccacagagtt gctaccacat cattttaggc ctaattactt    59940
tttacttgta tcattgtaag aaactgccta accgggcttt ttgcttccaa tcccccacgc    60000
ctttccagac catactgtct tctattcatc atactacttt tctgttcaaa actaacaaat    60060
gaaatgccat tttttttttat gctttggaaa gccacggaaa acttatcct cagcctcctt    60120
tagaccctac ttacctttcc agcctcacca ttcatgacat ccctgcagct ctgtgctgct    60180
gccctcattc tgtggcctta tcagcctcat agctggtggt cacatacacc agcagcctcc    60240
acctttacaa agccattttc cctgactgca gtgctcctga accccgctc cttttggctg     60300
acttacagtt ttatctttaa gatataacta aaaaactgcc tccccaagaa gcctttatag    60360
atcttccctc aactccaaaa ttgaaattag tggcatagac ccataatatc tctattatta    60420
atatcatttt tttctttttt tttccaagat aggtcttact ttgttaccca gactggagtg    60480
cagtggcgca atcttggctc actgcagcct tgaactcctg agcttaagca atcctcccac    60540
ctcaacctcc tgagtagcta tgatgacagg catgtgccac catgcccagc taattttttt    60600
gtatttttttg tagagatggg gttttgctat gttgcctagg ctggtctcaa actcctgagc    60660
tcaagcagtc tgcccaggct tccaaaatat ttattgagca cctactatat gccaggcact    60720
attctaggta ctgccctcag cctcccaaag tgttaggatt acaggcatga gccacctctc    60780
ccagcctatt tcattttttta aattgtggta aagtatacat aatataaaat ttaccattgt    60840
aactgttttt aagggtacaa ttcccttgca ttaagtacat ttacattgct gtacaacatt    60900
caccactgtc ctctgctatc atatttaatt atttatggat gtagttgtcc cctcctctga    60960
ttggaaacaa aacgcttggc gttatttgta agtgctgaat taacatggat gaacatgaat    61020
ataatcagat catctcctga gatgagatgt catgtcacaa gtatccttgt gatcctgctt    61080
gggtaacttc aggattgtgt tcagttttct tccttgtact tattcaaaat ggcattggtt    61140
agagttcacg gagtcctgga tttttaaagg ttctttgcct aatttcttct ttacaagttt    61200
ttggtgcgta cacttaacct aacttttttg tcttaccaat atctatccta taaatatgcc    61260
agtgaaatgg agcatattgc gttaggtaag gtgtgcatat ttcaagaact agatgtgttt    61320
caaagcacat aatgaaactt cagcaaaaat gagattaaga gttaggctc caataatatt     61380
gctgcgattt tatttctgtc aaagttttgt tattttgct gtattgtttg ctttcttca      61440
atgttttgta agccccggtt ctttgatgaa ctcctaataa gctgtgctta aaactatgac    61500
attgaccttt ctccagaaac aggtttcaga attgtctgtt tttcatgttc tctccctgcc    61560
ttttctcttg taatcaaatc agcatgtttt tgttttttgtt ttggagacag agtcgcactc    61620
tgttgcccag gctggagtgc agtggcacta tctctgctaa ctgcaacctc tgcctcctgg    61680
gttcaagcga ttcttctgcc tcagcctccc gagtagctgg gactacaggc acgtgccacc    61740
acacccagct aattttttgt attttttagta gagacagggt ttcaccatgt tgcccagact    61800
agtctcaaac tcctgagctc aggcaatctg cccgcctcca cctcacaaag tgctaggatt    61860
acaggcatgg gccattgcac ccagcctaaa tcagcatgta ttttttaaaca tcatagaatg    61920
cgagggtttg aagtgtcttt tgtgatcatc taacattcac tttgcatata aataaataaa    61980
taaagaccca tgttaatgcc aaagggagtg agtggcagaa gaatctatga cggaagcata    62040
tcttttggtg ctgtcaatga aagggaaaca aatgcttggc attatttgta agtgctgaat    62100
taacatggat gaacatgaaa ataatcagat catcagttat tctccctcct gatctgaagg    62160
atcctgtgtg acatcatctg agatgcactg ggggttgagg aaagatgacc cttaaaatcc    62220
acatttgtac tttccaagag caaggtgaga tcatagagaa gttacacccg ctccttctc    62280
```

```
cacttttag   tctttatcca   ctaaaaacaa   gatgtgagaa   aatcaagtga   caagaatgat    62340
agggtaatag   gctgtcaaca   aaatgagtgt   gtgggcttat   ataggtataa   acatggtgaa    62400
ggtgatagac   catggatgct   tagtcccttt   taagttccat   cttccgttta   acacattttg    62460
aaagaattta   ttgtgtctta   ttttcccctg   atttgtgtag   ctgtgccacc   ctagataaca    62520
gttttctttt   ttgctcttgc   caccttcttg   ataaaggcaa   gtacagttag   aatcgtaggt    62580
acttaataat   gcttcggcat   gaatatgctt   cacaactttg   agatgtgtac   cctttatttt    62640
ctttctgtta   taaatcttaa   tttctttgtg   ccctactttt   catatctgta   aaatggatga    62700
aatagtagta   tctgcctcat   ataattgctg   taaagattaa   atgctaatac   acataaagct    62760
cttagaacag   gtctggtgta   tagtaaacac   acaaagctgc   tattattatt   gttactggta    62820
ttaactgata   tattcatact   ttttataact   gctcatccta   ttaattaaat   gtattttttc    62880
actatatatt   cttttcaat   gtatattcct   tttaatcttc   cttcttagcc   tccactatag    62940
ttcagatgcc   ttctccaatt   tcaaacaatt   taatgaaaag   aaaagaaaat   ttatacatcc    63000
agagatggct   gatttaattt   cttcagtctt   ttggagggta   gaattatttt   ccttctgaga    63060
gtaaacttat   tttttctatg   ttacaggtgg   tatgcaagat   tacaattatg   tgtgggccaa    63120
ctgttttgag   atcacattag   aactgtcttg   ttgcaagtac   ccacctgctt   cacagcttcg    63180
acaggaatgg   gagaacaatc   gtgagtcttt   gatcacattg   attgaaaagg   taaaagtaga    63240
tgactggaat   gttggggtat   agaaacagga   ttaaataagg   gagaaatttg   gatgcatgtg    63300
aatgataatc   tatacagtat   tagatgtcat   ttatctcttt   ttattactta   agattataaa    63360
ttatctttaa   agattattag   attataatct   attaaaacat   attctagctc   tgcttcccct    63420
gccccttacc   cccagctctc   tgctccatag   ggcttccttt   tcctatcttg   gaacacttac    63480
ttatacaaac   tgaaataatt   agccaaattt   gtactctcag   gttcttacaa   tgtcatgtga    63540
tcatatttgc   tagtgagcct   ttaccactat   atgaaccata   gacatcagtt   taatttaaac    63600
atcacccaga   ctaatacagc   aattgaatac   accagcagtt   acaccttgtt   gagaaaatta    63660
gaaatctggc   tttgaggaga   gggaatttta   aaagcacctt   actagtgtcg   agttcagaca    63720
tatgacttaa   gtttaaggat   ttaatacttc   tgtctgtatt   ttatttaaac   ttcaagggat    63780
tgaaaatgtt   ttggggggaga   gagaagagtc   acttttattt   ttagaaattc   tagtatcggt    63840
gcagagagaa   attatgcgct   cttgccttcc   aaattcaccg   tctctgagct   tggattcttg    63900
tcttcttagg   ttcacattgg   agtgaaagga   tttgttaaag   attccataac   aggatctggg    63960
ttagagaatg   caaccatctc   agtggctggt   attaatcata   atatcacaac   aggcagattt    64020
ggtgatttct   accgattact   tgttcctgga   acttacaacc   ttacagtagt   tttaactggg    64080
taagaattta   aactatgtag   actcttagtt   aaaatgtcaa   gtctctgttt   tatatctgag    64140
acagaaatat   agtctagtac   atgttgttta   tttttttgtgg   cttttatttt   tccttatttt    64200
ctgatttttc   tcgttttata   ataagaaaat   actattgtgg   agttttttgt   cacatagtct    64260
aatagtacaa   tgggatgtga   agcatagttg   tagcattaga   ggaaggacaa   tttttaaaac    64320
ttgaaaagat   attcagctgt   gtaaagcatt   gccttaaagc   taaccgaata   ccagagtaga    64380
agaaacccat   tgctctgtaa   atgacatttt   gaagaactgt   cttatcagct   ttctaatata    64440
ttaaatgaat   ggtttcccac   ctcccctgga   aagcttctg   gaagctcact   ttgataagga    64500
tttaattgat   aaccttttaat   cttgagcttt   cctacttgaa   aaagaagttg   gaatgtcagt    64560
ttgataagac   actgcaaaga   attgtgtaat   ttatcccttc   tttgagtact   gtagcagtgg    64620
ttacaatgga   gtaacaacca   catcttcaa   catgttcttt   cctttgagtg   taattttttt    64680
```

```
ggtatacatt ctagtgtgtg gtacttgaga agatttggtg agagaaatag ttgttcaatc    64740
tggggttctt tgtgagataa tgtcctaaaa ctcttaaatt tacacatctc tctttattta    64800
gtttgagttt tgatagatcg ctaagtgtaa gaggatgaaa aggctactgt gcttttataa    64860
tattaaagca ttgtatgtct taactataaa ccatttactt tttcaaattt ttttttcagg    64920
tatatgccat tgactgttac taatgtagtg gtgaaagaag gaccagccac agaggtggat    64980
ttttctctta ggccaactgt aacttcagta atccctgaca cgacagaggc tgtatcaact    65040
gctagcacag ttgctatacc taatattctt tctggaacat catcctccta ccagccaatt    65100
cagccaaagg actttcacca ccaccatttc cctgatatgg aaatcttctt gagaaggttt    65160
gccaatgaat atcctaacat tacccggctt tattccttgg gaaaatcagt agagtcaaga    65220 gaacttatg tgatggagat atctgataat ccgggtgtcc atgaaccagg taattggtat    65280
ggtcttacac ataatttcag tagtgcccct caaagccatg ttcaatattg ctatgtttca    65340
ttcagaaagg tcgcctacag tttgtataac tggcattaag aaaacctaac taaaattaaa    65400
agaaagcaaa aagaaaatg taaccaatct tttcccagaa gagaaggaaa tccttttgct    65460
aacccatatt aggcatggta tttaataagt gcatagatta gatttattct gctaatagtg    65520
ttttatttat ttatattata tagcatatat atgctttgag cctgctcaga catatgtatt    65580
agtaaggaag ctgctttata agatgtttct gaaggttttt tctgcctcct ttgccaaaat    65640
acatgtttaa aaaattttt agtataggat ttatatatgt tgcggaaaaa aactgagtcc    65700
atgatgatta agaaggaaaa aaagccttcc atgtaattat tttgttttca ggtgaaccag    65760
aatttaagta cattggaaat atgcatggaa atgaagtggt tggaagagaa ctgctgttga    65820
acctcataga ataccttgt aagaactttg gaacagaccc tgaagtcaca gatttggttc    65880
ataacactag aattcaccct atgccatcca tgaatcctga tgggtatgaa aagtcccagg    65940
aaggtaaaga atagcattta attcttaatc atttgatcat catatagaat gattattttg    66000
atggagaaga gaatttgaac tggttctttt ggaatttctt ccaatttttt ttccttttaa    66060
tttatgattg attttagctc ttgtattctt atatgatgat ctggtctgtt caacaattag    66120
gtgatcaaat ttatatattt agtggtgtct tccacttggt aatggttcta atttactaga    66180
aatagagtat aagactttta taaattgttt tattttagca atagttctgt tgacaaagag    66240
tcaaactctg taaaatattt gaagagattt attctgagcc aaatatgagt gaccatggcc    66300
catgacacag ccctcagacc cagaggacat gtgttcaggg tagtcagggt gcagcttggt    66360
tttaaacatt ttaagaagac atgagacatc agtcagacac atttaagata tacattggct    66420
tggtccagaa atcgggcgag ggttgaaaga tttattatca atcgaaagga atgtctgggt    66480
taggataaga ggttgtagtt accaaagttt gatcatgcag atgaagcctc caggtagcag    66540
gcttcacaga gaatagattg taaatgtttc ttatcagact taaggtctgt gttggtatta    66600
atgctgattg acttttcctg atttccaaaa gagaggaggc ataatgaggc atgtctgacc    66660
cccatttccc atcatggcct gaaccagtct ttcaggttaa ctttggagtg ccgtggtcaa    66720
gaggagggaa tctgttgaga taggccctgc ctattgagcg gggccttaga atttgtttt    66780 gggtttacag ttcttattaa atcattattt tgggaacctt atttcataag tgaaaaacca    66840
aaccagatat ctgtctgagt cagtgactct gttttgactc tcagttctac tccctctgca    66900
tattccagac ttgctaattt attgacttct catttctttg ccttccctgg gcaagcccat    66960
ctctcctggg gcgttatagt gtgggatggg acagcagacc cttatgcaca acactagggg    67020
agtaagaatt catcttttcc cagcccatga tttcttccag gcaatgatat ctatcaggca    67080
```

```
ccatagtata atatggagcc tcatgactta ttactagcac tgacctgacc attgggagga    67140
tcagttggtc attagttggt cattagtacc cagaagttgg tcattagtac cccagaagct    67200
cacttgaaca aataggcaca agatcttact tatatatgta tatatttcag attttccccc    67260
ctaaggttct cattctttgt cagtgccaca agtcccttct acatactccc cagacctttc    67320
tgaaaggtgg aactaattac actagtgagc cctccagttt tctttagtct cttgcaattt    67380
ttctcattat aatgacaata gtaaggctcc cactccctat aaaatggaa tatgcacagt     67440
taagcttaaa ttgaactttc tcctccatca ggttaaactt ccagctgtgc tcttggctaa    67500
ctttaccttt ttgtgatcac tttaatgtga gcatatcaca atttctttt catttgctct     67560
atttcttaca atgtcttagt gagctttata caagtacaga gaggagtata gagttcctgg    67620
ccaggcgtgg tggctcatgc ttataatccc agcactttgg gaggtcgagg tagatggatc    67680
atttgagacc aggagttcaa gagcagcctg gccaacatgg tgaaaccctg tttctactaa    67740
aaatacaaaa aattagctgg acgtggtggt gcacacctgt aattccagct actcgggaga    67800
ctgaggcaca agaattgctt taacctggga ggtggaggta gcagtgagcc gagatggcgc    67860
cactgcacta cagtctaggc cacagagtga gactctgtct caaaaaaaaa aaaaaaaaca    67920
aatagagttc ccctctgatc agtaatttcc actcaacatt gtgataatgt cattatatgt    67980
ggattattga cacttaaaca gtgctttaat ataatttgtc taattggaat attttttcctc   68040
ccagattatg agcagagggc aaaaataaaa agataatggt tttacctctc tgttcaaaat    68100
atctggaaga gatacagttt ttaaacacgc aatgtgaaaa agatgtgttt taactgtaat    68160
gcctggccag gtgctgtggc tcacgcctgt catcccagca ctttgggagg ccaaggtggg    68220
tggatcacga ggtcaggagt tcgagaccag cctggccaac atggtgaaac ctcatctcta    68280
ctaaagatac aaaaaattag ctgggcgtgg tggcgcacac ctgtaatccc agctactcgg    68340
gaggctgagg caggagaatg gcgtgaaccc aggaggcaga ggttgcagta agccaagatt    68400
gtgccattgc actccagcct gggcgacaag gcgaggctcc gtctcaaaaa aaaaaaaaa    68460
aaaaagaggt aatgcctgac aggttcttcc tgcctgctgc acaggcaaaa cagttcattg    68520
agaccatggt atcgcagtaa agagtttaat taatgcaagg ccagccacgc aggagaattg    68580
gagttatcac tcaaatcagt ctccctgaag gctcagaggt tagggttttt caaagatagt    68640
ttgatggaca agggactaga gaatgggttg attggttggg gatgaaatca tagggatgtg    68700
gaaaacagtc cttatgtgct gagtcagctt ctagttggga accacaggac cagctgagtt    68760
acaactcact cactggtcca ggtgacgtca gctggttgtc agaaatgcaa aagtcagaat    68820
aacatctcag aaggccaatc ttaggttcta cagtagtgat gttatctaca ggagtagttg    68880
aggaagttac aaatcttaac aacttccaaa acaatgactg gttatccttt aattacacat    68940
acatgttagc caaattcagg cccctcttat aatcccaacc ttgtgacctt tcattagttt    69000
tacaaaggtg gtttagtttt gggaaaggtt gttatcatcc ttgctttaag attaaactgt    69060
aagctaaatt tctcccaaag ttagcttggc cgatgcccag gaatgaccaa ggacagcttg    69120
gaggttagaa gtaaggtgga gtctggctgg gcgtggtggc tcactcctgt aatcctagca    69180
ctttgggagg ctgaggggggg tgggtcacct gatgtcagga gttcaagacc agcctggcca    69240
acatggtgaa accccatctc tactaataaa tacaaaaatt agctgggcat gatggcaggt    69300
gcctgtaatt ccagctactt gggaggctga gatgggagaa tcgcttgaac ccgggagatg    69360
gtggttgcag tgagctgaga ttgcgccact gcactccagc ctgggtgact gagtgagact    69420
ccatctcaaa aaaaaaaaa aaggcggagt caaccatgtc agatttcttt tactgttata    69480
```

```
attttgcaaa gacagtttca taatcatagg tgattgataa tagcgaagcc tgatgtgttc  69540
acatttgcct tgagttaagg tatctaaagt agtacgtgtt ggaataaaat ataagtgaac  69600
atggcttata ttcaaatcct ttatcatatc atacaggaga ttcaataagt gtaattggca  69660
gaaacaacag caacaacttt gacctgaacc gaaatttccc agaccagttt gttcagatca  69720
cagatcctac gcaaccagaa actattgctg taatgagctg gatgaagtcc tatccatttg  69780
tactttcagc aaacctgcat ggaggtatgg caactttata ttctactaat cagttcttgt  69840
tgagagcatt tggaaatcct ggtggaattt tatctgtttg tagtgttatg ctttcttaaa  69900
atgagtatcc tgttactgct cttatggcag acaacagtaa aggtcttttc tcattacttt  69960
ttcagccagt gtcctggctg tttctttcct ccttctttct ctcttttttt cctcctcttc  70020
tcttctcctt ttaccccat ctcttctctc cacccctttc tcctctcttt tctcacctac  70080
tacttctctt tcccttctct tacctcctct cccctttctt ctctgtcttg tcttttttct  70140
cctctcctct ccttctcccc cgcctgtccc cctactctgt tcttcctcct cctctcctct  70200
tcctctcata gttcttcagg tattttgtat ttatctctca cattgggaac ttggtaacat  70260
attctttgtc attcataaaa attgatccaa atgtttagtt ctgttttctc cctgaagttt  70320
aataaactct tttatgtaaa tttagattt gatattctct tttttacttg gtatatcctt  70380
aactgcagca gagtgaccac attctcatgt agtacctgag ctcatatacc tccatataat  70440
ttagcaggat ggatcggttg aataggatga gtgtcaagat taaaaatcgc cacaatgtcc  70500
aactaaggtt gcgaataaga gtgaagatat cagtacccaa gagaaccaaa ctgtgtccac  70560
acataaactc acttgaacaa aatgttcact catttaatgt acagtgctca tgtatatgaa  70620
tgttcaatgt acatgaacgt tcattcagga ttattcacaa taacaaaaaa gttgaaacaa  70680
cccaaacaac catcatctga taaatagata aataaaatgt ggtctgtcct tacaatgaat  70740
attatttggc tcgaaaagga atcaagtgct gatacatgct acaacataga tccttgaaac  70800
cttacactaa gtgacaaaag ccagtcataa tagaccacat agtgcatgat tattattttt  70860
ttctttatca agttgattat attttatga aattttaga ataggcatat ccatagagac  70920
aggaagtaga ttaaagattg tattgggctg gagtgaatag tggtaagagg tgatagggga  70980
gtgactgcta atggattttg gggtttcttt ttggagttat gaaaatgttc tataactgga  71040
tagtggtagt ggttgtacaa ccctgtgaat ataacaact ttaaatgggt gaattgcatg  71100
gtatttgaat tacatcagta aaactactaa aaaaaaaaa gtgacaagta ttagcaccag  71160
gggcaatggg gaagaaattt agtttcaaca tttactggaa tatccagaag taccatagtg  71220
gagacttcat gtcatataga gtagcctgcc attttagaat gacagtacat actgatggat  71280
atttagattt aggaggttaa ttgagattct ccaaaaattg ctttgaaaga ttgccaatag  71340
tagaaaaaag tacttctaca gttggtaatc atatattgtt ctcaaagagt caaataagaa  71400
ctatgaagtt atacccctggt tggcaaaata aattttttgt tttcttttat tatattttat  71460
gtgtttaatg ctatgtttga taaaattcac ttatttagag ctttaaaaat agtctcataa  71520
taaatcacac atcatgttgg ctaaatctgg aaagttaata atagttacat tccagtgaaa  71580
ataagtcaca gatttacaga tgtggtgtcc agaccttggc atggtgagag gtaggaatct  71640
tcagtcatgc agacattttt cttccatga catatttgt tttctcatct taaaatcctt  71700
atttaaatgg agtttgaaat cttggcaaag cagtttgaag gagaatttct tgttgctgt  71760 acaggagtaa aaaatcctca tagagtccgc agctggagct tgtgaattaa gctgataaaa  71820
gacagattaa aagaaaaaag catacaaatt ttatttgatg tttgtatgtg gcacaggcaa  71880
```

```
caggcagtgg gggagttcat aggaaagacg tgaaaccctc aaaaaagcag tgttaaggac   71940
ttagtgctct tataacaaag ggtaatacct tgtggaaaag tgactacaca aaggaagggg   72000
tttagacttc taggggtaaa aaattgtggg aaagtgacta ggaaatatgc gggggaaact   72060
aatgaaagat gagggttatt ttactaaggt ttgtttgtgt caactcatct tggtgttgac   72120
tatcccatct ctgatggtac caggaaggtg cctttctcac gggaaattta tgccctaatt   72180
ttaggcagaa agagggaggg tagatagcct ttcctgcatc tgctgtttct cagttgcctt   72240
cagctctaaa taattaacat gctaaagagt tatattctgg ggcagaatgt tctgattcct   72300
ttccctgcca tctttataat ttagaaggat cttgaaagaa gataggggaa agcaatattc   72360
tttttcataa aatttcaaaa attttgatac taatttttt attgaggtga agtttacata   72420
attccagtgg cgtttagtgc attcatagtg ttttgcaacc acccctcta tcttgttcca   72480 aaacattttt atctccgcaa aaggataccc cacacccatt taacagtgac tccccttcc   72540 cttctcccct caacctctgg taaccaccaa tctttgttct gtctctaggg atttacctat   72600
tctggatatt tcatagaaat ggaatcctat aacatgtgac ctttcgtgtc tggcttcttt   72660
catttagcat agtgttttca aggttcactc atgttgtggc atatatcagt acttcattcc   72720
tttctatggt tgaataatag tacattgtat atacatatgt atatatcaat atcacatttg   72780
ctttatccat ttacgtactg atggacattt ggttgttttt gacttttga ctacaatgaa   72840 aaatgcttct atgcccattg gcattcaaat atctatttga gttcctgttt tcttttcccc   72900
gtgcccccct tgttttgaaa cagagtctca ctctgttacc caggctggag tgtaagtggt   72960
gtgatcatgg ctcactgcag cctcaaactc ctgagctcag gcagtcctcc cacctcagcc   73020
tcccaagtag ctggaactgc aggcatgcac caccacacct ggcttatttt taattttttg   73080
tagagacagg gtctcccagt gttgcccagg ctgatcttga actcttgggc tcaagcaatc   73140
cacctgcctg ccttggcctc ccaaagtgct gagattatag gtgtgaacta ctgtacgcag   73200
cccctgtatt cagttctttt gggtgtacac ttaggagtga aattgtcata tgataattcc   73260
atgttaagct ttttgaggaa ttgccaaact gttttccaca gaggctggac tattttacat   73320
tcccgccagc aatgtatgag gttccagttt cttcatatcc tcaccaccac ttattatttt   73380 ctattttat tattatagct gtcctagtgg gtgagaagta ggacctcatt ttggttttgg   73440
tgtgcatttc cacaataact aatgatgccg aggatctttt catgagcttg ttggccattt   73500
atctatcttc tttggagaaa tatctgttca agtccttgt ccaattttta attgagtttt   73560
tgtctttgtt gttaagttgt aagagttttt aaatactgga cactggaccc ttatcaggct   73620
tgcaaaacat tttcccccat tctataggtt gtcttttctc tttcttatgt tcttgatgca   73680
taaaagtttt tgattttgat ggaatcccgt atatctgttt ttttcttttg ttgctagtcc   73740
tttccgtatt gatgctaatt atttttttga ggtagactgt ttggtagaag tactataaat   73800 cttttttgt ggcttagaa aattagccat ttgaaagata tcttctcact tattcacttt   73860
gaattgaaga aattagtgta attttcattt ctgttgagga aattctgctt ggcaaatttt   73920
attgttttct cttctctggc agtattctga aaagctttat gttaataatc catcttgaaa   73980
cagacaacat gatacatttt cctctttcc cttataggtt ctttggtggt taactaccct   74040
tttgatgatg atgaacaagg acttgccaca tatagtaaat caccagatga tgctgtgttc   74100
caacaaatag cacttctta ttccaaggta ggcttgtctt tgaatataaa atgttacaaa   74160
attaattctt ttatttaaaa atatgcttta aagtcctgca agactcaggt caagtgcttc   74220
catagttaat aaagcatgac ttttcagct gttttccgaaa aatagctttt tctcctgttt   74280
```

```
cccacctcac ttttgaatac actacatgtc tttctccatt ggccttttat ctatggtttt    74340
agcacagtac ctggaacata tacatgtcaa tttatttcat ttgacaaata agttataagc    74400
ccagtaaagt aggccaagat aagggcttaa tgaattatag ctctggagcc aaatcttgcc    74460
caccacctgt ttttgtaaat aaaattgtat tgacacacag ccacagctat attttatat     74520 attgtgtgtg gctgctttct ccttcaacat ttcaaagtaa gtcagtataa tttactatat    74580
taacaaacta aagaaggaaa atccagtgat caaagggcaa agttgggtag tttcaacaaa    74640
gacttttgca tctaaaaagt ctgaaatatt tgctttctgg ttttttacag gaaaaaattg    74700
ccaaacttta gtctaaggta tttaagatcc tgtagttaca tatagcaagg aaaagcaggc    74760
agaaatttct gtattttcca aacttcctat gataaacatg gattactctt acaatcggga    74820
atgttaaaat gtgtgtgtgt gtgaaaattt aatttaaaaa tcgttcttag gaccaggctt    74880
ggtggctcat gcctgaaatc gtagcacttt ggtagggcaa ggcaggagaa ttgcttgagc    74940
tctcaggagt ttgagaccag actgggcaac atagcaagag cttgcctcta ctaaaaataa    75000
aaaataaaaa aaaaattagc cggttgtggt gacatgcatt tgttgttcca gctacttagg    75060
aggctgaggt gggaggattg ctctatccca ggagattgag gttgaagtga gcttgatcac    75120
aatactatac tctagcctgg gtgacaaagc tgagaccctg tctcaaaaaa ataaaaattg    75180
tcttagaaaa catgttaaaa gttgaggctt gtaaactaag cttgttagtt tcaatgtttg    75240
gtgttactac tgacttagta ttgttattgg ttatattggt actattattg gttataggta    75300
atgaatatta ttactgtaac tctgcactct ccagtcacag tcctccatcc ttccactttt    75360
cccattccct catcctctgc aaatgaatct tgtgagattg ttcagagttt ctactagagg    75420
agtacagctg ttcatttcac cttagagaat tattgctttc tgtttggaca tatatgtttt    75480
tttgaagtac atacgtggag taataagaga atgtatagtg tcccaaccat caaaataaaa    75540
attaaatggc tggattttgc atattttctc atcacattct atgctcattc tcatgatttc    75600
tgcttttcgc cttcattttg gcttctagtt ccttatcttc tctttgtttt cttagaccat    75660 taacccttt gatttgattt accttttctct gtagggtaga cccatggaca tacctttca    75720 atgattctcc taagggtctt gtacaccct ttgacataac tgctttgccc tccagtcctc    75780
agtaattacc attatctctt ttctccatac caatattaca agtacagcct agagtggtca    75840
cactgtcacg gcaatttgct atagtccata tgtgtgctct ccaacttcag ctgaaccctc    75900
agtcctacat ggcaacattt cctgtttagc tacttgactc cctggctcag ttcccactat    75960
ggtgattcag agcctttatc ctctatctga gcctcctgtt ccagctctat ccctcttatt    76020
catagtagat cactttgcat tgaactcaag tagaactttg agtaatctga tgtgagttca    76080
ctaagattct gtcttctcaa ttgtttctca tgtgtgtctt aacaatattc tcctccattt    76140
cttgatccca ctgcattctg cctcctcgaa tcttgtgtct tcatatctta ttttataaat    76200
gaggaaggtg ataattaaac tccccagtct tcactcacag cctttttct cttggtcaat     76260 aagcagctcc tctaaaaata ttgtcttctg ctaaccttag taagcccca tgaagctacc     76320 attcaaagtt tctttatttt tactcttcaa aacttctcaa aagtagatag tcttgggaga    76380
catctgagca gccaaagaca atgatggcta tgtgataacc tatctcccag ggttttcctt    76440
taaacaatat aaaacgactt aaaaactacc aaatttaca caaaaccaca ctgttggcat      76500
cacaaaagat cctgaaactg caaataact gtaaattttt taaaaatcaa gaagtctcag      76560
catgatctat catgcaccta ccccacccttc gccccaccac aaggctttgt ggtgaggtaa    76620
aacagaccaa gaaaacttac ggagaagaca gaagtgggtg ccagtgaagg gcagctgtga    76680
```

```
aggtaatttg gaatgaccac catacatcac atatgcacta aatccaaaaa tactaaaaga    76740
gtaactgggc agattagagc tctggaatac agggaagaga tttcaaaatg cacacaactt    76800
aaaggatctg gtgtgattta atgggataag tacaatttaa aaggagagga tggttacagg    76860
gagatcttcc aaactcatag cttctggaga aggaaaaaaa gaggcaaaga tagaaatgaa    76920
gaagtgctcc ttggcaatta gatggtgaat gggaaaagga aaaagtgggg agaaatgtaa    76980
ggttttacaa gacagaaaag aactttaaaa tcagaagatt ctcagctcca cccttaccac    77040
caagacaaat aaataaccac actgaggtac ctggattttg ctagaccgac agaaagtgt     77100
accattaagc taggaataat attaaatgcc aatatcata aaaataaaga ggaaaataaa     77160
gtccatggaa aatgattgca gaaaattagg aaatgaaact tcacatatag acactaagga    77220
gaccctacca ttagcaaaaa ataatcgaga agcagaagaa aactgttcag ttggcattct    77280
aaacagatta agtatacca aatatacgtt gagaatatga gaaactacct caactcagat     77340
agtcaaaaaa taaaacaga ggccaggaaa caaaaaacag ggataaataa ataaagttt      77400
ataggactca ggaaaaaaat ggaagaaaaa gacaaaatta tctctgaaat gaagaataaa    77460
tgacaaaagt tagggaactc atacatccaa tttcaaactt actacaaagc tacagtaatt    77520
aagacagtgt ggtactggca taaagacaga catatagatc aatgaaatag aactgagaac    77580
ccaggaataa attcttatgt tgatggtcag ttgattttt tttttagaaa aggatgccaa     77640
gacaattcaa taggcaaaga atagattttt taaataaatg gtgctgggac aattggatat    77700
ttatatgcaa aagaataaac tagatacctt cctcacacca caccccaaaa ttagcttaaa    77760
ataggtcata aacctaaata taggaactaa aactataaaa ctaagaaaaa ataggaatac    77820
attttttgtga tttggtcctc ctctagatat gacatcggaa gcacaagtga caaaaaaga    77880
ttgatacatt ggacataatc cagatttaaa acttctttac tgcaaaaaaa aactgtattt    77940
gtttcctagt tctgctgtaa caaaattcca caaactgggt ggtctaagac aacaggaatt    78000
tattgtctca tagttttgga ggccagaagt ccaaaatcac agtgttggca gggccattct    78060
ccctctgaaa ctgtggaaga atccttcctt gtttctccct agtttctggt gctttgctgg    78120
caaccattgg cattccttca cttctaggtg catcactcca acccttcatc atcacacggc    78180
attctccctc tgtcttcgta tcccagtttc cctttgtac aaggacaccg tcatattgga     78240
ttagggccca tgctaatcac cttattttaa cttgattacc tctgtaagga acttattttt    78300
aaataagatc acattttgag gtactgaggg ttaggacttc aatatatttt tggaggacac    78360
aactcaatcc ataacatata acatccagga agtaaaaaga caacccacag aagctgggct    78420
tggtgacacg tgcctgtagt cccagctact gggaggctg aggccgaagg attgcttgag     78480
cccaagaagt agaggctatc gtgagctatg atcatgccac tgcactccag ctttggtgac    78540
agaaggagac cccagccccc aaaaaataaa taaatagatg acccacagaa taagagaaaa    78600
tttttgtaaa tcatatattt tgataaaggt gttatatcta aatatataa agaactctta     78660
tggctaaata ataaaagac aaatcatcca agtgaaaaat aggcaaagga tctgaatgga    78720
catttctctg aagaagagaa aatggccaat aagcacatga aaagatgctc aatattatta    78780
gccattagag aaatgcaagt caataccaca atgagatacc tcttgttacc cactagaatg    78840
gctgtaattt taaaaatgg aaaatatgca taggcaaagg tggaaaaatt gaaaccttac     78900
atacattgct ggtggggtgt aaaatggtat aactgctttg aaaaacagtc tggcagtgct    78960
ttaaaacatt aaatatagaa ttgtaatatg acccagcatt ccactgctag gtatatacccc    79020
aagagaaatg gaaacatgta ttcacacaaa aacttgtaca tgaatatttg tagcagcatt    79080
```

```
attcataata gccccaaatg gaagcaacca aaatgtccat caactgatga atgggttaac    79140
aaactgataa gtagacatac aaaatcatac agtggaatat tattcagcca taaaaagtaa    79200
tgaagtaatg atacacagta caacttgaat gaaccttaaa aacctactaa gtgaagaag     79260 tcacaagaga ctacatattg tatgattcag tttatatgta atgttcagag taggcaaacc    79320
catagagaca gaaagtagat tggtggttgc ctagggtttg gagtgggggt ggggagtagg    79380
ggttggggaa aaatggagaa tgctaatagg tatagagttt cttttggg tgatgaaaat      79440 gtcctaaaat ttattatggt gggtggttat acaactctat gaatactaaa aaccattgaa    79500
ttgtacactt taaatggagt caatgtgtgg aatgtgaatt atatctcaat aaagtggatt    79560
ttgaaaacct aaagaagact gaggggtgga ggatccattc tgtattcgta tataagttaa    79620
aaaaatgaga tctaaaagtt ataccaag cccggtgtga tggctcacac ctgtaatctc      79680
aacactttgg gaggccgagg tgggcagatt cgttgagccc aggagttcga gaccagcctg    79740
ggcaacatag tcaaacccca tccctacaaa aaatacaaaa attagccagg tgtgtgggtg    79800
catgcctata gtcccagctc ctcaggaggg tgaggtggaa ggatcacttg agcgtgggga    79860
gattgaggct gcagtgagcc tgtgtttcca ctactgcact ctgagctggg tgacaaacaa    79920
gacccagttt caaaaccaaa acaaaaccaa aacaaaacca aagcaaaaga gcatgcatat    79980
aattattaca gtaatctaaa attatggttt ttatttgata agagagtgat gggatgataa    80040
gcctataatt ggcatattaa gttctagat ggggatcgtt tattttattt tgttttgtt      80100 aggacagagt cttgctttgt cacccaggct gtagtgcagt ggtgcaatca tggtttactg    80160
cagcctcaac ctcctggggt caagctattt tcccatctca gcctcccaag gagctggttc    80220
tacagacatg tagcaccatg tgtggctttt tttttttttt tttttttttt gtagagatga    80280
ggtctcactg tattgcccag gctggtcttg aacttctgag ctcaagcagt tctccaacct    80340
tggcctccca agtgttggg attacaggtg tgatcttacc tgtccctgtt tatatatttt     80400
aaatggttaa ttctctgtgg tagaaaaatg ggaaattatt cttttctct tcacactttc     80460 agtacttttt ttctgtttca aaagagata aatgaagttt tgaccatctt tcaaagctca     80520
atttcttcta ggaaactccc cctgccactc tcatcagatg taatctttct ctcctcttgc    80580
tttcaatggc atgcatttgt gtctccatgg cagttttct taccccttcat tgagttatca    80640 gttggacacc tactgtatgc tagatgctga ggacacagag acacaaactg tttcaaggaa    80700
tagtgtattg tctttaggga agagaaaggt gcaactagtt gtaatagggt aagataattg    80760
tacagagggc agtcagagca cagagggcc atcttattcc tgctagcagt cagggaaagc     80820
tgcttgcttt tattgtgtgt gtattatctt ttttggactt caagctcctt gaaagcatga    80880
aacgaaagta taaatatgag cagaaatttt ttttagagag gggttcagct aggttttata    80940
ttacttgtaa ttgcgagtaa taaatgaagt caatattttc ttacggagca cattgtattt    81000
tgatttttaa aaatagataa gttcagatag tgaaaaatca aaatggcata aaaagctata    81060
cactgaaaag tctcactgct catagcccca ccccactccc acctccaccc ctcacatacc    81120
ctgttggaag ccactttat tattttcctg tatcttccca gtattttttt ttgatggaga    81180
tacaaacaaa tagaagtaaa gattcttttt gttttccag gaaaattccc agatgtttca    81240
aggtagacct tgcaagaata tgtatcctaa tgaatatttt cctcatgaa taacaaatgg    81300 agctagttgg tataatgtgc caggtaaaga ttctttata tcaaggcctt acaacttgat    81360
ggcctttctg ctttcctaga tggtgcttct tgttattatc ttttagtttt gaggaataat    81420
aattattttt aaaacatggt ttaaatagtt taaaatattt aaataatctt ttcaactact    81480
```

```
tttatgtttg atgtacgttg agggttgagt aagaataatg cactaaaact tgattaaatg   81540
gttacatttt acttctggct attagaaaga atcttacatg tgctaataga agagtgtaag   81600
ctatatttga attcttttt ttctttacaa cgttactttc ttttttttt tttctttct    81660 tttttatta tactttaggt tttagggtac atgtgcacat tgtgcaggtt agttacatat    81720
gtatacatgt gccatgctgg tgcgctgcac ccactaactc gtcatctagc attaggtata   81780
tctcccaatg ctatccctcc ccctcccc caccccacca cagtcccag agtgtgatat   81840 tccctttcct gtgtccatgt gatctcattg ttcaattccc acctatgagt gagaatatgc   81900
ggtgtttggt ttttgttct tgcgatagtt tactgagaat gatgatttcc aatttcatcc   81960
atgtccctgc aaaggacatg aactcatcat tttttatggc tgcatagtat tccatggtgt   82020
atatgtgcca catttctta atccagtcta tcattgttgg acatttgggt tggttccaag   82080
tctttgctat tgtgaataat gccgcaataa acatacgtgt gcatgtgtct ttatagcagc   82140
atgatttata gtcatttggg tatataccca gtaatgggat ggctgggtca aatggtattt   82200
ctagttctag atccctgagg aatcgccaca ctgacttcca caatggttga actagtttac   82260
agtcccacca acaatgtaaa agtgttccta tttctccaca tcctctcctg cacctgttgt   82320
ttcctgactt tttaatgatt gccattctaa ctggtgtgag atggtatctc attgtggttt   82380
tgatttgcat ttctctgatg gccagtgatg atgagcattt tttcatgtgt ttttggctg    82440 cataaatgtc ttcttttgag aagtgtctgt tcatgtcctt cgcccacttt ttgatggggt   82500
tgtttgtttt tttcttgtaa atttgttgga gttcattgta gattctggat attagccctt   82560
tgtcagatga gtaggttgcg aaaatttct cccatttgt aggttgcctg ttcactctga    82620
tggtagtttc ttttgctgtg cagaagctct ttagtttaat tagatcccat ttgtcaattt   82680
tgtcttttgt tgccattgct tttggtgttt tggacatgaa gtccttgccc atgcctatgt   82740
cctgaatggt catgcctagg ttttcttcta gggttttat ggtttaggt ctaacgttta    82800 aatctttaat ccatcttgaa ttgattttg tataaggtat aaggaaggga tccagtttca   82860
gctttctaca tatggctagc cagttttccc agcaccattt attaaatagg gaatcctttc   82920
cccatttctt gtttttctca ggtttgtcaa agatcagaca gttgtaggta tgtggtgtta   82980
tttctgaggg ctctgttctg ttccattgat ctatatctct gttttggtac cagtaccatg   83040
ctgttttggt tactgtagcc ttgtagtaaa gtttgaagtc aggtagtgtg atgcctccag   83100
ctttgttctt ttggcttagg attgacttgg cgatgcgggc tcttttttgg ttccatatga   83160
actttaaagt agtttttcc aattctgtga agaaagtcat tggtagcttg atggggatgg   83220
cattgaatct gtaaattacc ttgggcagta tggccatttt cacaatattg attcttccta   83280
cccatgagca tggaatgttc ttccatttgt ttgtatcctc tttatttcc ttgagcagtg    83340 gtttgtagtt ctccttgaag aggtccttca catcccttgt aagttggatt cctaggtatt   83400
ttattctctt tgaagcaatt gtgaatggga gttcactcat gatttggctc tctgtttgtc   83460
tgttgttggt gtataagaat gcttgtgatt tttgtacatt gattttgtat cctgagactt   83520
tgctgaagtt gcttatcagc ttaaggagat tttgggctga gacaatgggg ttttctagat   83580
atacaatcat gtcatctgca aacagggaca atttgacttc ctcttttcct aattgaatac   83640 cctttattc cttctcctgc ctaattgccc tggccagaac ttccaacact atgttgaata   83700
ggagtggtga gagagggcat ccctgtcttg tgccagtttt caaagggaat gcttccagtt   83760
tttgcccatt cagtatgata ttggctgtgg gtttgtcata gatagctctt attattttga   83820
aatacgtccc atcaataccet aatttattga gagtttttag catgaagagt tgttgaattt   83880
```

```
tgtcaaaggc ttttttctgca tctattgaga taatcatgtg ttttttgtct ttggttctgt    83940
ttatatgctg gattacattt attgatttgc gtatattgaa ccagccttgc atcccaggga    84000
tgaagcccac ttgatcatgg tggataagct ttttgatgtg ctgctggatt cagtttgcca    84060
gtattttatt gaggattttt gcatcaatgt tcatcaagga tattggtcta aaattctctt    84120
tttttgttgt gtctctgccc ggctttggta tcagaatgat gctggcctca taaaatgagt    84180
tagggaggat tccctctttt tctattgatt ggaatagttt cagaaggaat ggtaccagtt    84240
cctccttgta cctctggtag aattcggctg taaatccatc tggtcctgga ctcttttttgg   84300
ttggtaagct attgattatt gccacaattt cagctcctgt tattggtcta ttaagagatt    84360
caacttcttc cacatgaagg tataggtgtt ttgcttgtat cgcaagcatc aaagtgccct    84420
cacatgaaca cgttagctta tcaatgctga taagagataa atttggcttt ttactaggaa    84480
tgttgcttac cttttgggat ctgagctgtt tagaacttct tcagagtgac taatttttaat   84540
ttttatcttt taggaggaat gcaggactgg aactatttac aaacaaattg ctttgaagtg    84600
actattgaac taggttgtgt gaaatatcca cttgagaaag agctgccaaa cttttgggaa    84660
cagaatcgaa gatcactaat ccagtttatg aaacaggtga ctattcagga gtgaagtatg    84720
aaatttctcc cgagggtgaa aagattttttg tgcgtacacg tggttttttgt gcagtgatttt  84780
tggaatacac tctttaaaat ttcaattcat tttagtatat ttaaccagtt tgtatattcc    84840
aaggtgttta atatatttat ctagaaaatt cgtgaatgga aatgagttta tttgtatatg    84900
tgaggaaaag ttgaagaaaa tgattgaaca aggtagtgat atttttgctct taagggttag   84960
tggtcacttt ttacccgtgt ttaaaaaaga ccagcataaa ttggatacac acctaatcat    85020
tggccaagtg atagaaagat gggctgtgga gtgaatgttt ttattctttt tcttgttgcc    85080
agtgatttac tgtgaaatga ttaatttcct tttgttttgga tatgtgtggt ggccagtagg    85140
taaagattat aagaaatata ctaatgttaa ttaggataat cagactaata ctttctgcca    85200
gtacatttct gcattttttct ttttcctgag tggtgtgaca taaagtctgt gagttttttt    85260
tactatattt aaagacattt tattctgaaa aatttttaaat atacagaaaa gttatgacta    85320
gccataatt attcctatac ctagatttaa catttttaaac attttgttat atttgcttta    85380
ttttaatgta aattttattt acacactcac atacacatac atattttttga ctgaactatt    85440
gtaatataaa ttgcaggtat ggtattttac ccctaaatat ttcagcatct atctcctaaa    85500
aataaggagc tactacatac tatctctaag tgctactgtc ctacccaaga aaattaacag    85560
taattcccta atattcccta atacttagtt tatatttaaa tgtccatatt tgtccccaaa    85620
atgtaatttt acagctgtat tttatgacca ggatctagtc aagtttcatg cattgcattg    85680
gattattata tctctttact attctttgaa ctataagagt ccttctgttt ttaaaaaatg    85740
ccatttcctt ttgaaaaggc caggtctgtt ttcttgtaga atgtcatata ttctgaaatc    85800
atcagaatgt gctaaagttt aaacagtgtt atttatattc ttcatgataa agagaaacaa    85860
agcctatgaa aaattagcct tcagaaatat tttaatgaac atttacattg aactttactc    85920
tgaactccta aattcctgtt tgttccattt attttgtgttg acaatctgtt attttgaata    85980
tgacctccca agataattag atgatgatgt ttattattga aatctggtgt ccttgtactt    86040
aatccaggtt catcagggcg tcagaggatt tgttctagat gccacagatg gcaggggtat    86100
attaaatgcc accattagtg ttgctgagat taatcaccca gtgactactt acaaaactgg    86160
agattactgg cgtctcttgg ttccaggaac ttataaaatc acagcatctg ctcgagggtg    86220
agtgactgaa tgctttgaaa tagagtgctc ggaggacaaa catggctcca ttctggagga    86280
```

```
ttattactag aacgttctag agagcctgtt aagcaacttt gaatggattg ctgcgaagtt    86340
tagggctggt tataccttttg actctccttt agtggcagat agagtacacg aaaaaaaaaa    86400
aaaggaaaga ttcctggggt aaatattcta gttattgctt agttgactca ttgtgacatg    86460
cttccaacct ggacattaaa caagacattt tagaatacac atcaaatcct gatcctcatg    86520
gccttaggtt ttttatttaa aaggagagtt aggctgaagt aattctacag tcagttccaa    86580
ttcatagtag aatttattgg aaatgtgttc aagatagttt ttcctttaaa ggagtaacag    86640
aagtgttagt tgatgaagca caaagaacat agaaaatgca tagaaagaac atttctcgtt    86700
cttttaattt gctaaataca ggtaagccca aagcaatgca gtctatttaa catgctagta    86760 acttttttt ttttttttt tttttttga cagagcctt ctctctatcg cccaggctgg    86820
agtgcatggc actatctcag ctgcctgcaa cttctgcctc ctgggttcaa gggatgcttg    86880
tgcctcagcc tcccaagtag ttgatattac tggtgtgtgc caccacaccc gactaatttt    86940
tgtattttta gtagagacag ggtttctctt gtagttttct tttttatctt ttgataagta    87000
tagatgttac cacaggatat tttcccttcc tcctgctagc taacttattt ctgaagagtt    87060
agtttgaata cccattgaag taagggtaaa atatgaaagc attttagtcg ttgcctttgt    87120 ttttaatgg ttttcagata tctagtggtc cgtaaatgaa tgggttagaa cctcacacta    87180
atgagtaatg aggtctttc tgtgattctt ccatttttgg cagagtgtta actaaagcag    87240
caggggatcc gagaaacagg gtgagaagga tgtgtttggc agagaatgtc ataacctagc    87300
acctctgcaa ctttcccacc cgtataccct gatagaagac aagtgaattt aagttccagg    87360
agacatggga gtatccacta caagcactaa atttctttg aagccatata tttaatctta    87420
aaaacctagg ccaggtgcgg tggctcaggt ctgtaatccc agcactttgg gaggcagagg    87480
caggtggatc acttgaggtc agaagtttga gaccagcctg gccaacatgg tgaaatcctg    87540
tctctactaa aaatacaaaa attatccagg catggtggtg ggcacctgca atcccagcta    87600
ctcaggaggc tgaggcagga gaatcacttg aacccaggag gcggaggttg cagtgaactg    87660
agatggtgcc actgcactcc agcctgggtg acagagcaag actccatctt aaaaaaaatc    87720
atgaaaaaaa atccattcat attttgtaat atacccatgt ctattcttta ttaatgtatt    87780
aaaaataata aattactcaa cgttaaaatt ttgtctcttt aggaaactgc accacattta    87840
tcccaaggat tcttacgttc tctgcacacc tgccttccca gggtttgggt actccagctg    87900
caggagtgtg gttctgatct gtctccttta tcataggtat aatccagtta ccaagaatgt    87960
gactgtcaag agtgaaggcg ctattcaggt caacttcaca cttgttcgat cctcaacaga    88020
ttcaaacaat gaatcaaaga aaggaaaagg ggctagcagc agcaccaatg atgccagtga    88080
tccaactact aaagagtttg aaactttaat taaagacctt tcagcggaga atggtttgga    88140
aagcctcatg ttacgctcct cctcaaatct ggctctggct ctttatcgat accattccta    88200
caaagactta tcagagtttc tgagaggact tgtaatgaac tatccacata ttacaaatct    88260
taccaagtaa gtgtcacttt ctattgtctt tttttttttt tcaagacagt aaaatcagca    88320
ttagccatgt tgaatagttg taattttatat agaaatattt gggaacagaa tgtacagaga    88380
gttggagttt acttatttg caacatgtat ttgcttggag atctttttt tttaattatg    88440 ctttaagttt tagggtacat gtgcacaacg tgcaggtttg ttacatatgt atacatgtgc    88500
catgttggtg tgctgcaccc attaactcgt catttacatt aggtatatct cctaatgcta    88560
tccctccccc ctacccctac cccacaacag accccagggt gtgatgttcc ccttcctgtg    88620
tccaagtgtt ctcattgttc agttcccacc tatgagtgag aacatgcagt gtttggtttt    88680
```

```
ttgtccttgc gatagtttgc tgagaatgat ggtttccagc ttcatccatg tccctacaaa    88740
ggacatgaac tcataatttt ttatggttgc atagtattcc atggtgtata tgtgccacat    88800
tttcttaatc cagtctatca ttgatggaca tttgggttgg ttccaagtct ttgctattgt    88860
gaatagtgcc acaataaaca tacgtgtgca tgtgtcttta tagcaccatg atttatagtc    88920
ctttgggtat atacccagta atgggatggc tgggtcaaat ggtatttcca gttctagatc    88980
cctgaggaat tgcaacactg acttccacaa tggttgaact agtttacagt cccaccaaca    89040
atgtaaaagt gttcctattt ctccacatcc tctccagcac ctgttgtttc ctgacttttt    89100
aatgattgct attctaactg atgtgagatg gtatctcact gtggttttga tttgcattct    89160
ctgatggcca gtgatgatga gcatttttt gtgtgtcttt tggctgcata aatgtcttct    89220
tttgagaagt gtctgttcat atccttcacc cactttttga tggggttgtt tgtattttc    89280 ttgtaaattt gtttaagttc tttgtagatt ctggatatta gccctttgtc agatgagtag    89340
attgcaaaaa ttttcttcca ttctgtaggt tgcctgttca ctctgatggt agtttctttt    89400
gctgtgcaga agctctttag tttaatgaga tcccatttgt caattttggc ttttgttgcc    89460
attgctattg gtgttttaga cataaagttc ttgcccatgc ctatgtcctg aatggtattg    89520
cctaggtttt cttctagggt ttttatggtt ttaggtctaa catgtaagtc tttaatccat    89580
cgtgaattaa tttttgtata aggtgtaagg aaggggtgct tggagatctt tttaatagtg    89640
aatcttggga actttaagga gaattacttg ttagattaga agtagatagc ctgtgattcc    89700
aggaaatgta aaattgctct tcctgataat tattttgact gattgtaaaa ccctttccat    89760
cactcagcta cagatctatt aatatgttct gactaaatat tgtttagttt gttttatttt    89820
gcttggggca agggaggaat ttagaactgt aagctcacct gttagggatt atgtgtaact    89880
tttttttttt aattagaaaa tgaagcctag ttgctgtcct aattctagtc tctattcaca    89940
gtctcttact tgaagcttta gggacatgtg tgatcgtggg tcccagggaa aacatacagt    90000
cctggcttat gtaaaactga tagctgagat agcctttacc ttcactttgt ggtggttgct    90060
ctgcctcact tgcactgctt cattttagat tttgttacag ttactccaaa attatttcta    90120
tgatttgttg attcctatgg tttgcctgtt gtagttaagg tctttacatt ttgccttgag    90180
catatagttc tctgctgcaa acctcatgaa cattatttag ccttttacct ttttactttg    90240
tctttcttca tgggtccttt taatttcatc agaaaactta gttcctcaaa ttctgattta    90300
taatattcat agatgcagag tgatacttaa cttcctttgg caataccaat tacttttctt    90360
ccttaactga ttcttggata tttctggcta tttcaggttt taatatcata caatcttagt    90420
gccatagagt tcatatactt tttattttta aaataaaacc aggctgggca cagtggctca    90480
cacctgtaat cccagcactt tgggaggccc aggtgggagg atcgcttgag gccaggagct    90540
ccagtttacg ttgaactatg atcacaccac tgtactccag cctaggtgac agtaagatcc    90600
tgtctctaaa acaaacaaaa attgggcatt attttgctgt ctgtttactt agttgattta    90660 attttttaa cctcctaatt caagacacac ttttttagtta aatatttct caaaatatgc    90720 cacacatgcc agtggtgggg cacaagagag ttttaggtgg tacaccaaca ggcactaagt    90780
accattgaat agcgtcatga gaaagcaata aggtttctgt taattttct caatttaata    90840 tgattatttt tttctgtcca attcttgtaa atctccottt atgctaaaga aagcagacct    90900
taagctcaaa gctcttgggc aagcagagta tttgaccatt gtttaatttt cattgaatta    90960
gtattttttt ccccactcaa attactttta ctgtgaaact ggtgttgcat ttatagtaaa    91020
atataacgtg acttatttac aaatattaat tttgattaaa aagggagggc cagggtggtg    91080
```

```
gcgcatgctg taatcccagc actttgggag gctgaggtgg gaggattgct tgaggccaga    91140
agcgcttgaa accagcctca gcaatatagc aagaccctgt ctctacaaaa ttttttttaa    91200
aaaattagct aggcatggtg gtgcaaacct gtagtactac tcccttagga gactgaggcc    91260
agaggatcac ttgagtcctg gaattcaagg ctgcagtgag ctatgatcaa gccattgcat    91320
tccagcttgg gtgacatagt gagaccctgt ctcttaaaaa tataatgaca ataatataaa    91380
taaataaata aataaataag ggaggttatc tatgttcata catacttaaa tatttctgta    91440 ataaaattt aatttgtgag ttagtacaaa atatattaac taaatagtag tgtagattaa    91500
agaagatagg gcaaatattg tgatgattgt atgagaatta ctgaatttgg aaggatggta    91560
aactaaatca taatctttcc taaatctttc ctaaatctga taatatcatc tatttgataa    91620
atgttctttg gtcaaggaaa actaattttc ttaaggtttt ctgatgcagt gattcactct    91680
ttaaagactt tttaaaactt tttgtgtttt gttttcattt ctattttaa agtccataag    91740 tcaacattaa catagtgctt gattacttgc tgattttttt gtttctggtt tttgaaagtt    91800
tgggacagag cactgaatat cgtcacattt ggtcccttga aatctccaat aagcccaatg    91860
tatctgagcc tgaagaacca aagattcgtt ttgttgctgg tatccatgga aatgcgccag    91920
ttggaactga actgcttttg gctctggcag aatttctctg cctgaactac aaaaagaacc    91980
cagctgttac ccaagtaaga gaatagccga ggttgacatg ctttaaaagg aaaaagctca    92040
acattaatat cagggcacca tttttaaaat ttttaatttc ttgctagatt ttacagagtc    92100
acttgtagta cattatgaac tttactcttt aaaaatgaac catctttgta gtatataccc    92160
tttgttaata gtgtctttct attatatttc cttgtatgtc ttaagaggca tgcaggaaag    92220
aatactaaaa atttcattc aatttcctac tccgtcattt aatagccaca ctacccttcc    92280
agtctttatt catagttctt tacttttttt ttttttttt gagacagagt cctgctctat    92340
cacccaggct tgagtgcaat ggcatgatct cggctcactg caacctccac ctcctggatt    92400
caagcaatta tcccgcctca gcttcctgag tagctgggac tacagatgcc caccaccatg    92460
cccggctaat ttttttatat tttggtaga cgggtttt tgccatgttg gccacgctgg    92520
tctcgaactc ctgacctcag gtaatccacc tcctttggcc tcccaaaaat gctgtgatta    92580
caggcgtgag ccatggcgcc tggccagttt tttacattct gacttgaggg acttccattc    92640
tgaattactt ataactagga cactatattg aaaaatctag tgaaagccta gttttcagt    92700 atagtttttct ttttcatgta atacataaaa aattattgga catcttggct gctaagagat    92760
tttagaaaaa gcaatatggt gttatctact ttagcaatct gtgactacag aaaagaactt    92820
tgactggggt gtgatggctc atgcctgtaa tcacaacact tcaggggct gaagagagag    92880 gaccacttga ggccaggcgt ttgagaccag ccagagcagc agagtgatac cttgtctcta    92940
caaaaattta aaaaattagc tgggccttgt ggtgcacacc tgtaatccta gctacttggg    93000
acgctaaagt gggaggatca cttgagccta gtaggtcaag actgcagtga gctgtgattg    93060
caccactgca ttccagcctg ggtaacaggc tggaatctca aaacaaaca aacaaaaca    93120 aaactttgac ccagaggctt gggcacgtat gattaagcat cctagttgta cgttgcctca    93180
gagaagggaa ggaaagagtg aaacactcac taattggcac tgtccatagt ggacttagga    93240
aagggaaaaa gaactgatat ttattgaata catattttgt gctgggtaat ataccaggta    93300
ttttatatac gtcattatat cctcaaccct gtgataatga ttatctccat tttataaatg    93360
tagaaactga ggcagtccca cagctagaaa ctggtaaaac tagaatttaa acccacgtat    93420
gtctactttg aagcccagtg cagttctgcc tccccaaaac aaattgggaa agaattgatg    93480
```

| | |
|---|---|
| tcatgattag gatcagaagg gacctgtgta attaggtgac atgaacttaa atcagactga | 93540 |
| ccaaaaatta tgttatcttc ctttgtggga caggtgctct gtgttgcgaa cttactcaac | 93600 |
| tctgccatta gagcacaaaa cagtcatatg taaatgaata gtcatgctta tgtgtcagta | 93660 |
| aaactttata tacaatagca ggcaccaact ggatttggcc tgctgttagt ggtttctcac | 93720 |
| ccctgttcta agtcactgga aggtctctgg gaacattagc tgtacagtag ttttttgctt | 93780 |
| attttttaata tatttgaagc aaaaggaaat ttaattttt attttttcat tcatcttagt | 93840 |
| tctgtctttt aaattaacta tgtgtagaat aaacagactt tctgtttgag gcatgagagg | 93900 |
| gtacccattg attctacatg cagctagtaa ctcgttaatt tctgtttgtg cttcagttgg | 93960 |
| ttgacaggac taggattgtg attgtcccct ctctaaatcc agatgggcga gagagagctc | 94020 |
| aagagaaaga ctgtacttca aaaataggac aaacaaatgc tcgtggcaaa gatttggata | 94080 |
| cagacttcac aagtaagact aattttttagg ctactaaagt acttaggaga taattttcttt | 94140 |
| tctgctagaa gattgattga tcctattttg tcagtaaata atggagtact ttcttgtctg | 94200 |
| ggttatgaat gtgaggtata aatgaattca gacatctgga aaagttttttg aattttttctc | 94260 |
| cattattatt tgcaaaaata atttaagttt ttcatagaaa ttcaatccat tatattggga | 94320 |
| tgtttgtttc ttcactagtt gtgtagagat gtgtattctc tctcccctcc tatgtatgtg | 94380 |
| tgtatgtgta tacacgcaca acacacacgt atgtatattg atttggagag ccctatttct | 94440 |
| tatttactta aatgggacct ttttcattga atatgtatca ttgacatggt tcaatttcag | 94500 |
| tacttataga tctctaacat tcttttttctt ttttttttttt ttgagacaga gtctcactct | 94560 |
| gttgcccagg ctggagtgca atggtacaat cttggctcgc ctccgcctct tgggttaagc | 94620 |
| aattatcctg cctcagcctc ctgaatagct gggattacag ggacccgcca ccatgcctgg | 94680 |
| ccaattttttg tatttttagt agagatgggg ttttatcatg ttgaccaggc tggtcttgaa | 94740 |
| ctcccgacct cgggtgatcc gcctgcccag cctcccaaag tgctgggatt ataggcatta | 94800 |
| gccactgtgc caggcccaac attatttttct aatggcatct agtatgccat gaatctatga | 94860 |
| cagtactctt aatttattca accatttttct actgatagat atttacttta tttctgatttt | 94920 |
| tttgcttttg taaacagtgc tgcagagaac acccggcttt ctgaaactct aattttcttc | 94980 |
| caaagataat gtatttgtcc attttcacac tgctgataaa ggcataccca agactggaaa | 95040 |
| gaaaaggagt tttaatttga cttacagctc tacatggctg gggaggtttc acaatcatgc | 95100 |
| tgcaggatga aagccacttc ttacatggtg gcagcaagag agtgtgagaa ggaagcaaaa | 95160 |
| gcagatctga taaacccatc agatctcata agacttattc actatcacaa gaataatacg | 95220 |
| ggaaagaccc gcccccatga ttcagttacc tcccaccggc tccctcccac aacaagtggg | 95280 |
| aattctggga gataaaattc gagttgagat ttgagtgggg acacagccaa accatatcat | 95340 |
| tctgccactg gcccctccca aatctcatgt cctcacatttt caaaaccaat catgccttcc | 95400 |
| caacagtccc ccaaagtctt atttcagcat taactcaaaa gtccacagtc caacatctca | 95460 |
| tctaagacag gtcccttctg cctctgaggc tgtaaaatca aaagcaagtt agttacttcc | 95520 |
| tagataaaat aggggtacag gcattgagta aatacagcca ttccaaatgg gagaaattgg | 95580 |
| ccaaaatgga ggggctacag gccccatgca agttcagaat ccagcagggc agtcaaatct | 95640 |
| taaaagttca aaaattttct cctttgactc catgtcttgc atctaggtca tgctgatgca | 95700 |
| agaagtgggt tcccatggtc ttgggcagct ccaccctgt ggctttacag ggtacaggct | 95760 |
| gtctcccagc tgcttttcacc agctggcatt gagtgtctgt ggcttttcca ggggcatggt | 95820 |
| gcaagctgtc gtggatctac cattctggag tctggaggat ggtggccctc ttctcacagc | 95880 |

| | |
|---|---|
| tccactaggc agtacctcag tagggactct gtgtgggggc tctgatccca catttccctt | 95940 |
| ctgcactgcc ctagcagagg ttctccatga ggggcctgcc cctgcagcaa acttttgcct | 96000 |
| ggacatccaa gcttttccat acatcttctg aaatctaggt ggaggttccc aaacatcaat | 96060 |
| tcttgacttt tttgcacccg cgggctcaat gccacatgga agctgccagg tctcggggct | 96120 |
| tccacccatt gaagcaacag cccgagctgt accttggccc cttttagtca cagccggcac | 96180 |
| agctgggaca cagggcacca agtccctaga ttgcccccag cacggggacc ctgggcccag | 96240 |
| cccacaaaac cagttttttcc tcctgggcct ccaggccttt gatgggaggg gctgccgaga | 96300 |
| aggtctctga catggcctgg agacattttc cccatggtct tggggattaa cattaggctc | 96360 |
| ctggctactt atgcaaattt ctgcagctgg gttgaatttc tccccagaaa atgggttttt | 96420 |
| cttttctatt gcatagtcag gctgcaaatt ttccaaactt ttatgctttg cttcccttat | 96480 |
| aaaactgaat gcctttaaca gcacccatgt cacctcttga atgctttgct gcttagaaat | 96540 |
| ttcttccgcc agatacccta aatcatctct ctcagattca aagttccaaa aatctctagg | 96600 |
| gcagggcaa aatgctgcca gtctctttgc taaaacataa caagaatcat ctttgctcca | 96660 |
| gttcccaaca agttcattat ctccgtctga gaccacctca gcctggacct tattggtcat | 96720 |
| atcactatca gcattttttgt caaagccatt caacaagtct ctaggaagtt ctatgctttc | 96780 |
| ccacattttc ccatcttctt ctgagcccta caaactattc caacctctgc ctgttaccca | 96840 |
| gctccaaagc tgcttccaca ttttttggta tcttttcagc aacacctggc tctattggta | 96900 |
| ccaatttact gtattagtct gttttcaaac tgctaataaa gacatactcg agactgggaa | 96960 |
| gaaaaggaga tttaattgga cttacagtcc cacatggctg gggaggtttc acaatcatag | 97020 |
| cggaggatga aaggcacttc ttacatggca gtggcaagag agaatgagaa ggaagtgaaa | 97080 |
| gtggaatccc ctggtaaacc catcagatct tgtgagactt attcactatc acaagaatag | 97140 |
| catggcaaag acccgcccc atgattcagt cacctcccac tgggtacctc ccacaacacg | 97200 |
| tgggaattct gggagataca attcaagttg agatttgggt gggggtacag ccaaaccata | 97260 |
| tcagataggt tatttatata ttccctaaat tattttgtaa agctggatat gcttattctt | 97320 |
| tttgttttt taataagatt tttctttaac ttgcttagag tcattagtat atacacatcc | 97380 |
| tgaagtacat aataaaactc agactaacct accttctgta atgtatcttt cttgcttgag | 97440 |
| atagtggctt atggagaaat aaaatattta tctacaaatt tttaagttag cattttgatt | 97500 |
| gtattcaagt agagaatatt ttcttagata ctcatactaa gatttaaaat ttgatatttt | 97560 |
| atatttgact tttctctttt ttagataatg cctcccaacc tgagaccaaa gccatcattg | 97620 |
| aaaatttgat tcaaaaacag gactttagtc tttctgttgc cttagatggt ggttccatgc | 97680 |
| tggtcacata tccttatgac aagccagtac agacaggtat gtagaatgtc attttatata | 97740 |
| tatactgttt aagcttaggt agcaaatccc aattaagtaa tgtcccttcc acatttttat | 97800 |
| aaatagtgag catttgagca cactctatga gcaaattacc aaccaaagaa gattgtacat | 97860 |
| acatcagcag ttcagttact tggagagctc agatctaatg gtagcccagc tttattgagt | 97920 |
| ctagctatct tgttccatct gttccattta gtccacaagc atttactgag caattattat | 97980 |
| gtctgtaaat attgagaata taaaagtgag tatgacacgg tttctgcctc atgaaactcc | 98040 |
| tatgtaacca aatactaaca gtacagattt gtccttccct gttttaaact ttgactaagt | 98100 |
| ggttgcacct tatggtgagt taaatagttg gttgtttaat ctctgtgggg tcgcagtata | 98160 |
| tggagatagt ttgggtggtt ttcagtgcat cttacaaaga atattgttat taggctacag | 98220 |
| ttgtcccaaa atgcagtaag acataccaaa acaagtttgt attttagtgt gatagtctgt | 98280 |

```
tgtgaaaact caccattaga accttttcat gtaaagagga tgtttgtctt ctattatctt    98340
gggctaaata aaaccttttta ggggttaatta tagtaacagt atacttaagt ggagtgcaaa    98400
atttattagg agaaaaagat gacttgtatc catgaaggtt aacttggggg aaaaaaatca    98460
tttggatttc tccactgact tctaaatttt tctttctata gtggaaaata aagagactct    98520
gaagcatttg gcatctcttt atgcaaataa tcatccatcc atgcacatgg gtcagcccag    98580
ttgcccaaat aaatcaggta gatgttttcc ataccttttg ttattgctgt tgttgttgtt    98640
gcttttgtgg ggaaggagt ttcaccttaa ggtcttcctg attccacatc tcttaatgct    98700
tttatagatg agaatattcc aggaggagta atgcgtggag cagaatggca tagtcacctg    98760
ggcagcatga aggtatgctt tctagaacat ggttagaatg gagttatggc caggcacaat    98820
gccgtatgtg taaacccagt gctttgggag gccaaggcag gtggattttc tgagtttggg    98880
agttcaagac cagcctggcc aacatggtga accccatttc ctactaaaaa tataaaaatt    98940
agctgggtgt ggtggcagac gcccgtaatc ccagctactt gggaggctga gtcaggagaa    99000
tcgcttgaac ctgggaggcg gaggttgcag tgagtcgagc cgagatcgca ctactgcact    99060
ccagcctggg caacagagca agattccatc tcaaaaaaaa aaaaaaaaaa aaaagaatgc    99120
gagtttatga atatcagcca ttgagtacaa gaataggtga ctttctggt attgtaaagt    99180 gaatggcatc tgcctcatgg ctttcttgac atgtttagcc cttacattaa cccgacagta    99240 ctttttttggc cattttaacc attttaatt gtacagttta gtgacattaa ttaaatgttg    99300
tgccccaaaa accatatcta tttccaaaac ttcatttgcc ccagacagaa actctgtacc    99360
cactaagcaa taactcccta ttccctctc ccacggctcc tggaacccct gtctactttc    99420
tgcctctatg aatttgccta ttctaggtat ttcatgtaag tagaatcata caatatttac    99480
cctttcactt agcaaaatgt ttttaggatt catccatttt agagcatgta tcattacttc    99540
attcattttt atggctgaat aatattctat ttatgtttat accacatttt atttgttaat    99600
tcatgtgtca atgggcactt ggatttctac ttttttggctg ttgcaaatga tgttgccatg    99660
aagattggta ttgcaggtat ctgtttgaac cctgtgctgc catgaacatt ggtattacaa    99720
gtatctgtca cttctttggg gtagataacct aggagtggaa ttgcctggtt atattgtaag    99780
tctatgtttc accttttgag gaaccaccaa actgttttcc acagcagctg caccatttta    99840
cattccttac cagcaatgtt tgaggtttcc aattttccca tatcctctcc tcaccaacac    99900
ttatttgctg gtttttttt tttaaacag agtctcactt tgttgctcag gctggagtgc    99960
agtggctatg gctccttcgc agcttattgc agcctgaacc tcccaggccc aagcaatccc   100020
cccacctcag cctcctgagt agccaagacc acccgcatgc accaccatgc tgaaccaatt   100080 atttttaattt ctttgtagag acagggtctc cctttgttgc ctaggctgga gttctttata   100140
tattaatata aaaggctgag cgtggtggtg gctcatgcct ataatcccag cactttggga   100200
ggccgaggcg ggaggatcac ctgaggtcag gagtttgaga ccagcctggc caacatggtg   100260
aaacccatct ctactaaaaa tacaaaaaaa ttagctgggc gtggtggcag gtgcctgtaa   100320
tcccagctac ttgggaggct gaggcaggag aatcgcttga acttgggaag cagaggtttc   100380
agtgagccga gattacacca ttgcactcca gcctgggcaa caaacacgaa actctgtctc   100440
aaaaaaacga ataaacaaac aaaacccatt ctggatgctg tgtattctag ataggaaatt   100500
cttatcagat acatgatttg caagtatttt ctcctattct ttaggttacc ttttaaattt   100560
cttgattatg tccttttgata catgagtttt taattgtaac gaaatccagt gtacctgttt   100620
ttgttgttgt tgcttttgca gttgttatcc tatctaagga tctgttgcta aatccaaggt   100680
```

```
catgaagatg ccccgcccca ccccatgttt tcttttcttt ttttggagg gcaaatgtgg   100740
gatgagtggg aggggcgggg tacatggccc cctgcccac ctccctgctc cctgccgcct   100800
atccttgtgt tttctttgaa gagttttatg ggcttggcac ggtggctcag gcctgtaatc   100860
tgagcacttt gggaggccaa ggtgggtgga tcatttgatg tcaggagttc aagaccagcc   100920
tggccaacat gttgaaaccc catatactaa aaatacaaac attagccagg ctgtagtgct   100980
gcgcacctgt aatcccagct acccgggagg ctgtggcagg agaattgctt gagcctggga   101040
tgggaagatt gcgaagagcc gagatcttgc cacttcactt gagtctgggc aacagagtga   101100
gaccctgtct caaaaaaaaa aaaagaaaa aaaagagttt tatggatcaa gctgccatat   101160
ttcagtcatt gatgcagttt attttttatg gtatgaagta ggagttcaac ttcgtttgtt   101220
tgtatgtaga aattcagttg tgtcagcact atttgttgaa agactattct ttccccactg   101280
aatggttttg gtatccttcc caaaaatgag tttaccatag atgtgtggat ttatttctgg   101340
actctcaatt ctattccatt ggtctatatg tttgccttta tgccagtatc acttttttt   101400
tttttttttt ggttgttgtt ttccttttt ttaatttatt tttatttat ttttatttat   101460
tatttattat ttattattta tttttttatt atactttaag ttttagggta catgtgcaca   101520
acgtgcaggt tagttacata tgtatacatg tgccatgttg gtgtgctgca ctcatcaact   101580
catcatttaa cattaggtat atctcctaat gctatccctc ccccgaccc acaacaggcc   101640
ctggtgtgtg atgttccct tcctgtgtcc atgtgttctc attgttcagt ccccacctat   101700
gagtgagaac atgcggtgtt tggtttttg tccttgcgat agtttgctga gaatgatggt   101760
ttccagcttc atcagtatca ctgttttgat taatgtaggt tgttgtagt aagttgtaaa   101820
attggaacgt gtgagtcttt cagctttatt gttcttaaag attgttttgg ctattcaggg   101880
cccttgtca ttccatttga atttgagcat tggcttttct ttttctgaga aaggggtgt   101940
tggaattttg ttagatgttg tgttaaaacc gtatatcact ttgtgtagta ttgacatctc   102000
tacaatattg tcctcctatc cattattttag gtcttcttta atttctgaca gcattttaat   102060
tcattgtcca tccacttcaa attaggcagg agttgttagc agatgggtgg ttggctgatc   102120
attttattca catgtgcaac cagaaaattg acttattcc catttctgcc tgtcttccct   102180
cctttattta ctaagaactt actactggga ggcattttgc tatattagtg ataaataaaa   102240
tatactgcct ggcctattgt acgaattaac tgtgttacat aattaattga tttgatctgg   102300
aagagagcaa ctctcagcag gccgtgagaa attaaagaca caaaaaatta tatctagtca   102360
gagatacagc ctttttctctt tagaggagat ggcatttggg ctgcagagat agtgaagcag   102420
aacattccag aaagaggaag cagtacatag cagaagtcta atttagttag aatatggggt   102480
gtaatgcaga gccacagaag tttaagaatg gaaagagtgc ttgttgcttt gaatgctttg   102540
ttttaataag aatgggaaac tgaggttttg agcagggta acaatattga catgatctga   102600
gctatgctat gggaaaacta atctctaaat aatcagttaa gatagtttgg aggaaggaga   102660
gactggtaca gggagaccgg tttggaatta tctagacaaa aagtaatgag ggcctaggtt   102720
atgctagtgg caacgagagt agagtcaaag gatgacattt tagatattct atagaggtag   102780
aattgacaag attcagcaaa ttatggatga tagtgagata gagaagtcaa agacaagagg   102840
tttcattgct atgtaagaaa atgagttaat accattaact gagttaggaa aaagaagaga   102900
ttttgggaaa aggtggtaag ttgggttttt gaacctgtct gcacaggcag ttcctgtacc   102960
ttgataatat caatgccgta ttgcaggag tggatattgt caccagcagg ggtccaggtt   103020
gagggtatga gagagctgat gatcattatc tccatagctt caagtacaac tgtgacattt   103080
```

```
ctgggttttg agggaagctg accctcttct gcatgtactc attcattcat ttcttcagca   103140
aacccgaata aaccccatct acctggcact accaggcact gtgggaagca ctgaagatag   103200
gaaaatgaat tcgacatagc ccctgtcctc aagggctctc atagagtttg tgattgatta   103260
taatacagag aggtttattt atatttgtca taaaatgctt tacagcttct ttgtttacgt   103320
cagctacgtt ttcttttcat ttactccatt tgttgtatta caaagcctta ttctttcttt   103380
tacttattaa ttttcccaca tttgattttg aactttatat tctaggatta tagtgtcacc   103440
tatggccatt gtccggaaat cacagtatac acaagctgct gttactttcc tagtgctgca   103500
cgactccctt ccttgtgggc agacaataag agatctcttc ttagtatgtt agtggaggtg   103560
agtcttttcc ttttaactag aggcaaactc ccaggaatat gttcagtgaa aacctttatc   103620
aaaacattgt cttttaccaa aaatgtatat tatttatttt aaatttatat agaaagaaga   103680
gttttggtca ttttatgttt cctaaataga tgccatttat tcacatctct ggaatctgct   103740
ataatttagg taatttgacc ttgcaagatg ctgcaagttc tttaatttga atatcacaga   103800
gttactggag tcagtatacc atggtgggaa ggaaatcact caaggcattg gaagattggg   103860
ttctaatgct tcaggctatg acaatatcag agttctcttt tatttccagc tctgtgagcc   103920
tgaatattga atgaatagca aacaaggtca gagtcagtgg ggagggaaga gaagaagcag   103980
gccatacaga gtttgatact tgtttgtgtg tggttttttgt tttgtttgtt tgtttggttg   104040
gttttggtca tgcctcaagc tagtgcctct accatgtctg gcattatgac aacataaatt   104100
tatattttaa acattttttc aggttcacaa gggagttcat ggatttgtta aagataagac   104160
tggaaagcca atctctaaag cagtcattgt acttaatgaa ggaataaagg tacaaacaaa   104220
agagggaggt tatttccatg tactcttagc gccaggtgtc cataacatta ttgccatcgc   104280
tgatgggtac cagcaacaac attcacaggt aagaaactca aattgagtag catcatgtaa   104340
atttttattc ttaataatac ttctgtttta ttttgaaact cttgttagaa atcttgaagg   104400
gaataaagaa attaaaagtg tgactgcctc ttgattatga tatcttgtta tccttgtacc   104460
ccttgctaac aaaagggaaa attttctagc attttgtata cttagatgg caatgcatca    104520
tctccttagt ttgctatatg gggcctaata atatagcagg gatacagtac accttaagca   104580
gaatttgtca tgattcttac actttctcct tctaggtctt tgtgcatcat gatgcagcta   104640
gttctgtggt gatagtcttt gacacagata accggatatt tggtttgcca agggagcttg   104700
tggtaactgt atcaggtaaa gacattttga ttttagtag taaaagttaa aaacaatctt   104760
gacatttcaa tatgagagtg ggtcacctct ctcatattga tcctgaaact aatcacttgt   104820
cttctaatgt ctccttatct aaatgtgatt ttcctggacc tctgttctcg catatgttct   104880
cctggcttgc ctttctctgc cgagaccagc tccatcaagg agaccctaac ccagcggtgc   104940
tagagaaatt aaagacacac acagaaatat agaggtgtca agtgggaaat cagggtctc    105000
atagccttca gcgctgagaa cctccaacag agatttaccc aggtgtttat taacagcaag   105060
ccagtcatta gcattgtttc tatagatatt atattagctg aaagtatcct ttatgggaaa   105120
cgaagggatg ggccaaaata aagggatggg ttgggctagt tatctgcagc aggagcatgt   105180
ccttaaggca cagatcactc atgctattgt ttgtggttta agaacgcctt taagcagttt   105240
tccgccctgg gcgggccagg tgttccttgc cttcattccg gtaaacccac aaccttctag   105300
tgtggatgtc atggccatca tgaacatgtc acagtgctgc agagattttg tttatggcca   105360
gttttggggc cagtttatgg ccatattttg gggggcctgt tcccaacact tctctttctt   105420
caggtctata ctcaaacgtc acctccacgg agaggctttc cctgatcacc ctagctaccc   105480
```

```
ctgtcactat ctctatcctg cttttttca ttatagcact ttcataacat tatatatttg  105540
ttcatgtatt tgtctatatt caatctctcc cactaaaaca taagttctga gagagggagg  105600
aatctacctg tatcctccaa gcctagaacg atggttagca cgcagtgggt cttaatgaag  105660
agttgttgaa tgaatgaatg atttgcttta tattaaagtc ataagttcct aggactttga  105720
cttatattag ttccgctttt tcaagatcca ggaaagagga aatgtttgtt tacgctggaa  105780
ctaattcatg tcattgcttg gattactgaa aggttaggaa ggaaaaaaat gtggtaaaat  105840
gaatactctg ctatacttta tctatttgat acaaacagcc ttagtttatt tctaagtgca  105900
gcttggatga ggcagaataa ccaagtttta tcacagggtt cctgtgggag agacccttag  105960
ttgagagaaa gtagtatatt ggaaacatgg cccaatcata gatcctgtgt ggtgtgttta  106020
aagggttctt agcttgtctc agataaagtg taaataactt agtggttaaa aacacaggag  106080
gtagaattca gccatggttt aaatctggct ctgtcaccca ttagctattg tgaacttagt  106140
ttttattact tttagtttct aacactttta ttttgataac cttgtacaaa tttaaaataa  106200
acaaggagat ttggatgaaa tgaaagttta ctggaaagga aaagtataat agaagtcata  106260
aaaagcaggt tgcagaacag tagacacagt ataatttcat tatggtaaaa gaaaaaaaat  106320
acatgtacgt gcatatgcat aaagaaagat ctggagccag gcatggtggc tcacgcctgt  106380
aataccagca ctttgggagg ccgaggcagg tggatcactt gaagtcagga gttctagact  106440
agcctgggca acatggcaaa accctatctc tagcaaaaat aaaaaaaaat tagccaggtg  106500
tggtggcatg cacctgtggt actacttggg aggctgaggt gggaggatta cacacacaca  106560
caaaagatct tataactaaa aatgatctct gggtaatgga aatgtaaata taggaggttt  106620
tttggttttg gcttttgtta gtttgcttat ctgtatttttt aaactttgta tattgtacat  106680
atactgcttc tataataata aaggttgttc ttaagtgcat gaaatagaaa taaaataaat  106740
gaggggtata ttattaaaag ttccattgta agcggctgct tattaatatc cttaaagtat  106800
aatatcaccc acatgatggt ttttgtttgt caggtgctac tatgtcggca ttgatcctaa  106860
cagcttgcat tatttggtgc atctgctcaa tcaagtctaa tagacacaag gatggctttc  106920
atcggctcag gcagcatcat gatgagtatg aagatgaaat tcgcatgatg tctaccggct  106980
ccaagaagtc cctcctaagc catgagttcc aggatgaaac agacactgaa gaggaaacat  107040
tatattctag caaacattga aaaacacatt ttgcatatct cccagcataa gtaccaagca  107100
aaattacagt tcctcttggg agaacactgc attaagaaga gagactctct tgcttcttca  107160
aagagctttg ggaaattaaa ttgctaaatt tgtattctct gtgaatttca ctggcagttt  107220
tgaacttccc ttccttaaag tactctaaac ctttaaaaaa aaatctgatt tatgcagcag  107280
agatgggaca gccacttttt cttttttaatt taagatgagc tatttggagc ttatgtaata  107340
atggcataaa gccaactaga ggatgttgta ttttgcacat cagatgttta ctagtggctt  107400 tagtatttt ctttgtttta aatggccaaa agaatccaga acattaagg cagggacagc  107460 agtcagaatc gacataaagc tttaaaaact caaggttttt tcaacctact gaggagtact  107520
tttctctagt tgttaaatag ctggagtttt tcttattcag gttaatgga ggttgaattg  107580 atttttaaac acatataaca gtaggaaatg aataaatggg cttctgcatt tggctttcta  107640
cctgttccaa ggctagatcg gaactggtag actacgctgt aagcaggatt tcactacctc  107700
tcttaaggtt tagcaaactt ctaaatagcc cattttaagg gagaacttac taactttatt  107760
gtgaaaggtc taaatgccca cttgaatgaa gctgagagag gatctagca aaagctaaaa  107820 ctcatgttgt ctatctttga acttggtaaa aacccacagg tgctgctgct tatatctgtg  107880
```

```
aagcactagc ttattctagg aatgcctgat tctttaatat tgcctaaatc ggaaccttt     107940
tctatgttgc acacatggtt ttcagatgac ccagccatct acaagatctg aattctactg   108000
aaaatatcta gaaatgtgga agagacctac ttgcacattc ttaacctgta tttgaacaca   108060
aaatatctat acttcatgct ccagcccaag cctataccct gtaatagcat actattattg   108120
aaatcgcttg accggtcttg ttcacatagg cctctgggag tgatttggtt ctttgcccta   108180
atgtttcatt tgacggtctc ttttttgatca accaattttt ctaaaagttc agtcgaaagc   108240
ttttaagtat agcttcctcc cttgaaaaaa aatgtaaact atgactgctg agtgataaaa    108300
cactgtggtg tgaaagtgtc atcttcactg ccaatcaggc aaagaccgga agatttgca    108360
ttttattatg tctgtcttat catgcaatgg aaatgatgct ttttgtaagt atgcatctta   108420
ccaatgatgt aacggtttaa tacctttgaa tgttttaata accaagttgc tgctgaactt   108480
atactaaatc aggggaccaa aaaacttgct cttatcttct caaattgtat tctatatcca   108540
ttaatgtatc agttatccca aagccttcag gtggagggggt ttaccacctt cctaggtcgt  108600
tcaaccaggt tttgtgagga atgcattcaa agtggcttta taaaagaaga ttttctttag  108660
caagaataat gaggtcatgt catttgttaa taagtatctg tgataaatcc gtggttcaag   108720
gttaagccat tctggtattc tggtattagc aactgtaaat tctgccacct catacatgga   108780
acagagcttg tgggatgcta atagttagtg aagtatacat gatttaattt ctaataatct   108840
ttatgttttc tttaaggatg gtggtgtatt gctcttttc agctttattt ttaagagtac   108900
agtcaggaaa ccaacaaggg gcctaagagt ggctgcccct gcttgggaca ttacagcaag   108960
tgaaacaaag ttaatgtgac aagctttgct ttgttatcat tggtcttcac tagaggatac   109020
cttttacatg tacttctctc ttggatcaaa tatgtcttta actgtacatc tcagtggctg   109080
gaggccatgc cttttaagca tgtgtaaaat ttttaaagaa atgaacatac acatagttat  109140
tttagtaata tttcctgaaa gaaaaaccaa attctgctat aagtcttgat cttcaatgaa   109200
cttttaaata atgcatttag ctggaaaaca agactttccc agcttgtatt acctagaagc   109260
gtgaatgtat aggatacctg actactaaga ctatattctc agccctgccc tgtctttat    109320
ttgcgggtct aatctaatat tagaatatat taaccgctta aggcattgaa gccatatggg   109380
atggggaatg catttcttca gtgtttctcc gagagacttt ccatttcctt ggagttatgg   109440
cggcaagtaa gtatcatagt attaagaaat ttgcctaaat ctgagttgtg cctttctta   109500
ctcacaaggc atgggctttg tcctggtgat cagtttgtaa gccttcttcc ttcccagctc   109560
cttaataaaa gcaaagtgat tgagtaggta atgttcaaag tgtctgcctg tgtacatgta   109620
cttgtattga ttatgtagtt cagtaagatg tgcccaagtc atttcagaaa gaaagaccct   109680
tcagttttga tgcattttgc tgaacacttg ggtagtgagt gggatcctat ccagttgagg   109740
aatgcttgca atgctcattg aagggatttg ctttgggact ttgtcatctt ccagaaagga   109800
aacatattgt atatttggcc cagtgtgatt gattgcttta tcttttggtaa cttttacttg   109860
aatgggattt gctgaattaa tgactattga atttaaaact aattatgagt tgacaaataa   109920
ataaaaggta gtgtttatgt ctgagcttat tgtgtttgag ctaacaccag ttactcagt    109980
aaccatgacc tgctcctcca tttccattta ttctcaacat taaatagttt tatcttgttg   110040
ttgccagaaa tgcacttgtg ccaggtattg tccctgctgt atgaaaagct tcttggcaat   110100
gaattctgta atagtgccct acattatggt tttctggtgg aattgtttta acagtgacaa   110160
cccaggattt ccaatatatt tttgttttat tgttattacc aaaaattcca ctatgattga   110220
tgttcagtga ttttctatag caactttttt ggtaactctt tgggtttctg atttgtttta   110280
```

```
gctaaaattt tggggatatg atttgggtct ttgattaatg tcagctgaac ttggatttct    110340
agttcatgaa gaaatctctc ccaataccca tttatcctat ttttagcaat aattcgttaa    110400
tgattccact tgattttcag aatattgtcc tggttgattt tgatttgaca gcatacatta    110460
tgaaatttga aagtaggtta ccattttgag gcagttggat ataaattatg taaatatgta    110520
tgattatgat ttttataaat ggcataacat gagtgtacta actaccttct atgctggcca    110580
tgctacagat tttctggagg tatgacaata gtattttttt atgctcagat taaaaatcag    110640
cttttcacct ctccagtttt tccaagtgat actcccagtt ctagagcaat ctacagctgt    110700
ttatgtgagg tgcccaacac ccattcatct caagtgcttc agtctttggt ttatttcatg    110760
cactgtgcct tcaaaatgaa attttttaaaa gggactttaa atgaagttga atagtagttt    110820
ttaaaagtca atttgtaatt tatgtgaaat ctaactgtaa tgaggtcctt tctgtttttt    110880
atatgtaaac agatctacta atcctgtata aaagttattt tacgatgttt gtctttcttt    110940
gtgttttgtc tcataatctt ttttcagatg caatatgccg gaaaaagtta taggtccagt    111000
ttgaaaatta tttagttttt ctgcctatgc tagtggaaaa atagtaccag gatcagaata    111060
cagggtatca cctatggaat gtttctgtat ttatgaattg actcaaaaga aagctttgtt    111120
tctgaaatcg cattatgtag tagccacagt tttctgtttg tagctcagct agattgttat    111180
atatgttcaa tcatttcaca ataacaacac aaaactggtc attgaaaggt ttttatgtac    111240
gcattttaaa cttgttcgtt aaaaatttgg tccttttttcc aggtgaggcc cagttagaat    111300
aatgtgtccc ggcactttta ggcacagcaa ggatgaattc aatatcccct tttcacttag    111360
caacaatgtg ttacttctac cctaatagga attgggaaag caaagttgta tgagaaacag    111420
actctgctga taaagtactc atagtccaga ccagagaaat ataaatggaa ataggttata    111480
tttcaatagt gattggttca tctaaaagtc tctgctgtaa aggaaataaa gcatagaggt    111540
ttgagcatgg actttggagt tggaccaatc tgtgactgat tcttcgttct gctacttgct    111600
tccaatgtga ccttgtacaa gtttcttgac attctctgag cctcagtttc tctactggtt    111660
gaataatcct tgataggatt gcagtggaaa attaaatgaa ataatgttag caaaggtccc    111720
aacataatat ttgacttgga attgaatgcc catggtaacc agcatcattt tccttcatgt    111780
gatgtcttct tatgccttttg aaagaaagtt actttatcaa atgtataaat aaagatctgt    111840
ttataggtga tcttttttaat ttagaagaaa ttctgagaca caaataaaaa aagaaatttt    111900
ttattatgtg gttcaataga ttgtctaaag catggcagta aagttttaat tatgccaaga    111960
tgcttcatat ttgtttttaa atgaaattaa gttgtattta tgcttcttta gtgaaaacaa    112020
cgttacttaa ctgctacagg aagtgtgaat agtgataaca gttcttttttc tctcagtgtt    112080 tgaaatattt tcctgaattt tcttagtttt ctcatacctg aatcaagaac cctttttggtt    112140 tgtttcataa acagtaatct agttattatg ttcagctttt cagatttata atagctgatt    112200
gttctcagca aattaaacat gatggtcaac gctaatacta ctcaattatg aataagtgcc    112260
attgtgtggg tcttcatgtc ttagactcac ttatagttag aataccaact ggttctatgc    112320
tatttattgc aaacctcaga taaatacacc attaattatt acacacaact ttaaagcaat    112380
aaaatcagta gataaagccc aattttacct ttctctctct ctatatatat atatgtatgt    112440
atatgtacat acatacacac gtgtatatgt atgtacatat acgtgtatat gtatgtacat    112500
acgtgtgtgt atgtatatgt atatacatac atacgtgtgt atgtatatgt atacacatac    112560
atatgtatgc atgtatatac atatacatac atatatatgt atatatatat atatatattt    112620
tttttttttt tttttttttg agacagagtc tcactctgtc tcccaggctg gagtgcagtg    112680
```

```
gcacgatctc ggctcactgc aacctctggc tcccgggttc acgcaattct cctgcctcag    112740
cctcccaagt agctggaatt acaggcatgc gccatcacgc ccagctaatt tttgtgtttt    112800
tagtagagac agggtttcgc catgttggcc aggctggtct ggaacttctg acctcaagtg    112860
atcctcccac cttggcctcc caaagtgctg ggattacagg cgtgagccac tgcgcccggc    112920
ccaattttaa ctttaatatc acaattttca cctacattag tagaatatta aaagtaaaca    112980
tgctatttct ttggcatttt agttgaggtc aaataatcct cttccctaat tactgtgtaa    113040
acaaatgtag acaaggtaag cacgaatgag acaggatggc ctatatggag tagtaaggtg    113100
ttgaagttta gaggccagcc tagaagactg aggaaaaaag ggtgagaatt acttgataag    113160
attgaaggta tggtaattgg aagtgggagt atactgagat ggatatttca aattcagcaa    113220
tatgaagagg cagtgatcaa gtcaaaactg taggtggaaa atcagcaagt ggagaaactt    113280
aagacggaac acggaggaaa tagagtgcag attaaataga aattgctatg ataacatgga    113340
ttatattctg tgattgccat tgaggtggag ccaaagtgaa ggagtaatgg agaaagtcta    113400
gattgctaat ttcaaatatt tgaggttatt ccagtattta ttattgttat ttattattta    113460
tttatgtaca tatggttcct agcagagttt ttcaagacta aacaggcttt tgatctacag    113520
tcaaaagcat tgatgctatt gagagggaat ggaacagaaa gggactgggc aagttacagt    113580
aatgactgac aggactgcta tattttttaaa agtaataatt ttagatttat agaaaagttg    113640
cagagatcat acagagttga ctcctgggtt ttgatttgga agatgtgagt gttgggagga    113700
caaaagagga aggattatac acagttttct atttagcaga acgtgaatgg aacacattgg    113760
aaagagggcc tgggcatagg aaataggatg tctagaatct aggcagccat gcacagtttg    113820
ggtactccag gtgtcaagcc atgtggctct gcttctaggt gaccaagttc aattgaaatc    113880
tctagtggaa ggtgtgtccc tcctagagtt ggagcagacc tcacaatttt tcacaagtaa    113940
aagaagagca gaaaaacttt tatacaggtt tcagatgttt atattattga acactgtaaa    114000
atataattat tgttttcaaa tgaataaaag ataaacctga gactatcaca aagatctata    114060
aaataatagc agaacttctg gaaatgaaag tacagaaact aa                      114102
```

<210> SEQ ID NO 3
<211> LENGTH: 48646
<212> TYPE: DNA
<213> ORGANISM: Homo sapiens

<400> SEQUENCE: 3

```
aatggatagt tggagtggca gattgggcac agagaagtaa ttaactagaa gacagatctg      60
tagaaattct tacgtagcat ggagacaaaa aggtagaaaa tacaaaggag agggttaaaa     120
tgtggatttg gcatacaact aataccacat gtttgataac cacagtttta gaagaaagaa     180
aagaaagtgc ataggaaact aagaggcaat gagaattttc cccaaattga taaagatagc     240
aacccataga ttaagaaac tcaatccaag caagaaaaag taacatccac acttagatca     300
gtgaaattgc agatcaacaa agacaaagac aaaagagatt agcaattaga cactctcaac     360
aatagaagcc aaagtacatt gaaattatac tttaaaaatg ctggggaaaa cattaaataa     420
cttccaacat agaattctgt attgaacata cctttcaaga atgaaagcga acttcccggt     480
cgctgaaaac attagtggca gcctagctac ctgtctcccg atatttcatt gcaaataat     540
gcaagcacac gaaggaaaaa gtatacagaa atcacactct cagcataatt tgaagtcaga     600
gaattttgaa acttcaaact gagtaagatg aggaaaatca gcagatcgca acatggattc     660
tcacaggccc accccagcag catcccacag gctctgtgga gcgaagccag atggagataa     720
```

```
actgcaggga agtcaggaga gggacgccag aaaaagaaag taatgttcta atcttggcct    780
aaaactactg ccagaaagac taggtccacc taactctcaa tctcaaaaac atgtccaagc    840
agatccgggc agaaaccaga ggcaagaggc ttcagagtga gcacaattta aaggggggcag    900
gtgtgactta atgaggcagt ctttgaaaca cacagcttca aaagaaaaga aaagaagagc    960
gtctagtgaa gggaaaaatg aaaaaaggag aagcacctttt gacaattagg tgatgaaaag   1020
aagcaaaaga aaattaggtg atgaaaagaa gaaaggagg aaattcgagt cctgctagtc    1080
aaatgagaac tgcaaaatca gagcacttac aactcctccc cgaacatgcc aacaaaaata   1140
cctactaaag tatttaatac cttagctttg ctctattatc agaacagatc tcagccatga   1200
aacatgaaaa tataaatagc atatatgaat gaatattgat aagatgaatt tgtcattatt   1260
agatgatatg cttatatata tggaaaatac aaaataatct acagataaat tagaaataat   1320
aaaatttagt tccacttcca gctgtgagtg gattggcttg aaatggaaag acttctcgtc   1380
aagagcaatt agaaaagcta aattttattt taaaaaaaaa ctgtttgaag gattggagaa   1440
ctactaatgt aagaaggact tataggatca agatcccgga acaaaagag ctgagaggtg    1500
agcatgatgg taaaactttc acctccaggt atgtttcaat tcataggtga cagaagagag   1560
gccaggcaag agacagagaa ctcaaacaga agttttaggc agtatcactg ggtggaggaa   1620
aatatgaggt tagcacctgt caaggaggtg gcactggtaa acagtcttcc agttaggaaa   1680
cctgaatggc tagacattag aattaagggt taaccaaaaa tagaccaatt ttaacaaaca   1740
cagaatccct cttggtatta gttccacccc atactggatt aagctgatct gcccctacct   1800
gaactgcctg caagaagagg cagtaaattc tttctggaga aagacaacat catctagatc   1860
ctcaaatgat taatacaaag ttgtatctat aatatatagc atccaatcaa aagttcttat   1920
tatcaaaaga caagattaaa ttgtgaatga tcaagaaaaa tagaaacaat cctatgggaa   1980
gtacagattt ctcagttatc agaaattttt aaagaatgat gatgggccgg gtgcggtggc   2040
tcacgccttt gtaatcctag cactttggga ggccgaggtg ggcggatcat ctgaggttgg   2100
gagtttgaga ccagtctggc caacatggag aaacctcatc tctaataaaa atacaaaatt   2160
agctgggcgt ggtggtgcat gcctgtaatc ccagctacac gagaggctga ggcaggagaa   2220
tcacttgaac tcaggaggcg gaggttgcag tgagctgaga tcacgccatt gcactccagc   2280
ctgggtgaca gagcgaaac tccgtctcaa aaaaaaaaa aaaaaaaaa aaagccgggc     2340
gcagtgtctc atacctgtaa tcccagcact tttgggaggc tgaggtggga ggatcacaag   2400
gtcaggagtt cgagaccagc ccaggtaata tggtgaaagc ccatctctac taaaaataca   2460
aaacttagcc agtgtggtgg caggcacctg taatcccagt tacttgagag gctgaggcag   2520
gagaatcctt gaactcagga ggtggaggtt gcagtgagcc gagatcgtgc cactgcactc   2580
cagcctgggc gacagagcaa gactctgtct caaaaaaaa aaaaaaaaa aaagaatgat    2640
gatgaatgaa ttcaagaaag tagaagacaa gatgaagaat tttagcaggt ttttttttt    2700
aagacagggt cttactctgt cacccaggct ggagtgcagt ggtgtggtga tggctcactg   2760
cagccttgac ctccagggct caagcaatcc tcccacttca gcctcttgag tagcgggact   2820
atagggcgca tcaccacgcc tggctaatgt ttaaattttt tgtagagatg aggtcctact   2880
atgttgccca ggctggcctc aaactcctgg actcaagcaa tcctaccacc tcagcctccc   2940
aaagtgctgg gattagaggc atgaaccact acatccagcc cgataattaa acatttaaa    3000
aattaaatca acaatttcac ttctggacaa aatggattag ctgtatttct ttctattttt   3060
cccactaagc acagcaaaaa aaaaaaaaat catatatata tatttttaaa aagactcaaa   3120
```

```
aaggtggaaa gaagaaggca gaccagctaa ggacctcaga atgtaaagaa catgaaggtg    3180
agttccctgg gtttccttt tgtttcctat gtcctatact gggtgctgga gaaactggca     3240
acctagaaat gccaaagggt gcagacaaga aaagtccaaa ggaaaatgga aagccttctc    3300
tctccagaca agggatgagg aaacaggtat cctaacaaga cagaatactt ttggacaata    3360
atttcaccac tctggacaaa tgccacagaa aaaactgagg cccatcttca ctccttgcca    3420
tcaaaggctg agtgaggagg ctaggcttcc acactcacct ggctctaatg aagcactcca    3480
cccatccccc acttggactt ctcgtccatt gcacagcagc aatgaggctc cctgccatgg    3540
tggcagtggg gaccacatgc ggagcagtaa caaggcaccc cctccctggg gaatcagtga    3600
aggccaaggg agagcctgaa cttccactgc cacctggaag tagcaagcat ttccctatgt    3660
cccccagcag catagtgtca gaggaagtct gcttaaacag aagacataaa taagatcaga    3720
atctcataac aaatacctga acatcagga tacaatttat aaaaattgtc attccaatag     3780
cccagagaac ttcgacttga gtgaaaaaaa gacaacagac cccaacatca agatgacaca    3840
gatgttggaa ttatctgatg aggactttaa agcagctcta ataaaaatac tttagtgagc    3900
aattacaaac aaacttagaa caaatgataa acgagtctc agcaaagaaa cagaagatat     3960
aatgaggaac tgaacagaag ttttagatac gaaaaatgca ataattgaca tgaactcaac    4020
gaataggctc aacagcagaa tggagggaac agaggaaaga catactttct gtcagcaaat    4080
ctgaagacag aatagtagat agtaccaaat ccgaatgatg gaaaatagac tgaaaaaaaa    4140
ttagcataac ttcagagcta tgtgggacat taacacaaga tctagcattc acgtcatcag    4200
actcccagaa aaagaagaga aacagtatga gacagaaaaa gtattggaag aaacaatggt    4260
tgagaatccc ccaaatttgg cagaagacat aaatgtcaga atcaagaagc tgaggatatc    4320
ccaaacagga taaatccaaa gaaatctaca ccaaggcaca tcataacttc tgaaaactaa    4380
agaacagttc ttgaaagcag tgagagagaa aatgtatttt agctacagtg aaaaacaat    4440 tccaattta gtcaatttct tatctgaaac tatggaggcc agaaggaatt ggcacatttt     4500
tcaagtgctg aagaaagaaa ttgtcaactt cagattgtat atctggcaac aatatccgat    4560
cccccaagaa tgaagggaaa tcaagacatt ctcagatgaa gaaaaactaa tagaatttgt    4620
caccagctga tctactcttt aaaaaaaaaa tggctgaggg aaattcttga acagaaagg     4680 aaacgattag aaaaaggaat cttgggacac taggaacgaa gaagagtaaa atatgcataa    4740
atcaagtaag ctttcctctt ctcttgaatt ctctaactta tgcctgaccc ttgaagcaaa    4800
tattgtaaca ctgatgtggt tctcctcaat gaatgcagag gaaatactta aaaacaacta    4860
tattataaat gagtggggga aagaactta caggaattaa ggtttctaca cttcactaga     4920
attaagtcag caccggtaga ctgtgataat ttatgtatct ataaagtgtg ggtttggaca    4980
gcagatttta tcaggttgag ggctcaggcc gagagcatgt agaagcagtt agctcactct    5040
ttctagatgt ggcggctgac aaggacaaag agggctggga ctagaactgc tgtagacaag    5100
gaaagcagcc agtggagaag agcgcatacg ccaaagaacg tggatgatgg agcacaggcg    5160
gggaggtagg atgaaggaaa tggctctggg aagaaagggg ctctatgtct gagaaaggaa    5220
gaaattggct gaagatacaa attagagaca aggtgaggga aattgaggga gttgcctgag    5280
gatgattctc ctcccagtca gtaggcacc tgctgagaga aaggataagc cgagatgagg     5340
gagatgatga tggtttgggg cgcagaaagc gggaatgaaa gacaggagct aaagccgaag    5400 tttttttctct ctcgctactt aaaagctgta agataacgaa ttgatcagca ggtggcagtg    5460
tccgcggagg ctcgcatccc gtcggccctg gctctcaagg cggaaacacg caccatggtg    5520
```

```
actttccggc ctgcatcgcc tctgctcccc tatcccggct gacgttggac gacaaagatg    5580
gcggcaggga ccagcagtta ctgggaaggt gagggcgaga aggcctccgg gtgcgtccta    5640
cgagggtgag aggggctgag tgaggacaga tcttgggaga agcagcacag gaaagaacca    5700
gactcccgga gcggccgagc tgagcagcgg ggcttgccta agtgggatcc ccggggcctt    5760
ggggataccg aacggtctgg ggtaggggtc tggcctggcc ggggcgtgtg agcgggacgt    5820
ggggcagggg ttgggcagag tggacagagc ggggatgtag aggaagaggg ctctcaatcg    5880
cctgggtaga attgtgttga gggagtaatg gaactcggac gaaggggctt ggggtacgaa    5940
ctctgagagg aaacgaatgt tgagggagaa gatccagagc cccggagact ggaggagtca    6000
gcgcattgga gctgaggtca ctattggaaa actgagtggg aaagagaag gaggaacttg     6060
cattccggtc cgtcggagga agtatgaaga gaataggaga cagaatgtct cttattgggt    6120
ctccatgaca actacaggtt ggggacttcc aggactgggt gtttgaagga ggagaaaata    6180
acttacccct ctgctctaga gtctagaatc ggttttattg aaaagttga gagaacctgt     6240
gtgaattgca gttacatttg ctatacttct cccaccaaaa aaaccttcct gtgatttgac    6300
aaatgcattt gtttaattcc tgaaactata gtcggataaa gtgagcttac ataaaactca    6360
ttcgtggatt atgatgatca acaagagcag agaaagctca ccttttctc ccaactgtct     6420
ctttgcttta cagccgcata gaaactactt tccaaattcc tttgacctgt ttttattgct    6480
atacactgaa gcctctagaa accacagtat tgtcactatc agccccttgg tctaagaaac    6540
tcaattctaa atttatccag atttgcctat catacttttca aaatgctttt acttatgttt    6600
cctactagag aagacaatta ttccaatcac agaaaagcgt gcttatagtt taaaacatgt    6660
attacaatgc ccatttgaaa tgtgtgtacc agctagaaaa cttttttttt tttttttttg    6720
gagactcgct atgtcgccca ggctggagtg cggtggcgct atcgatctcg gctcactgca    6780
gcctccgcct cctgcgttca gcgattctc ctgtctcagc ctccttagta gctgggacta     6840
cagatgcatg ccaccacgcc tggctaattt ttgtattttt agtagagacg gggtttcacc    6900
atgttggcca ggatgttctt gatctcctga cctcgtgatc cgcccgcctc tgcctcccaa    6960
agtgctggga ttacaggtgt gacccaccgc gcctggccgc tagaaaacat tttaaaatta    7020
tgtagaagag gctactgata tctttattac tagtcattag cctgtggttt tttgaagcag    7080
catgctataa tattacagcg gctcattact gacaacctac tctgtgccag ctgctgtaag    7140
catatgatta ccaatacata agcaaaccct gaaggtaggg gtttaaaaaa caagaagctg    7200
aagttcatag gttaagtaga ttgttgataa atcatagagt cagtaagtgg ctgtgccgag    7260
attcgaactg gcatttggtc tctgggcaaa tatgctccac tatgttaact acgctttcta    7320
tttctggttaa aaagcatat tgaaataatg ttttgtattc tttttgaaag agagattctt     7380
ataccattac ctctggtact tctgccttt tatttaacc ttcacttcac catgaatgag       7440
aatactcgta tctgtgtgtg ggtgtccaga ctgtggcttc tgtcacgcaa cccttagatg    7500
ccagactgct aaaccaattt ctctacttgc ctgtttgctt ctgctattaa aacttatgta    7560
cttatttcta tcatactcat attcgacctt gttagtagca cattgtttat tgttagtttt    7620
agccctccaa attactttca gtaagttttt ttctttttt tagatggagt ctcgcactgt      7680
cgcccaggct ggagtgcagt ggctcaatct ccactcactg caaactctgc cttcagtgc     7740
cttccaggtt cacgccattc tcctgcctca gcctcctgag tagctgggac tacaggcgcc    7800
caccaccacg cctggctaat ttttgtatt tttaatagag acagggtttc accgtgttag     7860
ctaggatggt cttgatctcc tgacctcatg atccgcctgc ctcggcctcc caaagtgctg    7920
```

```
ggattacagg cgtgagccac tgcgcctggc ctcagtaagt tttttaaagg cggttttTgg      7980
ccaggtgcga tgtctcatgc ctgtaattct agcactttTg gaggcccagg caggagggtc      8040
actggagttt aggagttcga gagcagcctg ggcaacattg tgagaaaaaa cagaaaagaa      8100
aaaaagaaag aaaaaggcaa ttttTgtggt aactttttTt ctttatgttc aattgagaag      8160
tcatttTggt ccgggcgtgg tggctcacac ctgtaatcct agcactttgg gaggccaagg      8220
tgggtggatc acttgaggtc aggagttaaa gaccaccctg gccaacatgg tgaaaccccg      8280
tctttactaa aaatacaaaa attagccagg catggtggtg tgtgcctgta gtcccagcta      8340
cttgggaggc tgagagttgc ttgaacccag gaggtggagt atgcagtgag      8400
ccaaggtcat gccactgcac tccagcctgg gtgacagaac gagactccat ctcaaaaaaa      8460 aaagaaaaa aaaggtaag tcatttTgct attatgaaaa gaagttcata agcctaataa      8520
agctttggaa cataaaaagc aaaatcccTT tcaaagaat aatggcTTct ttcTTataac      8580
attaactggt aagttgataa tgctggtcat aaaccatatt tttagttcct ttgtgatttg      8640
tattatcTTc ttgttTTTct ctgaattgca gaattttagt tattgctata caaatagttt      8700
caggaaggat agaacaacat ttgttTTcta gccatctttg gagtaaagct gcgaagttgc      8760
atctaccatt actatttccc ttctTgcccc ctctgaagtt tataagtgac taatctgctt      8820
tgctgggcaa gtccTTggtt tccTTcttTT aagactTTTa tTTtcctTTT tTTgagacat      8880
agtTTTgttc ttgttaccca ggctggagta cgatggcgca atcTTggctc accgcaacct      8940
ctgcctcctg cgttcaagcg attctcctgc ctcagccTTc cgagtagctg ggattacagg      9000
cgtgcgccac cacacctggc taatTTTcta tTTTTagtag atagggtt tctccatgtt      9060 gatcaggctg gtctcaaact cccgacctca ggtgatccgc ccaccTTggc ctcccaaagt      9120
ggtgggatta caggcgtgca ccaccgtgcc cagccaacac tTTTcTTtat ggggtaaca      9180 agatcagtat atgatcattt tcatagtTTTg tTTTctTTag aatggtgctg tgaTTTTgt      9240 gtctacttTT tatgtctaat taTTTgTTgt tataaTTTTc ttaaagatct caggaaacag      9300
gctcgacagc tggaaaatga acttgacctg aaactagtTT ccTTcagcaa actatgtaca      9360
agtTacagtc atagcagtac ccgagatgga agacgcgaca ggtataggta ctaccagatt      9420
ctgtctccta tgccttaact gtgtTTTTaa agcattaaaa aataaactaa aatatataac      9480
ttctgtaagt tggtctattg gtgaatTTTT ggtgTTTTgt tTTgccatTc attgTTTTat      9540
tTTTTagtga cttattaaaa ttcTTctgaa ttctcgagac tagcatttat ttggaatcct      9600
taggcaaaga ttgttacagt gtcagaagaa acctgctaga acttcagaat aagtTTtgtat      9660 caaaaatata agtgtctaat tcagccagtg tagggaaaag gtggctgatt tgcccgtgtg      9720
gcatgtaTTT cttgtgTTTT tcaattgcta aatggacctg tggatctacc caggtgccag      9780
gtatacatac tgcTTTTctg gtgTTTatTg tattagaggg tatctaatgc actgtgtatc      9840
cttgTTatta aTTatcaaag ctatcTTTaa tTTTggtact tTTTTgggaa actagtgtat      9900
taccatatta aatgtatgga aaatacattc ttatcTTTga agcTTatgct ctctgtaagt      9960
catccacttg tTTTcaagaaa atattgggag tagccaggca cagtagatga cgcgtgtaat     10020
cccgggactt taggaggttg aggcggatgg atcacttgag cccaggagTT caagactagc     10080
ctgggcaaca tggtgaaacc ctgtctctaa aaaaaataga aataaaaaaa atTTTTtaa     10140 ttaggcaata TTTaagacag ttacaaagaa taatatcatg aacccccatg accctatctc     10200
ccaTTTTTaa aaaatgataa ttactcaTTc cactgaagcc ccTTatggca ccccactTTc     10260 tcccaccccca taatccacat atattcTTac tgcatgtTTta taTTcctgag caatTcatag     10320
```

```
tattctatta tgttatatag tatatatata atatagttat tctacaactt tttctttaac    10380
atttttgaga ttcagctatg gattcattta actctggtat attcatttgt aattcatatg    10440
tagtatttta tgactatcac agtttaacca tttgatgatg gccattgttt ctaatttttg    10500
ctaattaata ataattttga tagctgacat aagagtgttc attatatgtt aggtaagagc    10560
tttctataaa tgctgctggg aacatttta cgcagaatgt ttctatatac ctagcggtga     10620
aattgctggt agcagagttg ttgttaatcc acacttattt tacatacttt ttcaaagatt    10680
agaagtgagt aggatatttg tcagctaata aaaacaatga aatctgagct tagatttgaa    10740
tctagatcta tctccagagc ccacactcta aaccctacta tagtgtatac atttgaacaa    10800
aaagctgatt tcaacactat agccaaatta ctatttcttt ttcataagga ctccttggtt    10860
gtaaaggcag caaggccaac attgactcta ggatctaaaa ataaattact aacacatcaa    10920
atagattgca ttgctttggg cttggcttta tttagcaagt aaagagaatg aagaatgttc    10980
tttctatgca ttttctatgt tctgtgtgct tcatgaacta atacttttgt tattcctcta    11040
aaggaaaaac tatcttgaaa acatttccca agaaattcta ccacaaactg aaactggctt    11100
tgtagaatta cttcagccta actccccttc taaataaaaa cctaaggcca tgaggatcag    11160
gatttgatgt ctattctaaa gtgtcttgtt tgatgcccag gttggaagca tgtcactatg    11220
agtcaactaa gcaataacta gaatattatt tattccaggc atctttcttt cttttttttt    11280
ttttttttaa ctttctgtat tttgagaact tcaaggtcta tgaatcatta cccacctata    11340
agatgaatta aatttaactg aatcccagta ttgtgaagaa ttagtgtttg gccatttccc    11400
tttactctta cactgtcctg atgaatatat gaatacaatg agtatagaat aaccagtagt    11460
agagattgct ctcgtgttca ttcatttatt cagcagaagt ttaatgagca tctactatgt    11520
gccaggctgt atactaggtg ctaggcatat atctatgaat aagacagagc agttttttcc    11580
ttccttcatg aagctttaat tctattggca tattgttctt tttcatatat ctggtagagg    11640
aggatttata ttagtagtct acagagcatt tatttaaatac ttttcatttg ccacacccag    11700
gcactgtcac agggtagcac aaagtcttca gtaagattgg agactatagt cattgcctgg    11760
gcatttatct gtgtccagta taactctgat ctgtattgag ctgctcatca gatgctaata    11820
catacctaac ctgatgaagg ttagtggtgt tttggaaaag gcaaaagaaa cactgaggac    11880
aggtgggttt agaatttgaa tctgtcaaac ctaagtttca cttgtaaaaa gatagatttt    11940
tgactattca gatttgaaaa ggcaatttaa cacaattcta caaaacaaaa ggatgattgc    12000
atactgtaag tgaaaatgga gaagattagt accaaagcat gcaggacatg gctgtatata    12060
ttggatttaa agccagttcc tgagtattcg ttagctagtt atccaatctg tggatcattt    12120
aaacctcaat cttatttcct cttggtaaga gtcaaggaaa gaagagagaa tgtaatgttg    12180
aggttgaagg aaccataatt cctttggggt aaaaatgtaa aagatcgttt ctcacagacc    12240
ctatataaca taatccataa ttcatttat ggctcctatt aatcacctta ttattttaag     12300
tatgttttaa aggactgatt tgagtaatgg atcctctta actgaacttc tttttagttc     12360
tgatacaaca ccccttttaa atggatcaag ccaagacaga atgtttgaga caatggcgat    12420
tgagattgaa caacttttgg caagggtaag tgctttctgt taaatggcta ttttgcaaat    12480
aactgtatac ttgttacgta ggatcctgga ttatattgag acagacatgt ttattgaaat    12540
tatccattcc attcaatatg tgtacctccc cacaccactt gaattttgat gacagccatt    12600
ctcaggtgat atgatgttat tttggtcttt atggattatg tgggggaatg ctgaattctt    12660
acttgctctc ttgtttgttt tttgttttgt tttgtttttgt tttgttttgc tgtcaaccaa    12720
```

```
aagggcatat aggcaaataa tttgctttta gctgtttata gtgcttagta aaatattttg   12780 attgttttt ttttctttat ttctagctta caggggtaaa tgataaaatg cagaatata    12840 ccaacagtgc aggtgtcccc tccttgaatg cagccctgat gcatacatta cagcggcata  12900
gagacatatt gcaggtaata tattgggctc gagatgtttt cattatcaca ggagtttggg  12960
tttttttttt tttaatccct gcattggata tgtgcacata tatttaaaag gacaaagaga  13020
aaaatctgag aaaataaatg ccatgctaaa gggacttgtt ttactttttt ttggggtcac  13080
cattataaaa ttctgaaaat atctaatagc tcttgctatt tcttggcgaa gttgagtaat  13140
attcatcact gggtacatat acttccacta tgggagacct agctagctag ctgtaacagt  13200
gaaatagcca atggtcatgt atagacaata acgtggtggg taagcgtgta ctttcagcta  13260
gctttgaaga taatatggag ggggaattat ttactatact tagtatattg tttaagaaaa  13320
cagtaaatgt gtatgcacca ataaaactaa ataaacttttt aaagatttaa atggaggata  13380
tgttaaaaat atggtagtac aaataggaag gcaattttt ttttttttt gagatagggt   13440 ttctctgtca ctcaggctgg agtgcagtag tacagtcaca gctcactgca gcctcaacct  13500
cccaagctca acaagcctc ctacctcagc gtcctgagca tctgggacca caagcacatg   13560
ccaccacgcc tggctaattt tttaaaagct tttgcagaga caggtccttg ccatgtttcc  13620
caggctggtc tctaactcct gtgttcacga ggttttgcta tattgcccag gctggtctct  13680
taactcctgt gttcacaggt ttttgctatg ttgcccaggc tgttctctta actcctgtgt  13740
atgggcaatc caccccctca gccttccaaa gtgctagaat tataggcatg agccgctgta  13800
cccagccaca aatattttta atattgagaa aagtcagcaa ctatttctaa ttttaaaaac  13860 tgttttaaa agtaggaata gatggccggg cgcagtggct cgtgcctgta atcccagcac   13920
tttgggaggc caaggcaggt ggatcacctg aggtcaggag ttggagacca gcctggccaa  13980
catggcgaaa ccctgtctct actaaaagta taaaaataag ctgggcatag tggtgggcgc  14040
ctgtaatccc agctacttgt gaggctgagg caggagaagc ttgaacccag gaggcggagg  14100
ttgcagtgag ctgagattgc accactgcac tccagcctag gctacaagac tgagactcca  14160
tctaaaaaaa aaaaaaaaa aaaagtagga atagaaagat actttaatac aaaaatgtat  14220
tatcgggtta aaagctagca ttgtgtttaa agagaaagca ataaaaacat tcccattgta  14280
tgaaacaaga caaggatacc catgatcgct acaaatgtat aacgttgttt tttaagttct  14340
tgatggtgca attagacagt aaaaagaaat gaaatgtatg ctgggcatgg tggctcacac  14400
ctcttatcca agcactttgg aggtctgagg tgggcggatc atttgaggtc aggagttgga  14460
gaccagcctg gccagcaggg tgaaaccct tctctactaa aaatacaaaa attagcgggg   14520
cgtggtggtg ggtgcctgtt atcccagcta cttgggaggc tgaggcagga gaatagcttg  14580
aacattgaac ctgggaggtg gaggttgcag tgagccgaga ttgcaccact gcactccagc  14640
ctgggcaaca gagtgactgt ttcaaaaaaa aaaaaaga tgtaaatatt ggaaaggaag    14700
aggcaaaatt tctgtgaggt agcaggataa aattatatgt ctagtacacg caagaaaatt  14760
acctgataaa aagttagaaa caattaaatt cagtaagatg gtagatcaca aaatgaatac  14820
ataaaagcaa atagttttcc tattatgata ggaaataaat gataacctgt tagaaaatac  14880 aatgaagaa actataaagc atttatatat gaattaaata agaaatgtgt aggacttgta   14940
tgtgcagaat tctactgagg gacatagaac aagatttaag taaggaaag aatcattctg    15000 tttttggata ggaagacttt cgtctaaatt gcatgacatc ccagtggaaa cagcagggtt  15060
gtatcgttgt ttgtttaatt aaaaacaaat gacataatga caccaaagtt catttggaat  15120
```

```
catagacata caagaacaac caagaaaaac aacctgaaaa tgaagataag tggtagaggg    15180
ttcctagttc taccagatct taaaacctgt taaaaagctg gaatagttaa dacagtttga    15240
tactagagaa aaaaaataaa taaataaaaa caattaaaca gagtttatat gtagacccaa    15300
ttatgtttgg aaatttttag tttctgataa agatgttgtt taaaatcagt ggggcaaaga    15360
gaaattataa aataaatgga actataacca ttgcttaatt attcagagat tttaaaaaaa    15420
caattctatc tcaatcctca catccagaac aaattccaaa tggatccaag aaggatagaa    15480
aaagaaacca taaagcagag gtgaaatttg taaactttgg agcagaaagg actttctaaa    15540
taagacttga tactggaaac cataacgaat ggctaatttg cttactacac agagatataa    15600
tagaaataag aaaaagacag taggaaaatg gacaaaggat ataaaattgc ttacaaaaaa    15660
atgaatggcc aaaactataa aaacattttc agcagtattt ccaaataaaa atacagaaat    15720
ctaaaagagg tgattttttca catgtcagat tagcaaatgt tgaaacattt ataacccatt    15780
attggcaaga gtaaaaattt aaaaagggta ctcatatatt gctggtggga acataaattg    15840
atgtaatgtt tatagaaggc agtttagcac taccagaatt taaatgaatg tgagattctt    15900
tgatccagtt attcttttt ttttttcttg agacggagtc tcgctctgtt gtccaggctg    15960
gagtattgga gtgcaatggt gcgatctcgg ctcactgcag cctccacgtc ctgggttcaa    16020
gcgattcttc tgcctcggcc tcccgagtag caggaactac aggtgtgcgc caccacgccc    16080
agctaatttt tgtatttta gtagagatgg ggtttcatca tattgatcaa gctggtcttg    16140
aactcctgat gtcatgatcc acccacctcg gcctcccaaa gtgctgggat tacaggcatg    16200
agccaccgta cccagccctg atccaattat tctattgcta gtcatttact ccttttttt    16260
tttttaagc tctgttgaac ttaatagaca tttactcttt aaatatactt tttttttt    16320
tttttgaga cagagtctca ctctgtcacc caggctggag tgcagtggcg cggtcttggc    16380
tcactgcaac ctctgcctcc cgggttcaca ccattctcct gcctcagcct cccgagtagc    16440
tgggactcca ggcgctcgcc accatgcccg gctatttttt tgtattttta gtagagatgg    16500
ggtttcaccg tgttagccag gatggtctcc atctcctgac ctcatgatcc gcctgccttg    16560
gcctcccaaa gtgttgggat tacaggcgtg agccactgcg cccagcctaa atatagtttt    16620
ttttaaaata aaagagttca gtttaaaaaa tatatgtaag aatgtttatt ggcagtattt    16680
tttttttt tttttgaaac agagtctcgc tctgttgcct aggctggagt gctgtggtat    16740
gatctcaact cactgtaacc tctgcctccc aagttcaagt gattctcctg cctcaaactc    16800
ctgagcaaag tagctgggac tacaggtgcg ttccaccaca ccggctaagt tttgtgtttt    16860
tagtagagac ggggtttcgc catgttggcc aagctggtct cgaactcctg acctctagtg    16920
atccgcccac ctcagcctcc caagtgctg ggattacagg catgagccac cctgcctagt    16980
cttgcagtat ttttaatagc aaacaaatg aaaacaacta atgtgtttat cagtagggaa    17040
tttattaaat tgtgatagtc ataagataat attctatgca gctattaaaa agaatgatgt    17100
agatttcttt ttcctaatat ggaaagattg cttgatactt tatgaagtac aaaaagcaag    17160
gtgtacatca gaatgtatat tatgacttac ttggcaaagt gaaagaaata atagataagc    17220
ttgtatatgt aaaaacatat ttcctggcca ggtgcagtgg ctcacgcctg taatcccagc    17280
attttgggag gccagtgtgg gtggaactgt tgaggtcagg agttcaagac cagcctggcc    17340
aacatggtga aactccatct ctattaaaaa tacaaaaatt agctggatgt agtggcacgc    17400
tcctatagtc ccagtactag ggaggccaag gcactagaat cgcttgaacc caggaagtgg    17460
tgtttgcagt gagctgagat ggcaccacta tactccagcc tgagcgacag agcaagactc    17520
```

```
ttgtctccaa aaaaaagaa aataataatt tcctggaaga aaatacaaaa tgatggtaac   17580
agttatgagg tatggagcag aatgttttgt tttcctttgt ttcaccttta tttcttttgg   17640
tgctctttta atattctcct ccatgtttat gtgttacttt tgttttttaa aaggtcaaca   17700
gggactctgg gagacaagat tttgattttc ttctttatct acatctctga atttatgaaa   17760
agtaatgaag tacttttaac agtggtacaa aaatagtaga aaatgtttaa agattatttt   17820
gttccttata attctcttga ttctgttctt ttttgtttag gaattaaatt ttttgtgaga   17880
gctccaaaat gatgaaattt gaaataagc tctattaagt atactactaa gtaaaagag    17940 cctctcaagt tttctcctag actatttgaa gttattttat ctcagaattt ttttcttctt   18000
aattctgcct cgtaagacag agtactagga ggtacaaagg atagtgattt aatggcactg   18060
tttccctagc actgaattat tttcacttga aagaagttgg tcactcttca ggaaagtaat   18120
tttaaagtta ttttaccct tggttaattt gatttcttaa atagcagttt tcttgacaaa    18180
tttacagtgt gatgacgata cataactggt tcagtgagat gaaatccat aattagcttc    18240 tgttgagact ggatgttgat ttattacagg attatacaca tgaattccat aaaaccaaag   18300
caaactttat ggcaatacgg gaagggaga atcttatggg atcagtacga aaagatattg    18360
agtaagttac tttttatatt attttgtaga atatttattc agatttggct ttaggatatg   18420
ttcacggtta attgcaaatt gagtggcaga accgtggttg agattttagg gtttccaatt   18480
cccatttcac tgtctttta acattgctgc tacaatgtca tcctaatcta cttttccatt    18540
tttatctcat gcttcctctt actttatcat tggctcctgc caaccttgac tttcctgtct   18600
taattcaaag tccagcttag gtggttcttc atggttctct gatctcttac ctcccaccct   18660
aagaattata atgttacttt tatgatcctc tgcagatgtg tcaaagaaaa aaaaattctt   18720
taattgtaac attatcagta actgaagctc cctatgtttc tcttcctgat tatcacctat   18780
cccctggccc tctcccttgt cccaacagtt acatattaca aacagtaata tgtacaaact   18840
cactcatagc cttatgttaa attatttaag gactcccaac attctcatac tgatctcaat   18900
ctataatttt aaatatttgt tttttcttc tgtcccttca cctcacctt aatgatctat     18960 tctagcattt catagcattt ttggaaattt ttttacaact gaacactact gacaaagtta   19020
agtcccatgg gcgtctcatt gaagctgaag atgttccaat ttggagccat ctaatgatac   19080
ctgtcatcat ctcatttgtg ataaattatg tgatacattt tataaactat gatacacatt   19140
tatggtaaac tgtatattat gtgtactctc gaaaacactt tcctagagat cctttatttt   19200
attgtaacag taacagtttc aacagtaaga ttgttgtaat attttagtc cttcaggaca    19260 tttaagtctt ttgtttaatt tccatgtagt ccatttatat atatgttttg aggaatgcat   19320
tgggaaccca tatagggat ggtctttaat gtatagacac tgagccccc cataatttgt     19380 gggaatcact agaatgcaac ccattgtaat aacttgcttt ttgaaaaatg gccataaaag   19440
atatgttcat ctattcatta aactgtctcc tgagtatcaa ctctgagtta gtcacagcag   19500
aaggtagaaa tgaaaagacc ggccaggcgt ggtggctccc gcctgtaatc ccagcacttt   19560
gggaggctga ggcaggtgga tcacttgggg ccaggagttc aagaccagcc tggccaacat   19620
ggtgaaaccc cgtctctact aaaaataaaa aaattagctg ggcgtagttg taggcatctg   19680
taatcccagc cactcgggag gctgaggcag gagaattggt ttaacctggg atgtggaggt   19740
tgcagtgagc tgtgatcgtg ccactgcact ctagcctggg tgacagagca agactctgtc   19800
taaaaaaaaa aagaaaggaa aagaccaatg tggtcctgta ggagtttaga atctaggtgc   19860
tagaggaaag tatatgtagt agtttacaca gtattttta atgtattata tttttttggc    19920
```

```
ctcatagcaa tcttttggtt aagatagaaa tgatcagtct cattttacaa aactaggtat    19980
tgagacactt gtctgaggtg aagtggctat gaaatgattc agtatagatt taaatccaag    20040
tcatcagtct cctgagtcca atgtgttctt ggttatatta ttctgctttc cttggtggtg    20100
gtttctcctg tagcactgcc tttcagccag tatttcagtt ttaacagcat gttggctgca    20160
gtgagccaac attgtgccac tgcatgccag tctgggtaac aaagtaagac tctgtctcca    20220
aaaaaaaaaa attgttcctg atactttatt attagtggaa aacagaaaaa ttaaattttt    20280
gatagtagtg ataagagtaa ttttttttgtc aacttcaata cactgaagac caaaatggtt    20340
atccttaagt gtgccaaaat gagcaaatct ttagcttgat ttcagtgttc cttaggcttc    20400
agttggtgga ccacatatat tattgtgaaa gaaaacattt catttcaaca gctttcccac    20460
cctgtgtgct gtgtactaaa tcagtcctaa gttttacttc tacttggaga aaatgaaga    20520 tatcagagat aggaggtaaa ggaaaagtaa gattgttttg gttgtttgtt tcagaatgtt    20580
gagttatttt ggtgaaaaac agtaaactgt tgggcctaaa ttagagatgc agaggcatta    20640
atatttatct acctaaaata gataacattt ttcagaggga aatgcaaagg attatgtact    20700
ttcattgttc attcaaaact ctggagaggc tcaattttc tactttcaag atcactaggg    20760
tcagtcaatc tgattttgta ttctctgcca aaaatgtttt taaattttct cttttgtccc    20820
aggtcatata aaagtgggtc tggagtaaac aacagaagaa ctgagctatt tttgaaagaa    20880
catgaccacc ttcgaaagta ggtattgaat gtatgtgcat tatgtggttt tccacgttta    20940
ttaattcatt tacttatgta accaacattt tatgatgttt attatactga gtgccttgtc    21000
catgctaatt cattttattc tcctaatgac tcttttcaat agaaaggaa ttgcaactgt    21060 tccaaccata attaggaaag atcctatgct gttgaatatt tcacatcact taattgttac    21120
cttaatatgg ttgttatttt ttttttttt tctctgagat ggagtctcgc tccgtcaccc    21180
aggctggagt gcagtgactc aatctcagct cactgcagcc gcttgcctcc cgggttcaag    21240
cgattctcct gcctcagcct cccaagtagc tgggactaca ggcgtgtgcc accatgcctg    21300
gctaattttt ttgtatttt ggtaaagatg gagtttcgcc atgtagccag gatggtctcc    21360
atctcctgac ctcgtgatcc acccaccttg gcctcccaaa ttgctgggat tacaggcgtg    21420
agccaccacc gcacccggcc agtgcatgtg ctaattctct acagagagag actgagacag    21480
gatgaaactg aatggaataa gagctcctga tgaattagat gagtcgtaga gactgaaaag    21540
atgggcttcg tcattgccct cagtatgata acacaagctt ctaaatactt ctcttaaatc    21600 aattttttt tgtaattaca aatacttgct aggtaataaa ataacattaa aattatcagt    21660
aaaatatgtt tacaaaataa tgtgaaaaac tttagttttt cagtgttttt gtatttcatt    21720
tgccaagtgc tttgaggaag aagtggcaag attttttga aataacttta aataacaaaa    21780
gctaaatgcc tttcatagtg ctcattttag aaagtatgga tagttcaaca acacaaaaag    21840
aaaattgaaa tgacacatta ctacaaattc tgtaatattt tttactcttc agtagattgc    21900 aagcttttc ccatataatt tgattttttg ttttttttaaa ataaatggtg catatattcc    21960
ataataaaga taaccataa attatgtaac catttcccta atgttggcct tttgggttat    22020
gttctgtttt tactattata cacagtaaag cctttgtgtg tatccgtcat gatttcctca    22080
ttctaaattc ctaaatcaga attgcaggat taaagaacac actcatttgc aaagtttttc    22140
tataatattg gcaaatttcc aagtttgata ttttgcagta gggtcggacc ttttatggct    22200
agaactatgt ttaagctttt gcttcttcat aaatattgtt ttttaatgtt aatgtaattt    22260
tttacttgct ccaaaagcac atattttgc ctggaaaaag agtaaatcag tttttgtaaa    22320
```

```
tgaatgccat acttaaacac acacacacac acacacacaa ctttgtaatg aattgttttt    22380
accagctctc cttaatactc tttttatata aaaataaatg ctgttaggtt ttagcaattt    22440
atgttatgga tgacaaattt cttttgctat atggtggata aagtaacttt cgttttggc    22500 ttctctttcc ctgagtctgt cagtcagaag aaaatactga ctttgaatta gtgtcaagct    22560
tgtaactact tgttttttgc tggactgttg atacattctc atagggtttt tagttgctat    22620
ttagataatt tctctttctt tatgtaattg ttctttttca ctactccctg atattttct     22680 tcttgaaaaa gtatctagtt aattttgtat agttcttctc cccacccaa gaatttctgc     22740 ctttataatc ttttctttct tttttcttta agacagagtc tcactctgtt gcccaggctg    22800
gagtgtcgcg gtgtgatctc agctcactgt gccctctgcc tcctgggttc cagcggttct    22860
cctgcctcag cctcctaggt agctgggact acaggcacct gccactacac ccagctaact    22920
tttgtatttt tagtagagat ggggtttcac tctgttggcc aggctggtct tgaactccta    22980
acttcaagag atccacccac ctcagcctct gaaagtgctg ggattacagg cgtgaggcaa    23040
tgtgcccaga cttttttttt ttttttgactt gagggtctca ctctgtcacc cattgtttct    23100
ctctttgtat ttattttata caagatatat ggcttttct ggccaacatg gtgaaaaccc     23160
atctctacta aaaatacaaa aattagccgg gtatggtggt gggcacctgt aatcccaact    23220
acttgggagg ctgaggcagg agaattgctt gaacccggga ggcggaggtt gcagtgagcc    23280
aagatcacgc tactgcactt cagcctgtgt gacagagcga gactccggct caaaaaaaaa    23340
aaaaaaaaaa agacatggct gattatattc ttgctgtctt tatagatgga gaattaagga    23400
gtagagacag acagactata ttacctcaaa cattgaaatg ccataattta tccagaatca    23460
tacattcatt acttgaccag gcatatgatg cttttttctct agaagcattt tgtcattttg    23520
aataaaatac gtcttctgta tttaccttaa tgaagttgac aactttcaga ggttttcagt    23580
ggtgaagata aacttgaata aggagataac ttacacaagc agaaaaagcc tcatctcttc    23640
tggattcctt taatgccagt ggtcatcacc aggtgtagat cagtcacctt ttacccaggc    23700
tgggaccacc accttctcat ctacaggtgt gtcaccttag caatcttctg catctcactg    23760
tcagccaaca cattttctcc ttccaagcct ctgcagtctc atgagtttgt ctgtattttt    23820
cttcttataa cctaccttgc taccttagcc agcctggatc tcataggaga ttaactgaaa    23880
tactcccaac attgggcctt tcctgtgccc ctgtcttcct gctgtaccct ggcaaaatgc    23940
cagcccaatc cagtctgttg ttctacttct gtatgagagg gctaaagaaa aagcaactag    24000
tcatacagat taactctgtt ttaaattaac tattaaatat tttcaacctc atctgagtac    24060
tctgccttgc ctgatgcctt ttgcttgcct agccctgttt agttctcatt ctcttcaaga    24120
actttaccaa atcttctcct tccccctctt gaccttcctg tctcttcacc tgatacagag    24180
gttcttagct tccacttcat tgagattttt aaggtttga tcttttctat aaattgacct     24240
ataggagtat ccctctttac ccctttccta tagttgttaa gggatggaat atttgtcctg    24300
agaaggccaa tacgtgcatt ggacacttgt ctctatcccc atttgctgtg taagtatttg    24360
actcttcagc catccggtac actgtctctg gtttacacct gctgtctctg tgtcagcact    24420
cattcccgct ttagcccatt gacttcttcc ctcacaacac tactgaactt gctgtcaata    24480
ggcacatcag tgatctcctg catgccaagt ctcatggaca ttttttcttca tgttgtttgg    24540 ctgctgctct gcctgacttg atatcatagt ctccttccct tgaaaccta ggctactgtg     24600 gcactacact ttactgattc tccacatacc tttcttactt ctcttttgtt ttttcctga     24660 gtccctccag atgtggccta ggaatccttt taaacacagt gttccaggca gaaattagtt    24720
```

```
ggagttagtt cacaagatgc aatttatttg ccatccaccc ttgcatttca gctccattat   24780
ttgtccttga catgcttgtc tataaaaaca ctttctcctt cccagagatg gcagctaaca   24840
atacctagca aagagaaatg ggaatttcat tcacaatgtc atagggaaag caattggtaa   24900
aattatttta ctgccaagga taataagatt agagagttga agaaagaggc atgaattctg   24960
aaattgtata gaaccatcta aaaggtaaag ctgaggagtt ttatccatac ttaacaggct   25020
gtgactgttt tcatagaagt actctctgat ttatgggcat gtcattgatt acaactagaa   25080
ttgcagattg tgcacattaa acacatcagc ttaaaaatcc ttgacatttt aaaaatacct   25140
ttggcagagt tttagagtag tcatgatatt taaaatatta tcctaatttg ttggtttcct   25200
agagtatatt ttcatttaat catatgtatg ataagaacat acagacttct tgctgggggc   25260
attggctcat gcctgtaaag cctgtaatct ccgctactca ggaggctgag ttgggaggat   25320
tgcttgaggc caagactttg agattggtct gggcaacata gcaagactct gtctctgaaa   25380
taataataat aataaaaata ctaagtatat ttcttggttt ctagggttaa tttttttca    25440 tcttcctctc attaatttac cacttttatc tgactaagat accttaagtt tctttattcc   25500
ttggattggt agtatagtga aatgattagg gcagggcttt gaagccagag agtcctgggt   25560
tcaaatcctg gtgtggactc tatcttttg gggtaagaac ctttaaattc tctgactttc   25620
cagtgtcttt taaatgggtg aaataaccct tactttatgg aatgttgcaa agatgagaga   25680
ggatgtatgt aaaatgttaa cctattacag agcttgatat ggagtagacg aattctaaaa   25740
ttacattgag ccattttgcc tatagtggtg ttagaataga aagtatact  catacattag   25800 aattgtgcac ctagagctaa gtgattccag ccctgtggaa cccgtcaatg ccagaatggc   25860
atgtaggact agatagatga atgtcacctg accctgattg tctattaaaa ctcaatgtat   25920
ggccagatgc agtggctcac gcctgtaatt cccgcgcttt aggaggccga ggcaggagga   25980
tcacttgaag tcaggagttc aagaccacct ggccaacatg gtgaaacccc atctctacca   26040
aaaatacaaa aataagccag gtgtggtggc aggcgcctat aatcccagct acacaggagg   26100
ctgaggcagg agaattgctt gaacctggca ggcagaagtt gcagtgagct gagatcgcgt   26160
tactccatgc cagcatgggt gacagagcaa tactccatct ccaaaaaaaa aaaaaaaatc   26220
aatttatttt taaattactc ttattagtca ttagtcttat tatatatcag tataatgaac   26280 attttatttta ttcaaatcct tttttttttt agatggagat aataaaattt cagttgcatt   26340
ccacctgttt cttcatgtgc atatccggat gcacatataa tttgttggta ccagttttgg   26400
ttgttttaac gagcatttgt tgagcatcta tgatgtggaa agtattgtgc tgggtgctgg   26460
agatagagaa gttgagtaaa gcatagtggc atcatccctg tcctcagtga gctcagccag   26520
gtggggtggg gagcagaaaa gaaatgtgaa tcggtagttc cagtgcaaag taataagtgc   26580
tttattatga tatgcaaagg tttgtgcgta ccctagagga gcacatgaaa gggagtcatt   26640
actctgctga agcttctgaa agggctttag agaagtcgaa catctgatct ggttcttgag   26700
gaatgagtag gtgttctcca agtagagata gaaaaagatt gaaaagttga aactcagacc   26760
tcatgaccat gcctttgtct tctcttctta aatccgtatc attcctcata cattattaaa   26820
tggatctatt ttgaaacgtc acgcatttac tcatagtcca aaccctctcc caggttatag   26880
gtctcactct ggcacctgaa gaggacacac tgggcaaaag aaagtgagca gtggggggc    26940 tctgagtgtc accggggtca gccgaggctg ccattctttt tcctcataaa tcagatttac   27000
tgaggtagaa tttacttaca gtaaaaatgt atccattttta agtttacagt ttggtacgtt   27060
ttaacaaata tatagactct tttaaccgcc accacagtaa gacagagaac atttctatca   27120
```

```
ccccaaaaaa gttccttatg cccctttga gtcagtcccc gtccctcagt cccgggcagc  27180
tgcttactgg ctttctatca ctatagatta gttttacctt ttccagaatt ttatacaaat  27240
gaattcatac agtctgcact tatttcacct agcatagtgt ttctaagact tattcttttt  27300
cttaaatgtc agtaattgat ttctttcaat agcggaataa cttccattgt atgatatacc  27360
acgatttctt tatccattca accattgttg cacagttggg ttattttcag tttttggcta  27420
ttaaaaacaa aattattatg aacattcata acaaaactt tgtgtggtca catgttctca   27480
ttcctctttt tttttttttt tttgagacgg agtctcattc tgttacccag gctggagtgc  27540
agtggcgcaa tcttggctca ctgcaacctc cacctcctgg gttcatgaca ttctcctgcc  27600
tcagcctccc aagtagctgg aactacaggc gcatgccacc acgcccagct aattttttgt  27660
atttttagta gagacggggt ttcacggtgt tagccaggat ggtcttgatc tcctgacctc  27720
gtgatccacc cgccttggcc tcccaaagtg ctgggattac aggcgtgagc cactgtaccc  27780
tgccgttctc atttctcttg agtaaatact tggagttgta ttgttgagtt gtatggtaag  27840
gatgtgttcc aatttataag aaagtgtcaa acttttccaa agtggttata ccattttgc   27900
attcctgtca gtggtgtgtg ggagttcaaa ttgctttaag cccttgccaa cacgccttc   27960
tattgtaacc attttagtag aagtgtaatg gttttattg tggttttgat ttgtatttct  28020
ctaaggactg gtgatgttaa gccttccttc aagtgcttat taaccattca cgtatcttct  28080
tttttattat tcacaactca caggttattg tgacatttgt atatcttctt tagtaagggg  28140
gtctgttcaa gtcttttgc cttttgttgt gggctttt ctattgtgtt ataagggttc    28200
tttgtgtact ctggatgtaa gtcctttgtc agataaaggt tttgcaagta ttttctctga  28260
gcctgtgact tccttttctt ttcatctggt gactttcaaa agagccgagg tttttaattt  28320
tgatgaaatc tggttgatca gttttttctt tctgattcat gtattttggt cctatttaag  28380
aaatcttggc tatcctaagg ttacagattt ttttcttttg ttttctttca ggagttttag  28440
ttttagcttt tttgtttgtt tgtttgtttt taaacctgca gccaacatca tacagtttta  28500
gctttaacat taggtttata atccactttg gcttcacttt tgtgtgtggt gtaagttaag  28560
ggtcaggatt cattttttt taaacacatg tatattccat tgtttcagta ccatttgttg   28620
aaaagactct tttcctctgt ttaatctttt caaagatgtt gacatctttc tagagaatta  28680
attggacact tgctagttta tttctgaact ttgttctgtt ctgttgacct acagatccat  28740
ccttaggcta gttgtactct ggttactgta gcttcataat aagttttgaa atgaggtagt  28800
gtataagtct cctaacttta tcatgtatct tcaaagttat tttgactcct ctgggtccta  28860
tgcacttcca tataaatttt aatatcacat tgtttaaaag cctgctgaaa tttcaaataa  28920
gattatattg aatctagaga tccatttgga gagaattgac atcttaacaa ctgtaaatct  28980
tccaatccag gaacaaggtc ttatatgaaa atatacaaag aactcttttt tttttttttt  29040
ttgagacgga gtctcgctct gtcgcccagg ctggagtgca gtggcgggat ctcggctcac  29100
tgcaagctcc gcctcccggg ttcacgccat tctcctgcct cagcctccca agtagctggg  29160
actacaggcg cctgccacga cgcccggcta atttttttgta tttttagtag agacggggtt  29220
tcaccgtttt agccgggatg gtctcgatct cctgacctcg tgatccgccc gcctcggcct  29280
cccaaagtgc tgggattaca ggcgtgagcc accgcgcccg ccacaaaga actcttaaaa   29340
ttcaacaatt ttaaagtgga aaaagatct gaacagccat cttaaccaag gaagatatac   29400
agatgataaa ttaagcatgt gaaaagatac ttaatgtaat taagtatcat tagggtactg  29460
caaagtaaaa caacagtaag ataccactgc acaactgtta gaatggctaa aatccaaaac  29520
```

```
actgacaaca ttagaaggaa cactgaagga agtggagtaa caggaactct cactcattgc   29580
tggtgtgaat gcaaaatggt acagcgacat tggaagacac ttacgcagtt ttgttttctt   29640
tttctttttt ttttttccga gacagagtct agctgtgtca cccaggctgg agtgcagtgg   29700
cgcgatctcg gctcactgca tcctccgcct cccgggttta agcagttttc tgcctcagcc   29760
tcccaagtag ctgggattac aggtgcgtgc caccacaccc ggctaatttt tgtattttta   29820
gtagagatgg ggtttcacca tcttggccag gctggtcttg aactcctgac ctcgtgatcc   29880
acccgccttg gcctcccaaa gttctgggat tataggcatg agccaccatg ccgagcctgg   29940
cagttttctt aaaaagctaa atatggtctt accatacatt ctagcagtca tgctcctagt   30000
gatttaccta aatgagttga aaacttacat ttacacaaaa acctgtgcat gaatgtttta   30060
cagcagcttt attcataatt gccaaaaagt tggaagcagt caagatgtcc ttaaataagt   30120
gaatggataa acaaatggtg gtacatccat gcaatggaat attattcagt catacaaagt   30180
aataagcctt taagcctgga aaagacatgg gggaacttta aatgcataaa agcagccagt   30240
ctgtgaaggc tacatactgt ataattttaa ctatataaca ttttggacaa agaaaactat   30300
agagacagta aaaagatcag caattctcag gggttgagga tgggaaatgg aggaagaatg   30360
aataggtgaa gcacaggata cttagggcag taaaactctt ctgtatgata ctgcaaggat   30420
ggatccatga caaaacccct accaccgtgc aatgcaaaga gtcaactcta aagcatggtg   30480
tttagttagt aatttatcag tactgggtga tcagttgtaa cacatgtggc acactaaggc   30540
aagaggtaat cacaggtgga ggagaacggg tgtatagtgt gtactttcta ctgaatattt   30600
ctatatgtct aaaattgttc tagcaataat tctattcatt ttttaaaaag gaaaaagtga   30660
ttttctagga tctcactgct aatgactcag ctttttatttt tttatttttct ccttgaactg   30720 agcaggaatc tgtcaggtgc ttcactttct gtctcccggt aacttgctgt gattatgaaa   30780
atgtttgtgc taaacaaccc atgaacaaag caaataaaga tattccttca tctacccaga   30840
ctgaaaggaa ttatgccacc atatcagtgt taatggaaga gaggttacag ctggtttcca   30900
ctttcatctt tgttttcctg tattttccaa atgtgctctg taaaataaaa agctcttagc   30960
actaaaacag tatatatgta ttctactgca gcttaattgt attcagttaa cataattgaa   31020
gagattaaat aagaaatgta gaaataagta agacgtagat cttaaggatc tctctggtta   31080
actgtaagtg aaagactatc tcaccacaat gcttaatgta aatggtctga ttggttagtg   31140
acaacctcat caattattgc agcatgcaaa gggattgatt tttaaatttt tatttattat   31200
tcattattta gtatgtactt gcttgtttgc tttcttattt agttgcttat ttatttgctt   31260
attactttcc taccatttta aaagaggaag aagatactat ctaagtgatt ttgccaagtt   31320
cttacatttt gttggtttat attgctttaa aatacatgct tgaaatcaca tgtttgctct   31380
tgaaatgtgt gccttttgta gtgtgtgtgt tgggggaaat aagttatttt ttaaaaagag   31440
aattatttaa atatggcttt agtgattcct cagcacgata actggtgatg aaatgtagct   31500
tattgttttc agctagttta aattggtctt gagacaaatg gaaatttgtt tcttaattac   31560
aggctctaga tgactttata gaacatctct gggctattat caagtacttg cttaaaaagg   31620
acaattccac ttgaattata tattttatac cccaaaggaa aataagttta aatttaattt   31680
taaccagatg atgccatctg catggagtca ctctgttgtc gtgtccacac gtccaggata   31740
tgtttaatga atggtgtttg tttactttat ttggtcttag ccaaatgagt aaagacctgg   31800
agactgggca atttgagaag acatttagga atccctggct tttctctgtt gatgccacca   31860
tataagctaa ggatgacagt gggtagggaa tgtgtgtgga attcctgtgt gattcactgt   31920
```

```
aactgtggtg tgctaaatgc atggttaagc tagtgtcagc atcgtcttcc tgtaagttaa   31980
agatcccttc tgtgagcagg actcctgcgt actcatgtat attttgaaat atgctttaca   32040
ggatatttta ggacttaata aaagatgact gatgtgtaag gggacttaaa aggaagaaaa   32100
accccttctt ctgtagggta gcatatttgg gattataatt ttcattttct ttaggttggt   32160
ttcatttaac tttttttttt ttttttttga gtcagggtcg tgctctgtcg cccaggctgg   32220
agtgcaatgg cacgatctcg gctcactgca acttccgcct cccgggttca aggaattctc   32280
ctgcctcggc ctcccgagta gctgggatta caggcgcccg ccaccacgcc cgtctaattt   32340
ttgtattttt agtagggaca aggtttcact atgttggcta ggctggtctc gagctcctga   32400
cctcaggtga tccacctgcc tcaacctcgc aaagtgctgg aattacaggt gtgagccacc   32460
acacctggcc agtggttttc attttcaagt gaatccagca acactctttt tctttgactt   32520
gtagttccag tattgctgta aaattactgt aatttgagga tagttgtcaa tctcaaatat   32580
ataaaatgac caatttcagt gaccatttat ccttttacga aaacctattc tatgaaaatc   32640
caattttgtg caaaaagtgg gaaataagtg ggggcgtaa gtgtttgctt tatgagactt   32700
tatttgattc atgtaaatag aaaatggttt cattacatgt aaaatgtgat ttaaattggt   32760
caaaatgtca ttttcggaaa gtatacctaa gatgtatgta ctcattacgt aatgagtact   32820
aaaattgggt ctcattacac agaacaagga ttctatctgt gtgccacaaa caacttcaaa   32880
gaattttctt tatatgtaat gacacagaaa gttgttcctt agcgtccatt tcaactccag   32940
ttcctcagga acattgaata caaattataa tgagtttatt ttccaactaa agtgtagtag   33000
ttaggctagt ttattagcta gtttagttct gacctctatg gttgagaaca gatacaagag   33060
aattatagaa agcagatagt ggaaatgata aagtgtacct ggctggcttt ctgacgattt   33120
gtgtgaagtg cttggctttg taattttata tttctttcta ggctgataca ttgagtttat   33180
ttagttagaa gtgtatttcc acagactgat tatctgtttt tttaaatgct tcttcacagt   33240
tgtataccac ttaaggtatg tagctttgta gccaatctaa attggaattg ggttttttgtt   33300
attgtcgttt ggtacattgg tcactttata aatgtttaac ttttttgtttt gagttaatta   33360
tagatttgca tgcagtttta agaaataata gagagaggcc gggtgtggtg gcttatgcct   33420
gtgattccag ttacttggga ggctgaggca ggaggattgc ttgaagccca gagttcaaag   33480
atgtagtgag ctgtgatggt gccacagcac tccagcctgg gtgacagtga accccagct   33540
ctacaaagaa aaaaataat aatacaaaga aatctcatgt acaggcctac caaattttgt   33600
gttttgcttt attgcacttt acagatacta ttttttacaa actgaaggtt ggtggcaacc   33660
ctgtgtcgag gaagtcttgc agtgccgttt ttctaacagc atatgctcac ttcgtgtctc   33720
tgtgttacat ttcggtaaca gtattttaga tgttttcatt attatcatat ctgttatagc   33780
gatcagtgat ctttgatgtt actcttgtaa ttgcttacaa cctcactgat agaagagggt   33840
gaacttaata aatgttgtgt atgtgtgggg gttttttttgt tttgttttga cagggtct   33900
ttctcagttg cccccaggct ggagtgcagt ggcatgatcc cagcccactg caacctccac   33960
cttgtgggct caagcaatcc ttctacctca gcctcctgag tagatgggac tacaggtgca   34020
caccactgta ctcggatatc ttaaaattgt ttgtatagac aaggtctcat tatattggcc   34080
aagctagtct caaacacctg gggactcaag taatcctccc acctcggcct cccaaagtgc   34140
taggattaca ggcatgagcc accgtgcccg gccagttgtg tgtgttctga ctgtgtcatc   34200
caccatccat tcccaactca ctcctcctca ggccctctc tattacctga cacagaacag   34260
tattgaaatt aggctaatta atgactttgc agtggcttgt aaatattcaa gtgaaaggaa   34320
```

```
gagttgcaca actctttcaa tcagaaggca gaaaccacta cctttagtga agaaagcata    34380
ccgaaagcca atctaagctg aaaactaggc ctcttgtgcc cgttagccaa gttgtgaaag    34440
caaaggaaaa gttcttgaag gaaattaaaa gtgccactcc agtgaataca caaatgataa    34500
gaaagcaaaa caaccctatt gctgatatgg agaaaatttt aatggtctgg ttagaagatc    34560
aaaccaccca caacattccc ttagcctaag cctaatccag agcaaggctc tcttcagctt    34620
tatgaaggtt gagagaggtg aggaagctgc tgaagaaagg tttgaaatta acagaggttg    34680
gttcatgggg tttaaggaaa gaagccatct ctataatata gaagtgcaag gttgaagcag    34740
gaagtgctgg tgtagaagct gcagcaagtt acccagaaga tctagctaag atcattgata    34800
aaggtggctc cactaagcaa cagatgttta gtgtagaata aacagccttt tgttagaaga    34860
agatgccatt taggactttc ctcctagaga cgagaagtca gtgcctggct tcaaagcttc    34920
aaaggacagc tgactgtctt tttaggtgct gatacagctg gtgactttaa attgaagcca    34980
ttgtgtattt accattccag aaattctaga gcccttaaca gttatgctca atctaccctg    35040
cctgtgctct ctaaattgaa taacaaagcc tggaagacag cacatctgtt taccacatgg    35100
tttgctgaat attttaagcc cactctggag acctactgct cagaaaaaaa agaattattt    35160
caaaatatta ctactctttg acagtgcacc tctgatggag atgtacaagg agaggagtgc    35220
tgttttcatg ccagccgaca cagcattcat tctgaagcct gtggttcaag gagtgatttt    35280
gacttttaag tcttattatt taagaaatac attttgcaag gctaaagctg ccatagatag    35340
ttattcttct gatggatctg tgcaaagtaa attgaaagcc ttctggaaag gagtccccat    35400
tctagatgcc attaagaaca ttcatgagga ggtcaaaata tcaacattaa caggaatttg    35460
gaagaaattg atttcaaccg tcatgaataa cttttgagggg ttcaagcctt cagtggagaa    35520
aataactgcg gatgtggcag aactagcaag agaactagaa ttagaagtgg agcctgagct    35580
gggtgtggtg gctcatgcct gtaatcctgt aatcccagcg cttggaaag ccaagaggag    35640
cggatcaccc gaggtgagga gtttgagacc agcctggcca acatagtgaa accccaactc    35700
tactaaaaat acaaaaatta gctgggtgtg gtggtacaca cttgtaatcc ccgctactcg    35760
ggaggttgag gcagaagaat cacttgaacc caggaggcga aggctgcagt gagccaagat    35820
tgtgccattg cactccagcc agggcgacac agcaagactc tgtctcaaaa aaaaaaaaa    35880
aaaaaagtt agaagcggaa gcctgaagat gtgactgaat tgtgcggcaa tcttatctca    35940
tgataaaacg taaacaggtg aggagttgat tttaacagat aagcaaaaga agtggtttct    36000
tgagatggat tctactggtg aagacgctgt aaacattgtt gaaatgacaa caaaggattc    36060
agaagagtgt agaaacttag ttgataaagc agcagagggg tttgagagga ctgactccaa    36120
ttttgaaaca agctctactg ggggcaaaat gctaccaaac agcatcttat ggtacagaga    36180
aatctctcaa ggccccagtt tttcctaagt gaagagaatt ttagaatcaa tctccatagat    36240
ttgttgggag gatgaagtta tgttttaact tgtttagtaa gacatttagg ataggacgtg    36300
gctcatagta agctctctgt gagtattagc tatcattatt cttaacaaaa ttagtaaatt    36360
aatagattgt ttgctctttt ttactttatt tagtagttta tttcatttat tttatcttca    36420
ttaaggctgt tggcacaaaa ctagtttgtt gatttgggca atataaatct ttatgttcat    36480
attatacttc ctagattttg gaatatctta tgttatgct ctttaatgtg ctaagtggcc    36540
ctgatgaaga cagtcagcca aaccattata ttgaagaagg aggtattaac ccaagttaac    36600
cccctttttt gtgaccttgt ggccacttca ccagatgcct tttggcatgt gtcttgtcta    36660
tctccattgt aagatcttgg caggttagtg ccatatcttt gtagccactt tctgacccag    36720
```

```
tgcccttcag gggtgcttct atacatgttt gttagaagag taagtgcata gttaataatc   36780
atagatttca tcagaatagt gagtttatct ggaaatttat atcaattttc tgcttagatt   36840
tacaatgtgt agttattgag aaactaatag caaaaaatac ttgacactta ctgtgtgcca   36900
ggtactgatc caatcactat acaaacccct ttatttgaac aagtaggttt tattatcctt   36960
gctagtctac agatgagaaa actggggcat ggagaaactt gccctgtgtc aaataactaa   37020
taagtggtag attcagcatt taaatagcca cagtctgtct ttcactaccg tctttgtaat   37080
ttttgaaatt tttaataaca ggatttatat atggtattta tgactttttt ttttcctga    37140 gacggagtct agcttgtcgc ccaggctgga gtgcagtggc gcaatctcgg ctcactgcaa   37200
cctccacctc ctgggttcaa gcgattctcc tgcctcagcc tcccgagtag ctgggattac   37260
aggtgcccgc caccatgccc agctaatttt tgtattttt agaagagatg gggtttcact    37320
gtgttgggca ggctggtcaa ggactcctga cctcatgatc cacctgcctt ggcctcccaa   37380
agtgctggga ttacaggtgt gagccaccgt gcccagctaa attttgtatt ttttagtaga   37440
gatggggttt cactgtattg gccaggctgg tcaagaactt ctgacctcat gatccacctg   37500
ccttggcctc ccaaagtgct gggattacag gcatgagcca cagcacccgg ccggtattta   37560 tgactttta aagctcattt gttccctaat atatgcagta acttagatta cctagtccac    37620
taatttataa tgaaaccttg acttcgtagc atgaacttag aaattctttt ggaaataagt   37680
agttggaaaa atacatgcag atatttattt gagtgcctac tgtgtacttt atgccaagtg   37740
gatacagatg tctagaagtt tgttttccta cttctgctgt aaagatggcc cttttccaaa   37800
ctttacctat tcatttctcc ctaaaatggc tttgtttgtt tctttctttc cagtgtgtgc   37860
tgcataaagg cagacaattt acagataaaa ggtgtatttg gtttcttaag attcttgaat   37920
tctaaagttt agtaagctga aattttagtt aaaaaaaagc ctgtttccca aaaaagaaat   37980
aaacattaag atgtaaatat ttactactta tagacatcag aattatattt gcctatcctg   38040
tctcaacaag ttggttctga ttcttaagtt ctgaatagat gatagtgaca actttgagct   38100
atttaaagag aaagttcatt tctttatgct gtcattaaaa ctgttctgac tctaattgtc   38160
aggtatctct gtgaaaaaa tagatttaag ctaacgaaag tgagatagaa attatttgtt    38220
tggagttttt ttgagacaga gtcttgctct atggcccagg ctggagtgca gtggcatgat   38280
gatttcggct cactgcaacc tatgcctccc gggttcaagc agttctcgtg cctcagcctg   38340
ccgagtagct gggactacag gcacacatta gcatacccag ctaatgtttg tattttggt    38400 agagacagag tttcgccatg ttggccaggc tggtctcgaa ctcctggcct caagtgatct   38460
gcctgcattg gcctcccaaa gtgctgggat taccggcgtg agccaccgtg cctggtcgta   38520
agatggaaat tatatatatt gtatgcgaat gaaattaaat ttatttcgaa gtccaggcca   38580
gccacagtgg ctcacatctg taatctcaga gctttgggag gccgaggtgg gcagattacc   38640
tgaggtcagg agttcaagac caccctggcc aacatggcga aacctcatct ctagtgaaaa   38700
tacaaaaatt agccaggcat ggtggcgggt gcatgtattc gcagctattt gggaagctga   38760
ggcaggagaa tagcttgaac ctaggaggcg gcagctgcag tgagttgaga ttacactact   38820
gcactccagc ccaggtgaca gagcgagact ctgtcttaaa aagaaaaaa attagagtcc    38880 agaattttct ccagatgctt tgaaaaagct agacattctg tatacataaa tgactaaaaa   38940
gtttatagat gtagaaaaat taatacaggt tttacatgtg catttagtaa attcagaatt   39000 tgaattttc ttttatttg cagctcagat cgtctgatag aagagacaat aaggtaggaa     39060
taagtttttg ttttgctttg ttggttttg tttgtttgca cgtaaattta atgaacagtg    39120
```

```
ttacagctgt tttagaatta aagaaaaaac attttaatga acagatcaaa gttcgtttat  39180
cctccttaaa gatgaaattt ttactatgtc ctttccttac aagagacgtt tgacacccaa  39240
agtaacattt ccatagttac tttaattaag ctgttttact taggttaatt tttccaatta  39300
atttatactt aatattttca atctcagtct ttttattccc acttttaaa gcaaagtgat  39360 ttaaagcata atttgataaa taactttatg ccattcatat agactttgct gttatagcac  39420
ctgcagaaaa tctactgcag taatagttca tagtatctgt aataacattg aactagtttc  39480
ttgcttaagt taagggacat ttatttcttg ttttgaactg cttagctttc taggtttgat  39540
gaattttaaa gtatctattt tatgacagta aaaaagtaca ttaactaggt ctctgtgctc  39600
tagaattcac caatgtgtaa agcattggtt ttcaggaaag gtaaatcaaa gtacatgaca  39660
ataacaaaca tttgtatttt tttttttttt tagatggagt ttcactcttg ttgcccaggc  39720
tagagtgcag tggtgccatc ttggctcact gcaacctccg cctcctgggt tcaagtgatt  39780
ctcctgcctc aggctcctga gtagctggga tttcaggtgt gtcccaccat gcctggctaa  39840 tttttttgtaa ttttagtagt gacagggttt catcatgttg gccagtctgg tcccgaactc  39900
ctgacctcag gtgatctgtc caccttggcc tcctaaagtg cagagattac aggtgtgagc  39960
cactgcgccc agccacattt gtattcttac catggatatt ggacctgtgc taaaagtact  40020
ttgcatgcat tatttatt gattttctca ataacccatt agatagacac aaatcattag  40080
gaactatctc caaaacaaaa aagaaattaa gtaatttgcc tgtggtcaca tgactagtaa  40140
atagtattaa ggattcagat cctgattcag tcttagtcca actctagaaa cagagctcta  40200
tttaaaccac tgctatattt accacattgc agaaagaata caaggttttg ggtctgattt  40260
ggtttggaac ctgcctgtgc tgtttattag atcttagatt tctgttcttt agataattaa  40320
cttcttggaa ctttcatttt cttatctgtt taaaaatata gtattgatga taatacttat  40380
ctgtaagact gttaaggata atgtgaggaa aatgcctgat ctaatactag gtaatctgta  40440
aatggtagct atattattaa taccaatcct ttcttttta gctttttatt tggatatcat  40500
ttcagatttc agaaaaattt cagtagtgaa aagaagtcct atatacccctt tacccaactt  40560 ctacaaagtt taacatacat tgatgctctt tactcctaaa tatttcagtg ttcgtttcct  40620
aaatatctgt ttcttttgta tggcttcatg gattctttat tcagtggatt ggaatatttt  40680
ccatcattaa tcatcttaat acattttagt cttttataac agtaagccat gattgtgtct  40740 tgaattttg tttaaattgt atgtgctgag ccttccacct gaagaaagtt ttcacagaat  40800
ttccttatgt tgactgaagt ttcttccttg taactttttc cttttcatca gcacatgaga  40860
tctgatcaca ttttgccagg aattctttac ttaaagtttc ccaatcatcc ttttctttt  40920 ttccttatt tccctttctt tctgcctgct cttctagggc caggctgcct taattaagct  40980
ttcacttcag aactggccta tttaagggct ggtaatatga gtataaaaac ttggggtacc  41040
tcatagggca aaaagaaat taaaggaac aattgagaac cattgaattg ttactattat  41100
tttgctagtt agaaaacatg ttattaggtc ttttatttca gtattttccc ttgtttcaaa  41160
atatgatagg cattacaaga aaagtttcac tgagtataaa gctagttatg atttcttatg  41220
aagaatataa agtttgtgtc aaatagtatt tttgcatatt ccatatggaa aaatttacct  41280
tttcctttta gagatacatt ttaaaactat gtgagcaact gaatatagac tttgacatca  41340
acttattgaa aagaactagc attttttaaca tttataaatt catttctaac ctttaaatgt  41400
atgacttgta ttatctgttg ttgaaaaaaa ggtgactgag ttcagttcac agagcaggta  41460
acaggtaaga aagttgaagt tcctgtaagc atatcaatga tttatcattt taaaagcatt  41520
```

```
atgtattatt tagagcttat attttgcttc taaatatttg acccttgaaa taacagccta   41580
gatttcattc tgcttgactc tgagtcatga aatgagatga gaaagtatgt ctagatatac   41640
tttgtggtac tggaaatcat gcatcttcaa caagttaaca taatgtatga tgatgatatc   41700
tattccccaa ggaatacaaa gtgctttgca gaaattattt tttaacctct gtccacttgt   41760
gagtcaaagt ctacaggaaa tggtgatagt tccagtttga aaaacagaag caggcccagc   41820
atggtggctc acacctatga tcctaacact tgggaggct gaggcgggag gactgcttga   41880
ggccagaaac tcgagtcagc cagagcaaca tagtgagacc ccatctttac aaaattgttt   41940
ctaaaaagct aggcatggtg gtgcacatct gtaagccaac cacttggaag gctgaggcag   42000
gaggagcact tgcacccatg aggtcaaggc tgccatgatg gtgctactgc agccgtgcct   42060
gcatggcaca gtgaggccgt gtctcaaaaa aataataata tatcattcaa agattgatat   42120
atgggccagc ataggtttga aagctgttac tttatacaag accatagtat ctacttgcaa   42180
taccttgtaa acttttctac aaaacagcca cattttcaat gtatcacatt ttgtcataat   42240
ctctcaaact gaaaaattat gaataagaac taaatgatgc aaaggaagtt gtttgttaag   42300
ctcttcttgt gttcctttca tttggggatc aaaaattcag tgtattgtgt ggttgacatc   42360
gctccctcct tctgctctaa tcttgactgg tgattctcta cacctccaac attgttctgg   42420
tcctagatgt ccttcctcca ttaccctaaa ataatttcct ctattggatt acctacttgg   42480
gattagtgcc ttccactttc ttactttatt cccttattat gctgaaccat gtccttagta   42540
acttcctgag aaagaacagg aggtaaattg ttttggactg cccacatcca aaaagtcttt   42600
attctgctcg tattcttgat tcattattta acctaaccaa gatagaattc tgagttggaa   42660
ataattttga aattttaaa ggcattgctt ctaaagtcca ggctggcatg cttctaaagt   42720
ccacagtggc atgcgtcttt tccagtccaa tgctctgggc attgagtgaa ctcttacaat   42780
ctggaaactc atcttcagtt cttggaaatt atcttaacgt tctttatcat tttcttccct   42840
cttctttctc tgttgtttca tgcaaaaaaa tattaaaaag gttatgtgtt gggccttctg   42900
aattgatcct ttcttacctt ctctctgttt ctgttgatct ttttgtttaa cattctggga   42960
gatttactga atttctcctt ccaattcttc tattacattt ttatatcagc tcttcattta   43020
atttacatga gctctttcgt gagagacaga tacacacatt tatgtgtatg ttttgtggat   43080
gtagtaatct tttatctctc tgaaaacatt aaatgtaatt ttattttaga gtttcttgag   43140
cttcctttat tgccctgttt gctcagcctc acttttctgt ttgctgggtg gtttatttga   43200
actctgcctt tcatgttacc tcctcacaca tctagtgatt attggctgtt ccttcatatt   43260
taagggtgtg actccaaaag aggatgagct tccagtcact cattgctgtt acccaggctg   43320
gagtgcagtg acatgatcat ggcttactgc agccttgacc ttctgggctc aagcaatctt   43380
cccacctcag cattctgaat agctggtact actggcacac accaccatgc ccagctaatt   43440
tttttttttt tttttgtat ttttctgtag acatggtgtt tctccatgtt gtgaaaagaa   43500
tgtgtgttgg gaaactcatc ctgtgagcat agggtggtga cacttgttga gtgttaggcc   43560
tcaccatgcg tgatcaggcg gacctggctg tttcactggg gacttcaaat tgccagacct   43620
ctatgtctct tctcctgagc taggtcttct actggactag gggcagccac ctagctgcat   43680
gcgttaggaa gggcaatttt gggttatggc aactccttgt acaaatttct acaaatctcc   43740
atttttaacc ctactccaca gttctgccct cagagagagt gatcccttcc attcttgagc   43800
atttctgaga tctgtggaaa acttttttaaa atcattgctt gactcataat tttattgagg   43860
tgcatcacag tggtggattt ggagctgcta atgtattttt ttgtttgttt tagttttacc   43920
```

```
cagttacatt tctttattct gaaatgtcat ttcaaaagac cagaccataa tatctccaca    43980
tgaacagata ttttctaga ataggcctaa aagtattggg aagatgggat tgtcagcatt    44040
aaaacacata ggaaatcagg accctggaag aactgtaata ttctctagga cttttcattt    44100
tctaaatttg cagatattgc ctgtgatttc agttgaaagt gatccaaatc ctagtgtgtc    44160
catgttaatt gtgtgtgtag cttcaaatgt tatttaacgt ttcttaatca agtggaattt    44220
ttctaatgtt ttcatttttc ttttattaga cacttgtata ttgtatatta tacaagtaca    44280
gtgttcttat tgtaacaact taaataatac taaaacggat aaagaaaaag tcagccgggc    44340
gcggtggctc acgcctgtaa tcccagcact ttgggaggct gaggcgggcg gatcacgagg    44400
gcaggagttc gagaccatcc tggctaacac ggtgaaaccc cgtctctact aaaaatacaa    44460
aaaattagct gggcgtggtg gcaggcgcct gtagtcccag ctactcagga ggctgaggca    44520
ggagaatggc atgaacctgg gaggcggagg ttgcagtgag ccaagatcgc gccactgcac    44580
tccagcctgg gtgacagagc aagactccgt ctcaaacaaa aaaaagaaa aagaaaaagt    44640 cagtctcctg gtagtacccc tccattctta accccctgaag caacttgtgt taactgacag    44700
ttgtgtatcc ttctgatacc tttttcactg tcatacagac atcccaaaag atgtttgttt    44760
ctgtaattat tagaggattc atattctata cattctgtgg cttgctttaa tcactcaata    44820
tgttataaac atcccttcaa gttaatagaa atactaactt tgttttgttt tgtttgagac    44880
tgcgtcttgt gttgtcaccc aagctggagt gcagtggcgc gatctcagct cactgcaacc    44940
tctgtctcct gggcttcaag tgattcttca ccctcagcct cccagtagct gggattacag    45000
gcgctcacca ccacgcctgg ctaattttg tatttttagt agagaagagg tttcaccatg    45060
ttggccaggc tggtcttgaa ctccttggcc tcaagtgatc cacctgcctt ggcttcccaa    45120
agtgctggga ttacaggcat gagccaccgc gcctagccct aactcatttt tttaaatacc    45180
caaatactat gtaatcactg cctgtgattt cagttgaaag tgatctaaat cctagcatgt    45240
ccatgttaat tttgtgtgtg tgtgtagctt cagatgttgt taacatttct taatcactca    45300
ggtgggattt ttctaatgtt cttttcattt ttcttatta gatatttata tattatcgaa    45360
gtacatttgt atattatcaa aatgttctta ttgtaacaac ttaactaata ctaaaatgga    45420
taaaggaaaa gtcaatctcc tggtagtacc cctccattct taacctctga agtaacttgt    45480
gttaagtgac aattgtgtat cttactgata tacaactttt tcactgtcat acaaacatcc    45540
ccaagggtgt ttgtttctga aaatattaca gcattgatat tctgcacatt ccgtagcttg    45600
ctttaatcac tcaatatgtt ataaacaccc cttcgtgtta atagaaataa tactaactca    45660 tccttttaa taaccaaagt atggttatat cataatctat tataccattc aaatgttact    45720
tccagttttg ggggattttt ttttttggt ctttttgctg ttgttgttca tttttacta    45780 ttccaaaaat gcttcaacaa atattctttt acagattgaa tgttgcttat ccaaaatact    45840
tgggaccaga agtcttgggg atttctgatt ttcagattag ggatgttcaa cctgtatata    45900
cctccttaca cacttttgtt tctcttttgc catctcaaat cttgaaattc aagttttgat    45960
tcatgtgtca tttgtttaga atattccttc tagcatttcc cttcaataag atacatggtg    46020
gtttactctg tgagacctta cctggccaaa aatgtgttca ctcagctccc agatagatcc    46080
agctatgaga gcctcttaag caatggcata tcaggcagtg atgcatccat cactgggctc    46140
ttcccttagg ggctgggcat cacaccagct acaagactat cggctctctg cttgtcatct    46200
ttctggctgc atgtagcagt cctttcccag cttcagtgcc tgggagcaat ttcactgcaa    46260
cccctgtgta tgcagatcca tagtcttcca ctgtctgggt tcctcaggaa gcaaggaagc    46320
```

```
cctaggtctt tgcctcaagc ttgaagaaaa atctaagctt ccctgctgtc agttccctgg   46380
ttctctcttc acttcagaga gtatagccct ctacctggct tcttccctg gagatctcaa    46440 gggaacttgg ggcctcagat ggaccctcct tagtgtgtct gcttttattc ttgtgctact   46500
ccatggagga aatggaccaa aggtcaagtc aggaatttat actctcacca tcatcttccc   46560
caaatctcaa tctcttgatt taaaaaaaaa aaaaaataga tattttcaaa attgctcaac   46620
agcatttcat tttctgttgc tatttataat gtcaacatgc aaagcactcc tctgagtgtt   46680
acatatcaaa gtggatactg accctgccct ctagggctct aatgtccaga gagataagac   46740
tatgggaaat gaataatcct ggaagtgata gcaaaatgat actaacttag gccaagctt    46800 ggtggctcac acctataact ccagcacttt gggaggcgga ggtaggagga tggcttgagc   46860
ccaggagttt gagaccagcc tgggcaacat agggagaccc catctctaga aataatttaa   46920
aaattagaaa aaaaaaatta gccaggcatg atggcacatg cctgtagtcc cagctactca   46980
ggaggctgag gtgggaggat tgcttgagcc cagggagtca aggctgcaat agccacagtc   47040
acaccactgg gctccagcct gggtgacgga gcaggaccct gtccccaac ccccaacccc    47100 ccccaaaaaa aggatattaa ctcaagagat cttttaaaca ggacatcaag gtagtcacag   47160
ggaagagatt gtgttcgacc aaaagtgact ttctcttttc tctttaatct tttctttttt   47220
ttgagacagg gtctcgctcc attattcagg ctagagtgca gtggctccat cacagctcgc   47280
tgtagccccc ccctcctggg ctcaattgat cctctcacct cagcctcccg agtagctggg   47340
actacaggca cacatgtcta gctaatttt tattttggta gagttgggat ttcaccacat    47400
tgcccaggat ggtcttgaac ttttgggctc aagtgatcct cccacctcgg tcttccaaat   47460
tcggtgctgg gattacagac gtgagccacc acacccagct gttttagcca cgtttaatga   47520
gtctgtgacc tttgtcagcc atcatggaaa cccagcataa tgttgcatgc atgcctagtt   47580
ggttctcaag tagaatttg gaacataatc tcttcataaa ttaagggctg gttgtgtatt    47640
cacattttat gatatttat atttcttttc tattttata attataattc cctttcaaca    47700
gtttttcctg attaaagata ttttagtagc tggcttcttt ttaaactctt tttaaacttt   47760
ttaaagtttt taaactttaa attttaagaa gcttttgtaa tatgtgattt gtctgtttat   47820
gccttatttt gtttgttatt ttgaagcaaa cataggaagt ggcttactgc cttgtataaa   47880
aagatatcag agaacagtgg agtcatttgg aaaaagcgca gtggtaaagt ggcttcggaa   47940
gtgatttttt ccccttattt tctggcacag tgctttctaa gatgatgttg ctcactgtag   48000
ttttctttca cttttaaagg catgatggtt ccaggcagga taatcttaaa tggtgatttg   48060
tcatcttttt ttccccttgc agcattgcta tggcaacaaa agaaaatatg acttcacaga   48120
gaggaatgtt gaagtcaatt cacagcaaaa tgaacactt ggccagtatc cttttttgaat    48180 gttcgcagtc tgtgttttga gggtagaggg gagaagtgtc tgtgtgtgct tttataggg    48240 gcaggttgcc atcatcagta gcagtagagc ccatcagtaa ttgcataata tgaatatact   48300
gtgcattcct actttgtgaa agtttatgct ctttagtacc attcctaaaa gactgcacct   48360
cagaagtttc ttactactag atgtagaaga aaaaaattat aaatgtgaat ttaaaaatta   48420
tccaccaatt tcttctacat tttagaaagc ttttaaattc atgttagaac tccacactat   48480
acattattct tacctaaaca tgataaatta tatgcctttg ttgttttttcc catttagaga   48540 taagtcagtg gcagatgctt ggaagggga aggaaggaga cagccacccg tgcagatgag    48600
ctatagctac tgatggagtt tgtaactcta tgcacaggct gaattc                  48646
```

US 7,985,571 B1

ISOLATED GENOMIC POLYNUCLEOTIDE FRAGMENTS FROM CHROMOSOME 17 THAT ENCODE HUMAN CARBOXYPEPTIDASE D

PRIORITY CLAIM

This application is a continuation of application Ser. No. 10/457,716, filed Jun. 9, 2006, the contents of which are incorporated herein by reference. Application Ser. No. 10/457,716 claims priority from provisional application No. 60/386,927, filed Jun. 7, 2002, the contents of which are incorporated herein by reference.

FIELD OF THE INVENTION

The invention is directed to isolated genomic polynucleotide fragments that encode human carboxypeptidase D, vectors and hosts containing these fragments and fragments hybridizing to noncoding regions as well as antisense oligonucleotides to these fragments. The invention is further directed to methods of using these fragments to obtain human carboxypeptidase D and to diagnose, treat, prevent and/or ameliorate a pathological disorder.

BACKGROUND OF THE INVENTION

Chromosome 17 contains genes encoding, for example, asialoglycoprotein receptor-2, ribosomal protein L26, ribosomal protein L38, golgi snap receptor complex member 1 and carboxypeptidase D; the last of which is located near the chromosome 17 centromere and will be discussed in more detail below. Mutations in the chromosome 17 centromere region underlie hereditary forms of prostate cancer, choroidal dystrophy, retinal cone dystrophy 2, and psoriasis susceptibility.

HUMAN CARBOXYPEPTIDASE D

Human carboxypeptidase D, a carboxypeptidase E-like enzyme, is one of a family of enzymes that catalyze release of C-terminal basic amino acids (Arg and Lys) from oligopeptides such as bradykinin, kallidin 10 and the anaphylatoxins C3a, C4a and C5a. Carboxypeptidase D is disposed predominantly in the trans-Golgi network and also cycles to the cell membrane. Vesicles of anterior pituitary enriched in carboxypeptidase D are also enriched in peptide hormones such as adrenocorticotrophic hormone, and it is believed that the enzyme participates in the processing of the co-resident hormones (Varlamov et al., J. Biol. Chem. 274: 14759-67, 1999; Dong et al., Neuroscience 89: 1301-17, 1999). Duck carboxypeptidase D is known to be a hepatitis B virus receptor (Breiner et al. J. Virol. 75: 143-50, 2001). Human and mouse carboxypeptidase D have been found to have many characteristics in common with bovine carboxypeptidase D (Ishikawa et al., 1998, Gene 215:361-370). Carboxypeptidase D has also been found to be present in the fat/fat mouse, normal mouse, rat and bovine tissues (Song et al., 1995, J. Biol. Chem. 270:25007-25013).

OBJECTS OF THE INVENTION

Although cDNA encoding the above-disclosed protein, carboxypeptidase D, has been isolated (e.g. see accession no. D85390) and the gene has been localized to the centromeric region of chromosome 17, its exact location on chromosome 17 and exon/intron/regulatory organization have not been determined. Furthermore, genomic DNA encoding the polypeptide has not been isolated. Noncoding sequences play a significant role in regulating the expression of polypeptides as well as the processing of RNA encoding these polypeptides.

There is clearly a need for obtaining genomic polynucleotide sequences encoding the carboxypeptidase D polypeptide. Therefore, it is an object of the invention to isolate such genomic polynucleotide sequences.

There is also a need to develop means for identifying mutations, duplications, translocations, polysomies and mosaicism as may affect the carboxypeptidase D gene.

SUMMARY OF THE INVENTION

The invention is directed to an isolated genomic polynucleotide, said polynucleotide obtainable from human chromosome 17 having a nucleotide sequence at least 95% identical to a sequence selected from the group consisting of:
  (a) a polynucleotide encoding human carboxypeptidase D depicted in SEQ ID NO:1;
  (b) a polynucleotide consisting of SEQ ID NO:2, which encodes human carboxypeptidase D depicted in SEQ ID NO:1;
  (c) a polynucleotide which is a variant of SEQ ID NO:2;
  (d) a polynucleotide which is an allelic variant of SEQ ID NO:2;
  (e) a polynucleotide which encodes a variant of SEQ ID NO:1;
  (f) a polynucleotide immediately adjacent to the 3' end of SEQ ID NO:2, obtainable from the centromeric region of chromosome 17 and having a nucleic acid sequence depicted in SEQ ID NO:3;
  (g) a polynucleotide which hybridizes to any one of the polynucleotides specified in (a)-(f) and
  (h) a polynucleotide that is a reverse complement to the polynucleotides specified in (a)-(g).
as well as nucleic acid constructs, expression vectors and host cells containing these polynucleotide sequences.

The polynucleotides of the present invention may be used to modulate levels of human carboxypeptidase D in a subject in need thereof and specifically for the manufacture of a gene therapy for the prevention, treatment or amelioration of a medical condition by adding an amount of a composition comprising said polynucleotide effective to prevent, treat or ameliorate said medical condition.

The invention is further directed to obtaining human carboxypeptidase D or variant thereof by
  (a) culturing host cells comprising these sequences under conditions that provide for the expression of said polypeptide and
  (b) recovering said expressed polypeptide.

The polypeptides obtained may be used to produce antibodies by
  (a) optionally conjugating said polypeptide to a carrier protein;
  (b) immunizing a host animal with said polypeptide or peptide-carrier protein conjugate of step (b) with an adjuvant and
  (c) obtaining antibody from said immunized host animal.

The invention is further directed to a nucleic acid molecule including but not limited to a polynucleotide fragment, antisense oligonucleotide or antisense mimetic comprising a sequence of nucleotides which specifically hybridizes to non-coding regions of said polynucleotide sequences of SEQ ID NO:2 (carboxypeptidase D gene) or to the centromeric region of chromosome 17 depicted in SEQ ID NO:3. These sequences may be used to modulate levels of human carboxypeptidase D in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, an "antisense oligonucleotide" is a molecule encoding a sequence complementary to at least a portion of an RNA molecule. The sequence is sufficiently complementary to be able to hybridize with the RNA, preferably under moderate or high stringency conditions to form a stable duplex or triplex.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising (a) isolating genomic DNA from said subject;
  (b) detecting the presence or absence of a variant in said genomic DNA using a probe or primer derived from the polynucleotide of claim 1; and
  (c) diagnosing a pathological condition or susceptibility to a pathological condition based on the presence or absence of said variant Probes or primers derived from SEQ ID NO:2 (carboxypeptidase D) may be used to identify variants including but not limited to mutations, duplications, translocations, polysomies and mosaicism on the carboxypeptidase D gene and may be used to identify patients with or having a propensity for an endocrine disorder, hepatitis B or obesity. Oligonucleotides derived from SEQ ID NO: 3, or the polynucleotide itself, may be used to identify mutations, duplications, translocations, polysomies and mosaicism that may occur at or near the chromosome 17 centromere. An oligonucleotide derived from SEQ ID NO:3 may be used to identify patients with hereditary forms of prostate cancer, choroidal dystrophy, retinal code dystrophy and psoriasis susceptibility.

DETAILED DESCRIPTION OF THE INVENTION

The invention is directed to isolated genomic polynucleotide fragments that encode human carboxypeptidase D, which in a specific embodiment is the human carboxypeptidase D gene, as well as vectors and hosts containing these fragments and polynucleotide fragments hybridizing to non-coding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein, "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The human carboxypeptidase D gene is situated in chromosome 17 genomic clone AC006050. The exon/intron regions of the gene are shown in Table 1.

The polynucleotides of the invention have at least a 95% identity and may have a 96%, 97%, 98% or 99% identity to the polynucleotide depicted in SEQ ID NO:2 as well as the polynucleotide in reverse sense orientation, or the polynucleotide sequence encoding the human carboxypeptidase D polypeptide depicted in SEQ ID NO:1.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutal et al. (Com. App. Biscay. (1990) 6:237-245). In a sequence alignment, the query and subject sequence are either both nucleotide sequences and both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotide depicted in SEQ ID NO: 2. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42 C, can be used, e.g., 5×SSC, 0.1% SDS, 0.25% milk, and no formamide; or 40% formamide, 5×SSC, 0.5% SDS). Moderate stringency hybridization conditions correspond to a higher temperature of 55 C, e.g., 40% formamide, with 5× or 6×SCC. High stringency hybridization conditions correspond to the highest temperature of 65 C, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequence depicted in SEQ ID NO:1 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human carboxypeptidase D gene. These include but are not limited to an intron, a 5'-non-coding region, a 3'-non-coding region and splice junctions (see Table 1), as well as transcription factor binding sites (see Table 2). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 2000 or about 5000 nucleotides in length may be used.

TABLE 1

Exon/Intron Regions of the Carboxypeptidase D Gene in Genomic Clone SEQ ID NO: 2.

| Exon | Nucleotide | Peptide |
|---|---|---|
| 1 | 21226-21972 | 1- 249 |
| 2 | 27234-27479 | 250-331 |
| 3 | 63084-63227 | 332-379 |
| 4 | 63908-64078 | 380-436 |
| 5 | 64919-65266 | 437-552 |
| 6 | 65749-65940 | 553-616 |

TABLE 1-continued

Exon/Intron Regions of the Carboxypeptidase D Gene in Genomic Clone SEQ ID NO: 2.

| Exon | Nucleotide | Peptide |
|---|---|---|
| 7 | 69634-69801 | 617-672 |
| 8 | 74015-74125 | 673-709 |
| 9 | 81219-81320 | 710-743 |
| 10 | 84551-84691 | 744-790 |
| 11 | 86043-86216 | 791-848 |
| 12 | 87936-88265 | 849-958 |
| 13 | 91798-91992 | 959-1023 |
| 14 | 93955-94092 | 1024-1069 |
| 15 | 97585-97713 | 1070-1112 |
| 16 | 98499-98594 | 1113-1144 |
| 17 | 98705-98770 | 1145-1166 |
| 18 | 103424-103555 | 1167-1210 |
| 19 | 104121-104306 | 1211-1272 |
| 20 | 104614-104709 | 1273-1304 |
| 21 | 106828-107055 | 1305-1380 |

"tga" 107056-8

TABLE 2

Transcription Factor Binding Sites on the Carboxypeptidase D Gene (114104 base pairs).

| Transcription Factor | No. of Binding Sites |
|---|---|
| AP1FJ_Q2 | 4 |
| AP1_C | 19 |
| AP1_Q2 | 4 |
| AP1_Q4 | 5 |
| AP4_Q5 | 7 |
| CEBPB_01 | 7 |
| DELTAEF1_01 | 18 |
| GATA1_02 | 6 |
| GATA1_04 | 9 |
| GATA1_06 | 12 |
| GATA2_02 | 8 |
| GATA3_03 | 6 |
| GATA_C | 13 |
| LMO2COM_01 | 7 |
| LMO2COM_02 | 17 |
| LYF1_01 | 38 |
| MYOD_Q6 | 26 |
| MZF1_01 | 31 |
| NFAT_Q6 | 25 |
| NKX25_01 | 50 |
| NKX25_02 | 4 |
| S8_01 | 20 |
| SOXS_01 | 75 |
| TATA_C | 11 |
| TCF11_01 | 80 |
| USF_01 | 12 |
| USF_C | 16 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000, 2000 or 5000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides
Isolated Polynucleotide Sequences

The human chromosome 17 genomic clone of accession number AC006050 has been discovered to contain the human carboxypeptidase D gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequences of AC006050 were compared to the human carboxypeptidase D cDNA sequence, accession number D85390.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1999, *PCR: Applications: Protocols for Functional Genomics*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired carboxypeptidase D gene may be accomplished in a number of ways. For example, if an amount of a portion of a human carboxypeptidase D gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human carboxypeptidase D polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human carboxypeptidase D polypeptide.

A gene encoding human carboxypeptidase D polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human carboxypeptidase D gene operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NO: 2 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (VIIIa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention. Preferred terminators for filamentous fungal host cells are obtained from the genes encoding *Aspergillus oryzae* TAKA amylase, *Aspergillus niger* glucoamylase, *Aspergillus nidu-*

*lans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C(CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral protease genes (nprT, nprS, nprM), or the *Bacillus subtilis* prsA gene. Further signal peptides are described by Simonen and Palva, 1993, *Microbiological Reviews* 57: 109-137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophile* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-O-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9,* 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, human carboxypeptidase D can be assayed by its ability to release C-terminal basic amino acids from oligopeptides such as bradykinin or synthetic substrates such as hippuryl-Lys or hippuryl-Arg, or $^3$H-benzoyl-Phe-Ala-Arg (Stack et al., 1984, Life Sci. 34:113-121).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human carboxypeptidase D polypeptide produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the human carboxypeptidase D polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human carboxypeptidase D polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human carboxypeptidase D polypeptide.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments or antisense nucleic acids hybridizing to non-coding regions of SEQ ID NO:2 may be attached to a substrate. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides depicted in SEQ ID NO:2 or SEQ ID NO:3. Alternatively the microarray may comprise a polynucleotide(s) hybridizing to said non-coding region and/or SEQ ID NO:3 and/or coding regions of SEQ ID NO:2.

Uses of Polynucleotides

Diagnostics

Polynucleotide fragments containing noncoding regions of SEQ ID NO:2 may be used as probes for detecting variants from genomic nucleotide samples from a patient. The variants may be allelic variants or substitution, insertion or deletion nucleotide variants. Genomic DNA may be isolated from the patient. A mutation(s) may be detected by Southern blot analysis, specifically by hybridizing restriction digested genomic DNA to various probes between 10-500 nucleotides in length, preferably between 20-200 nucleotides in length, more preferably between 20-100 nucleotides in length and most preferably between 20-50 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998). Single base extension (see, for example, U.S. Pat. No. 6,004,744) may be used to detect SNPs. Additionally, primers may be obtained by routine or long range PCR that yield products containing contiguous intron/exon sequence(s) and products containing more than one exon with intervening intron. The sequence of the amplified genomic DNA from the patient may be determined using methods known in the art. Such probes may be between 20-5000 nucleotides in length and may preferably be between 20-50 nucleotides in length.

Additionally oligonucleotides derived from SEQ ID NO:3 may be used to detect disorders associated with defects in the centromeric region of chromosome 17. Such defects include but are not limited to mosaicism, mutations, deletions and duplications.

Thus the invention is thus directed to kits comprising these polynucleotide probes and primers. In a specific embodiment, these probes and primers are labeled with a detectable substance.

trans

Antisense Oligonucleotides and Mimetics

The antisense oligonucleotides or mimetics of the present invention may be used to decrease levels of a polypeptide. For example, human carboxypeptidase D has been found to be associated with the processing of polypeptide prohormones into their mature (hormone) forms. Therefore, the human carboxypeptidase D antisense oligonucleotides of the present invention could be used to inhibit the conversion of a prohormone into its active form in medical conditions in which the hormone is present in excess.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

The human carboxypeptidase D gene may be used to via gene therapy to correct a deficiency state in which the lack, or relative lack, of the enzyme impedes the processing of an endocrine hormone, e.g., pro-ACTH to ACTH (Dong et al., Neuroscience 89:1301-17, 1999). Therefore, the human carboxypeptidase D gene may be used to treat an endocrine disorder. Additionally, the human carboxypeptidase D gene may be used to treat hepatitis B or obesity.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN·· and LIPOFECTACE··, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4 spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated genomic polynucleotide, said polynucleotide selected from the group consisting of:
   (a) a polynucleotide consisting of SEQ ID NO:2 which encodes human carboxypeptidase D depicted in SEQ ID NO: 1;
   (b) a fragment of (a) consisting of nucleotides 21226-107055 of SEQ ID NO:2, which encodes a polypeptide that has carboxypeptidase D activity and (c) a full complement of (a) or (b).

2. A nucleic acid construct comprising the polynucleotide of claim 1.

3. An expression vector comprising the polynucleotide of claim 1.

4. A recombinant host cell comprising the polynucleotide of claim 1.

5. A method for obtaining human carboxypeptidase D or a variant thereof comprising (a) culturing the recombinant host cell of claim 4 under conditions that provide for the expression of said polypeptide and
   (b) recovering said expressed polypeptide.

6. A composition comprising the nucleic acid molecule of claim 1 and a carrier.

7. An isolated genomic polynucleotide, said polynucleotide selected from the group consisting of:
   (a) a polynucleotide 114,102 nucleotides in length, which (i) is at least 99% identical to SEQ ID NO:2 and (ii) encodes a polypeptide having human carboxypeptidase D activity;
   (b) a fragment of (a) consisting of nucleotides 21226-107055 of SEQ ID NO:2, which encodes a polypeptide that has carboxypeptidase D activity and
   (c) a full complement of (a) or (b).

* * * * *